United States Patent
Hung et al.

(10) Patent No.: US 8,178,493 B2
(45) Date of Patent: *May 15, 2012

(54) METHOD FOR INDUCING ANGIOGENESIS IN A HEART OF A PATIENT

(75) Inventors: David T. Hung, Belmont, CA (US);
Brian H. Annex, Durham, NC (US);
Kevin P. Landolfo, Chapel Hill, NC (US); W. Michael Kavanaugh, Mill Valley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/419,038

(22) Filed: Apr. 6, 2009

(65) Prior Publication Data
US 2009/0221504 A1   Sep. 3, 2009

Related U.S. Application Data

(60) Division of application No. 11/220,027, filed on Sep. 6, 2005, now Pat. No. 7,531,511, which is a continuation of application No. 10/395,541, filed on Mar. 24, 2003, now abandoned, which is a continuation of application No. 09/637,471, filed on Aug. 11, 2000, now abandoned.

(60) Provisional application No. 60/148,746, filed on Aug. 13, 1999.

(51) Int. Cl.
*C07K 14/50* (2006.01)
*C07K 14/515* (2006.01)
*A61K 38/00* (2006.01)

(52) U.S. Cl. .................... 514/9.1; 514/13.3

(58) Field of Classification Search .................. None
See application file for complete search history.

(56) References Cited

U.S. PATENT DOCUMENTS

| | | |
|---|---|---|
| 4,296,100 A | 10/1981 | Franco |
| 4,378,347 A | 3/1983 | Franco |
| 4,956,455 A | 9/1990 | Esch et al. |
| 5,137,734 A | 8/1992 | Spiegelman et al. |
| 5,155,214 A | 10/1992 | Baird et al. |
| 5,155,217 A | 10/1992 | Goldfarb et al. |
| 5,238,916 A | 8/1993 | Goldfarb et al. |
| 5,244,460 A | 9/1993 | Unger et al. |
| 5,302,702 A | 4/1994 | Seddon et al. |
| 5,310,883 A | 5/1994 | Seddon et al. |
| 5,314,872 A | 5/1994 | Kato et al. |
| 5,352,589 A | 10/1994 | Bergonzoni et al. |
| 5,371,206 A | 12/1994 | Seddon et al. |
| 5,387,673 A | 2/1995 | Seddon et al. |
| 5,439,818 A | 8/1995 | Fiddes et al. |
| 5,464,774 A | 11/1995 | Baird et al. |
| 5,491,220 A | 2/1996 | Seddon et al. |
| 5,514,566 A | 5/1996 | Fiddes et al. |
| 5,604,293 A | 2/1997 | Fiddes et al. |
| 5,612,211 A | 3/1997 | Wilson et al. |
| 5,750,659 A | 5/1998 | Basilico et al. |
| 5,792,453 A | 8/1998 | Hammond et al. |
| 6,440,934 B1 | 8/2002 | Whitehouse |
| 6,451,303 B1 | 9/2002 | Whitehouse et al. |
| 7,112,560 B2 | 9/2006 | Whitehouse |
| 7,511,019 B2 | 3/2009 | Whitehouse et al. |

FOREIGN PATENT DOCUMENTS

| | | |
|---|---|---|
| EP | 0 228 449 | 7/1987 |
| EP | 0 275 204 | 7/1988 |
| EP | 0363675 | 4/1990 |
| WO | WO 86/07595 | 12/1986 |
| WO | WO 89/04832 | 6/1989 |
| WO | WO 00/13701 | 3/2000 |
| WO | WO 00/21548 | 4/2000 |
| WO | WO 00/62798 | 10/2000 |

OTHER PUBLICATIONS

Itoh et al., Dev. Dynamics 237: 18-27, 2008.*
Itoh and Ornitz., J. Biochem, 149: 121-130, 2011.* Abraham et al., "Human Basic Fibroblast Growth Factor: Nucleotide Sequence and Genomic Organizaion,"*The EMBO Journal*, 1986, pp. 2523-2528, vol. 5.
Banai et al., "Angiogenic-Induced Enhancement of Collateral Blood Flow to Ischemic Myocardium by Vascular Endothelial Growth Factor in Dogs," *Circulation*, 1994, pp. 2183-2189, vol. 89.
Battler et al., "Itracoronary Injection of Basic Fibroblast Growth Factor Enhances Angiogenesis in Infarcted Swine Myocardium," *JACC*, 1993, pp. 2001-2006, vol. 22.
Bikfalvi et al., "Biological Roles of Fibroblast Growth Factor2," *Endocrine Reviews*, 1997, pp. 26-45, vol. 18.
Bowie et al., "Deciphering the Message in Protein Sequences: Tolerance to Amino Acid Substitutions," *Science*, 1990, pp. 1306-1310, vol. 247.
Burgess et al., "The Heparin-Binding (Fibroblast) Growth Factor Family of Proteins,"*Annu. Rev. Biochem*, 1989, pp. 575-606, vol. 58.

(Continued)

*Primary Examiner* — Gyan Chandra
(74) *Attorney, Agent, or Firm* — Alston & Bird LLP

(57) ABSTRACT

The present invention has multiple aspects. In one aspect, the present invention is directed to a unit dose pharmaceutical composition comprising from about 5 ng/dose to less than 135,000 ng of an angiogenic agent, typically from 5 ng to 67,500 ng. Preferably, the angiogenic agent is FGF, more preferably it is basic FGF (FGF-2). In its second aspect, the present invention is directed to a method for inducing angiogenesis, or increasing myocardial perfusion or vascular density in a patient's heart, comprising administering directly into the myocardium in an area in need, as a single injection or a series of injections, a unit dose of an angiogenic agent. It is also within the scope of the present invention that a plurality of unit dose compositions be administered directly into the myocardium at a plurality of sites in need of angiogenesis. In another aspect, the present invention is directed to a method for treating a patient for coronary artery disease, comprising administering directly into the myocardium in an area of need of angiogenesis in said patient, a unit dose (i.e., from about 5 ng to less than 135,000 ng) of an angiogenic agent. In yet another aspect, the present invention is directed to a method for treating a patient for a myocardial infarction, comprising administering directly into the myocardium in an area in need of angiogenesis in said patient, a unit dose (i.e., from about 5 ng to less than 135,000 ng) of an angiogenic agent.

4 Claims, 11 Drawing Sheets

OTHER PUBLICATIONS

Clements et al., "Activation of Fibroblast Growth Factor (FGF) Receptors by Recombinant Human FGF-5," *Oncogene*, 1993, pp. 1311-1316, vol. 8.

Coulier et al., "Putative Structure of the *FGF6* Gene Product and Role of the Signal Peptide," *Oncogene*, 1991, pp. 1437-1444, vol. 6.

Folkman, "Angiogenic Therapy of the Human Heart," *Circulation*, 1998, pp. 628-629, vol. 97.

Giordano et al., "Reduced Myocardial Ischemia after Recombinant Adenovirus MediatedIn-Vivo Fibroblast Growth Factor-5 Gene Transfer," *J. Invest. Med.*, 1995, pp. 278A, vol. 3.

Giordano et al., "Intracoronary Gene Transfer of Fibroblast Growth Factor-5 Increases Blood Flow and Contractile Function in an Ischemic Region of the Heart,"*Nature Medicine*, 1996, pp. 534-539, vol. 2.

Guzman et al., "Efficient Gene Transfer into Myocardium by Direct Injection of Adenovirus Vectors," *Circulation Research*, 1993, pp. 1202-1207, vol. 73.

Harada et al., "Basic Fibroblast Growth Factor Improves Myocardial Function in Chronically Ischemic Porcine Hearts," *J. Clin. Invest.*, 1994, pp. 623-630, vol. 94.

Isner, "The Role of Angiogenic Cytokines in Cardiovascular Disease,"*Clinical Immunology and Immunopathology*, 1996, pp. S82-S91, vol. 80.

Kirschner et al., "Basic Fibroblast Growth Factor Protects Against Excitotoxicity and Chemical Hypoxia in Both Neonatal and Adult Rats," *J. Cerebral Blood Flow and Metabolism*, 1995, pp. 619-623, vol. 15.

Klagsbrun, "Angiogenic Factors: Regulators of Blood SupplySide Biology," *The New Biologist*, 1991, pp. 745-749, vol. 3.

Laham et al., "A Single Intrapericardial Dose of Basic Fibroblast Growth Factor Induces Functional Angiogenesis in a Porcine Model of Chronic Myocardial Ischemia,"*Circulation*, 1998, pp. 1794, vol. 98.

Laham et al., "Local Perivascular Basic Fibroblast Growth Factor (bFGF) Treatment in Patients with Ischemic Heart Disease,"*J. Am. Coll. Cardiol.*, 1998, pp. 394A, vol. 31.

Laham et al., "Intrapericardial Delivery of Fibroblast Growth Factor-2 Induces Neovascularization in a Porcine Model of Chronic Myocardial Ischemia," *The Journal of Pharmacology and Experimental Therapeutics*, 2000, pp. 795-802, vol. 292.

Landau et al., "Intrapericardial Basic Fibroblast Growth Factor Induces Myocardial Angiogenesis in a Rabbit Model of Chronic Ischemia,"*American Heart Journal*, 1995, pp. 924-931, vol. 129.

Lazarous et al., "Comparative Effects of Basic Fibroblast Growth Factor and Vascular Endothelial Growth Factor on Coronary Collateral Development and the Arterial Response to Injury,"*Circulation*, 1996, pp. 1075-1082, vol. 94.

Lazarous et al., "Effects of Chronic Systemic Administration of Basic Fibroblast Growth Factor on Collateral Development in the Canine Heart,"*Circulation*, 1995, pp. 145-153, vol. 91.

Lipton et al., "Acidic Fibroblast Growth Factor Enhances Regeneration of Processes by Postnatal Mammalian Retinal Ganglion Cells in Culture,"*Proc. Natl. Acad. Sci.,*, 1988, pp. 2388-2392, vol. 85.

Lopez et al., "Local Perivascular Administration of Basic Fibroblast Growth Factor: Drug Deliveryand Toxicological Evaluation," *Drug and Metabolism and Disposition*, 1996, pp. 922-924, vol. 24.

Magovern et al., "Direct in vivo Gene Transfer to Canine Myocardium Using a Replication-Deficient Adenovirus Vector,"*Ann. Thorac. Surg.*, 1996, pp. 425-434, vol. 62.

Mathieu et al., "Receptor Binding and Mitogenic Properties of Mouse Fibroblast Growth Factor 3,"*The Journal of Biological Chemistry*, 1995, pp. 24197-24203, vol. 270.

Miyamoto et al., "Molecular Cloning of a Novel Cytokine cDNA Encoding the Ninth Member of the Fibroblast Growth Factor Family, Which Has a Unique Secretion Property,"*Molecular and Cellular Biology*, 1993, pp. 4251-4259, vol. 13.

Miyataka et al., "Basic Fibroblast Growth Factor Increased Regional Myocardial Blood Flow and Limited Infarct Size of Acutely Infarcted Myocardium in Dogs," *Angiology*, 1998, pp. 381-390, vol. 49.

Nabel et al., "Recombinant Fibroblast Growth Factor-1 Promotes Intimal Hyperplasia and Angiogenesis in Arteries In Vivo," *Nature*, 1993, pp. 844-846, vol. 362.

Ornitz et al., "Receptor Specificity of the Fibroblast Growth Factor Family," *J. Biol. Chem.*, 1996, pp. 15292-15297, vol. 271.

Rakusan, "Coronary Angiogenesis," *Annals New York Academy of Sciences*, 1995, pp. 257-265, vol. 752.

Rubin et al., "Purification and Characterization of a Newly Identified Growth Factor Specific for Epithelial Cells," *Proc. Natl. Acad. Sci.*, 1989, pp. 802-806, vol. 86.

Schubert et al., "Multiple Influences of a Heparin-Binding Growth Factor on Neuronal Development," *The Journal of Cell Biology*, 1987, pp. 635-643, vol. 104.

Schumacher et al., "Induction of Neoangiogenesis in Ischemic Myocardium by Human Growth Factors," *Circulation*, 1997, pp. 645-650, vol. 97.

Schumacher et al., "The Stimulation of Neoangiogenesis in the Ischemic Human Heart by the Growth Factor FGF: First Clinical Results," *Journal of Cardiovascular Surgery*, 1998, pp. 783-789, vol. 39.

Schumacher et al., "The Stimulation of Neo-Angiogenesis in the Ischemic Heart by the Human Growth Factor FGF," *Journal of Cardiovascular Surgery*, 1998, pp. 445-453, vol. 39.

Sellke et al., "Basic FGF Enhances Endothelium-Dependent Relaxation of the Collateral-Perfused Coronary Microcirculation," *The American Physiological Society*, 1994, pp. H1303-H1311, vol. 267.

Sellke et al., "Enhanced Microvascular Relaxations to VEGF and bFGF in Chronically Ischemic Porcine Myocardium," *Am. J. Physiol.*, 1996, pp. H713-H720, vol. 271.

Sellke et al., "Angiogenesis Induced by Acidic Fibroblast Growth Factor as an Alternative Method of Revascularization for Chronic Myocardial Ischemia,"*Surgery*, 1996, 82-188, vol. 120.

Sellke et al., "Therapeutic Angiogenesis with Basic Fibroblast Growth Factor: Technique and Early Result" *The Society of Thoracic Surgeons*, 1998, pp. 1540-1544, vol. 65.

Shou et al., "Effect of Basic Fibroblast Growth Factor on Myocardial Angiogenesis in Dogs with Mature Collateral Vessels," *JACC*, 1997, pp. 1102-1106, vol. 29.

Slavin, "Fibroblast Growth Factors: At the Heart of Angiogenesis,"*Cell Biology International*, 1995, pp. 431-444, vol. 19.

Uchida et al., "Angiogenic Therapy of Acute Myocardial Infarction by Intrapericardial Injection of Basic Fibroblast Growth Factor and Heparin Sulfate: An Experimental Study," *American Heart Journal*, 1995, pp. 1182-1188, vol. 130.

Unger et al., "Basic Fibroblast Growth Factor Enhances Myocardial Collateral Flow in a Canine Model,"*Am. J. Physiol*, 1994, pp. H1588-H1595, vol. 266.

Valles et al., "Acidic Fibroblast Growth Factor is a Modulator of Epithelial Plasticity in a Rat Bladder Carcinoma Cell Line," *Proc. Natl. Acad. Sci.*, 1990, pp. 1124-1128, vol. 87.

Wang et al., "A Phenylalanine Residue at Segment D3-S6 in Nav1.4 Voltage-Gated Na+ Channels is Critical for Pyrethroid Action," *Molecular Pharmacology*, 2001, pp. 620-628, vol. 60.

Watanabe et al., "Effect of Basic Fibroblast Growth Factor on Angiogenesis in the Infarcted Porcine Heart," *Basic Res. Cardiol*, 1998, pp. 30-37, vol. 93.

Wells, "Addivity of Mutational Effects in Proteins,"*Biochemistry*, 1990, pp. 8509-8517, vol. 29.

Yanagisawa-Miwa et al., "Salvage of Infarcted Myocardium by Angiogenic Action of Basic Fibroblast Growth Factor," *Science*, 1992, pp. 1401-1403, vol. 257.

Hasegawa et al., "Basic Fibroblast Growth Factor Increases Regional Myocardial Blood Flow and Salvages Myocardium in the Infarct Border Zone in a Rabbit Model of Acute Myocardial Infarction," *The Journal of Vascular Diseases*, 1999, pp. 487-495, vol. 50, No. 6.

\* cited by examiner

SEQUENCE LISTING

<160> NUMBER OF SEQ ID NOS: 6

<210> SEQ ID NO 1
<211> LENGTH: 442
<212> TYPE: DNA
<213> ORGANISM: cDNA BOVINE FGF-2
<220> FEATURE:
<221> NAME/KEY: CDS
<222> LOCATION: (1)..(438)

<400> SEQUENCE: 1

```
cca gcc cta cca gaa gat ggg ggg tcc ggg gcc ttc cca cca ggg cac      48
Pro Ala Leu Pro Glu Asp Gly Gly Ser Gly Ala Phe Pro Pro Gly His
1               5                   10                  15 ttc aaa gat cca aaa cga cta tat tgt aaa aac ggg ggg ttc ttc cta      96
Phe Lys Asp Pro Lys Arg Leu Tyr Cys Lys Asn Gly Gly Phe Phe Leu
            20                  25                  30 cga atc cac cca gat ggg cga gta gat ggg gta cga gaa aaa tcc gat     144
Arg Ile His Pro Asp Gly Arg Val Asp Gly Val Arg Glu Lys Ser Asp
        35                  40                  45 cca cac atc aaa cta caa cta caa gcc gaa gaa cga ggg gta gta tcc     192
Pro His Ile Lys Leu Gln Leu Gln Ala Glu Glu Arg Gly Val Val Ser
    50                  55                  60 atc aaa ggg gta tgt gcc aac cga tat cta gcc atg aaa gaa gat ggg     240
Ile Lys Gly Val Cys Ala Asn Arg Tyr Leu Ala Met Lys Glu Asp Gly
65                  70                  75                  80
```

```
cga cta cta gcc tcc aaa tgt gta acc gat gaa tgt ttc ttc ttc gaa    288
Arg Leu Leu Ala Ser Lys Cys Val Thr Asp Glu Cys Phe Phe Phe Glu
            85                  90                  95 cga cta gaa tcc aac aac tat aac acc tat cga tcc cga aaa tat tcc    336
Arg Leu Glu Ser Asn Asn Tyr Asn Thr Tyr Arg Ser Arg Lys Tyr Ser
            100                 105                 110 tcc tgg tat gta gcc cta aaa cga acc ggg caa tat aaa cta ggg cca    384
Ser Trp Tyr Val Ala Leu Lys Arg Thr Gly Gln Tyr Lys Leu Gly Pro
            115                 120                 125 aaa acc ggg cca ggg caa aaa gcc atc cta ttc cta cca atg tcc gcc    432
Lys Thr Gly Pro Gly Gln Lys Ala Ile Leu Phe Leu Pro Met Ser Ala
            130                 135                 140 aaa tcc taag                                                       442
Lys Ser
145

<210> SEQ ID NO 2
<211> LENGTH: 146
<212> TYPE: PRT
<213> ORGANISM: cDNA BOVINE FGF-2

<400> SEQUENCE: 2

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
            85                  90                  95

Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Pro
            115                 120                 125

Lys Thr Gly Pro Gly Gln Lys Ala Ile Leu Phe Leu Pro Met Ser Ala
            130                 135                 140

Lys Ser
145

<210> SEQ ID NO 3
<211> LENGTH: 9
<212> TYPE: PRT
<213> ORGANISM: bovis bovinus

<400> SEQUENCE: 3

Met Ala Ala Gly Ser Ile Thr Thr Leu
1               5

<210> SEQ ID NO 4
<211> LENGTH: 489
<212> TYPE: DNA
<213> ORGANISM: cDNA human FGF-2
<220> FEATURE:
<221> NAME/KEY: CDS
<222> LOCATION: (1)..(465)

<400> SEQUENCE: 4
```

```
atg gca gcc ggg agc atc acc acg ctg ccc gcc ttg ccc gag gat ggc    48
Met Ala Ala Gly Ser Ile Thr Thr Leu Pro Ala Leu Pro Glu Asp Gly
1               5                   10                  15 ggc agc ggc gcc ttc ccg ccc ggc cac ttc aag gac ccc aag cgg ctg    96
Gly Ser Gly Ala Phe Pro Pro Gly His Phe Lys Asp Pro Lys Arg Leu
            20                  25                  30 tac tgc aaa aac ggg ggc ttc ttc ctg cgc atc cac ccc gac ggc cga    144
Tyr Cys Lys Asn Gly Gly Phe Phe Leu Arg Ile His Pro Asp Gly Arg
        35                  40                  45 gtt gac ggg gtc cgg gag aag agc gac cct cac atc aag cta caa ctt    192
Val Asp Gly Val Arg Glu Lys Ser Asp Pro His Ile Lys Leu Gln Leu
    50                  55                  60 caa gca gaa gag aga gga gtt gtg tct atc aaa gga gtg tgt gct aac    240
Gln Ala Glu Glu Arg Gly Val Val Ser Ile Lys Gly Val Cys Ala Asn
65                  70                  75                  80 cgt tac ctg gct atg aag gaa gat gga aga tta ctg gct tct aaa tgt    288
Arg Tyr Leu Ala Met Lys Glu Asp Gly Arg Leu Leu Ala Ser Lys Cys
                85                  90                  95 gtt acg gat gag tgt ttc ttt ttt gaa cga ttg gaa tct aat aac tac    336
Val Thr Asp Glu Cys Phe Phe Phe Glu Arg Leu Glu Ser Asn Asn Tyr
            100                 105                 110 aat act tac cgg tca agg aaa tac acc agt tgg tat gtg gca ttg aaa    384
Asn Thr Tyr Arg Ser Arg Lys Tyr Thr Ser Trp Tyr Val Ala Leu Lys
        115                 120                 125 cga act ggg cag tat aaa ctt gga tcc aaa aca gga cct ggg cag aaa    432
Arg Thr Gly Gln Tyr Lys Leu Gly Ser Lys Thr Gly Pro Gly Gln Lys
    130                 135                 140 gct ata ctt ttt ctt cca atg tct gct aag agc tgatttaat ggccacatct   485
Ala Ile Leu Phe Leu Pro Met Ser Ala Lys Ser
145                 150                 155 aatc                                                                489
```

<210> SEQ ID NO 5
<211> LENGTH: 155
<212> TYPE: PRT
<213> ORGANISM: cDNA human FGF-2

<400> SEQUENCE: 5

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

```
<210> SEQ ID NO 6
<211> LENGTH: 146
<212> TYPE: PRT
<213> ORGANISM: Mature Human FGF-2

<400> SEQUENCE: 6

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145
```

METHOD FOR INDUCING ANGIOGENESIS IN A HEART OF A PATIENT

CROSS-REFERENCE TO RELATED APPLICATIONS

This application is a divisional of U.S. application Ser. No. 11/220,027, filed Sep. 6, 2005, now U.S. Pat. No. 7,531,511, which is a continuation of U.S. application Ser. No. 10/395,541, filed Mar. 24, 2003, now abandoned, which is a continuation of U.S. application Ser. No. 09/637,471, filed Aug. 11, 2000, now abandoned, which claims the benefit of U.S. Provisional Application No. 60/148,746, filed Aug. 13, 1999, the contents of which are herein incorporated by reference in their entirety.

FIELD OF THE INVENTION

The present invention is directed to a dose, including an ultra-low dose, of an angiogenic factor, such as a fibroblast growth factor (FGF), platelet derived growth factor or a vascular endothelial growth factor, or an angiogenically active fragment or mutein thereof, and to a mode of administering the dose to obtain improved myocardial blood flow. The present invention is also directed to a pharmaceutical composition comprising the dose of angiogenic factor and to a method for administering the pharmaceutical composition to a heart, preferably a human heart, to improve myocardial function, blood flow, perfusion and/or vascular density. The present invention is useful because the disclosed dose, pharmaceutical composition and method for its administration provide an alternative or adjunct to surgical intervention for the treatment of coronary artery disease (CAD) and/or further provide a method for reducing post myocardial infarct (MI) injury in humans. Finally, the present invention includes a method for determining whether the administered angiogenic agent is having a therapeutic effect on the target tissues by assaying for a surrogate marker.

BACKGROUND OF THE INVENTION

Coronary artery disease (atherosclerosis) is a progressive disease in humans wherein one or more coronary arteries gradually become occluded through the buildup of plaque. The coronary arteries of patients having this disease are often treated by balloon angioplasty or the insertion of stents to prop open the partially occluded arteries. Ultimately, these patients are required to undergo coronary artery bypass surgery at great expense and risk. It would be desirable to provide such patients with a treatment that would enhance coronary blood flow so as to preclude the need to undergo bypass surgery or angioplasty.

An even more critical situation arises in humans when a patient suffers a myocardial infarction, wherein one or more coronary arteries or arterioles becomes completely occluded, such as by a clot. There is an immediate need to regain circulation to the portion of the myocardium served by the occluded artery or arteriole. If the lost coronary circulation is restored within hours of the onset of the infarction, much of the damage to the myocardium that is downstream from the occlusion can be prevented. The clot-dissolving drugs, such as tissue plasminogen activator (tPA), streptokinase, and urokinase, have been proven to be useful in this instance. However, as an adjunct to the clot dissolving drugs, it would also be desirable to also obtain collateral circulation to the damaged or occluded myocardium by angiogenesis.

Accordingly, it is an object of the present invention to provide a dose of an angiogenic agent and a mode of its administration to a human heart in need of angiogenesis that provides the human heart with cardiac angiogenesis while minimizing the risk of inducing angiogenesis elsewhere in the body, particularly in an undetected tumor. More particularly, it is a further object of the present invention to provide a therapeutic dose of an angiogenic factor and a mode of its administration to a human patient that provides the desired property of cardiac angiogenesis, such as during the treatment of coronary artery disease and/or post acute myocardial infarction, while minimizing the possibility of an adverse angiogenic effect occurring elsewhere in the body.

Angiogenic agents include the platelet derived growth factors (PDGF), vascular endothelial growth factor-A (VEGF-A), transforming growth factor-$\beta1$ (TGF-$\beta1$) and the fibroblast growth factors. The fibroblast growth factors (FGF) are a family of at least eighteen structurally related polypeptides (named FGF-1 to FGF-18) that are characterized by a high degree of affinity for proteoglycans, such as heparin. The various FGF molecules range in size from 15-23 kD, and exhibit a broad range of biological activities in normal and malignant conditions including nerve cell adhesion and differentiation [Schubert et al., *J. Cell Biol.* 104:635-643 (1987)]; wound healing [U.S. Pat. No. 5,439,818 (Fiddes)]; as mitogens toward many mesodermal and ectodermal cell types, as trophic factors, as differentiation inducing or inhibiting factors [Clements, et al., *Oncogene* 8:1311-1316 (1993)]; and as an angiogenic factor [Harada, *J. Clin. Invest.*, 94:623-630 (1994)]. Thus, the FGF family is a family of pluripotent growth factors that stimulate to varying extents fibroblasts, smooth muscle cells, epithelial cells and neuronal cells.

When any angiogenic agent (or factor) is released by normal tissues, such as in fetal development or wound healing, it is subject to temporal and spatial controls. However, many angiogenic agents are also oncogenes. Thus, in the absence of temporal and spatial controls, they have the potential to stimulate tumor growth by providing angiogenesis. Accordingly, before any angiogenic agent is used as a medicament in human patients, consideration must be given to minimizing its angiogenic effect on undetected tumors. As a result, it is an object of the present invention to provide a dosage of angiogenic agent and a mode of its administration that would provide localized angiogenesis in a targeted organ but which would minimize the risk of enhancing angiogenesis in an undetected tumor elsewhere in the body.

Many of the angiogenic agents (e.g., PDGF, VEGF-A or FGF) have been isolated and administered to various animal models of myocardial ischemia with varying and often times opposite results. According to Battler et al., "the canine model of myocardial ischemia has been criticized because of the abundance of naturally occurring collateral circulation, as opposed to the porcine model, which 'excels' in its relative paucity of natural collateral circulation and its resemblance to the human coronary circulation." Battler et al., *"Intracoronary Injection of Basic Fibroblast Growth Factor Enhances Angiogenesis in Infarcted Swine Myocardium,"* JACC, 22(7): 2001-6 (December 1993) at page 2002, col. 1. Thus, those of ordinary skill in the art considered the porcine heart to be the model that excelled most in its resemblance to the human heart. Further, Battler points out that "the dosage and mode of administration of bFGF [i.e., bovine FGF-2] may have profound implications for the biologic effect achieved." Battler, et al., at page 2005, col. 1. Thus, it is a further object of this invention to provide a dosage and a mode of administration of an angiogenic agent that would provide for the safe and efficacious treatment of CAD and/or post MI injury in a human patient. More generally, it is an object of the present invention to provide a pharmaceutical composition and method for administration that would induce angiogenesis in a human heart while minimizing the risk of angiogenesis elsewhere in the body.

The various studies to date on angiogenic agents have administered dosages of the angiogenic agent in the range of 10 µg to 1500 µg. For example, Yanagisawa-Miwa, et al., "*Salvage of Infarcted Myocardium by Angiogenesic Action of Basic Fibroblast Growth Factor,*" Science, 257:1401-1403 (1992), disclose infusing two 10 µg doses of human recombinant basic FGF (hrFGF-2) in 10 ml of saline over a one minute period into the left circumflex coronary artery (LCX) of dogs after inducing a myocardial infarction by inserting a thrombus into the adjacent left ascending coronary artery (LAD). Yanagisawa-Miwa further discloses that as a result of the intracoronary administration of a total of 20 µg of hrFGF-2 in this canine model, "vessel formation occurred within 1 week after administration of bFGF." Yanagisawa-Miwa at page 1403. Banai et al., "*Angiogenic-Induced Enhancement of Collateral Blood Flow to Ischemic Myocardium by Vascular Endothelial Growth Factor in Dogs,*" Circulation, 89(5):2183-2189 (May 1994), discloses successfully inducing coronary angiogenesis (i.e., a 40% increase in collateral blood flow and an 89% increase in the numerical density of intramyocardial distribution vessels) in dogs by administering 45 µg of human recombinant VEGF/day for 5 days/week for 4 weeks to the distal left circumflex artery (LCx) of dogs whose proximal LCx was constricted before the first takeoff branch with an ameroid constrictor and wherein a hydraulic balloon occluder was placed immediately distal to the encircling ameroid. In a similar study, Unger, et al., "*Basic fibroblast growth factor enhances myocardial collateral flow in a canine model,*" Am. J. Physiol., 266 (Heart Circ. Physiol. 35): H1588-H1595 (1994), disclose enhancing collateral blood flow (i.e., final collateral to normal zone (CZ/NZ) blood flow ratios of 0.49 and 0.35 in the treated and untreated groups, respectively) in dogs by administering a daily bolus of 110 µg of human recombinant basic FGF (the 155 residue form) for 9 days to the distal left circumflex artery (LCx) of dogs whose proximal LCx was constricted before the first takeoff branch with an ameroid constrictor and wherein a hydraulic balloon occluder was placed immediately distal to the encircling ameroid. However, in the above study, Unger was not able to show that his method or dosage induced angiogenesis. Making any assessment based on collateral blood flow more difficult, Unger also discloses that administration of basic FGF causes an acute vasodilatory effect, reducing blood pressure and increasing coronary blood flow. Unger (1994) at page H1590, col. 2 and at page H1592, col. 2.

In an earlier study, Unger, et al., "*A model to assess interventions to improve collateral blood flow: continuous administration of agents into the left coronary artery in dogs,*" Cardiovascular Res., 27:785-791 (1993), Unger discloses the continuous infusion for four (4) weeks of 30 µg/hr recombinant acidic FGF (i.e., FGF-1) in the presence of 30 IU/hr heparin into the proximal end of the left circumflex artery (LCx) of a dog after constricting the artery for four weeks with an ameroid constrictor, followed by double ligation of the artery and insertion of a catheter for infusing the FGF-1 into the proximal stub of the ligated LCx. Unger (1993) at page 785. Notwithstanding that a total cumulative dose of 10 mg of acidic FGF was infused into the coronary artery of each dog. Unger reported that in this model, "acidic FGF had no demonstratable effect on collateral blood flow . . ." Unger (1993) at page 785 (Abstract), and at page 790.

Harada, et al., "*Basic Fibroblast Growth Factor Improves Myocardial Function in Chronically Ischemic Porcine Hearts,*" J. Clin. Invest., 94:623-630 (August 1994), disclose enhancing coronary blood flow and reduction in infarct size in a gradual coronary occlusion model in Yorkshire pigs by extraluminal (periadvential) administration of 8 µg of basic FGF in the form of 4-5 capsules having 1 µg/capsule of basic FGF that are positioned on the proximal left anterior descending artery (LAD) and both proximal and distal to an ameroid constrictor placed on the proximal end of the left circumflex artery (LCx) before the first takeoff branch. Although an express object of Harada's experiment was to "alleviate chronic myocardial ischemia by stimulating angiogenesis" [Harada at page 628], Harada was not able to show angiogenesis. Moreover, Harada concluded that "[I]t is not clear what is the optimal dose of bFGF or the length or route of administration." Harada at page 629. Separately, Landau et al., "*Intrapericardial basic fibroblast growth factor induces myocardial angiogenesis in a rabbit model of chronic ischemia,*" Am. Heart Journal, 129:924-931 (1995), discloses that administering 180 ng/day of human recombinant basic FGF (154 residues) into the pericardial space of 2.0-4.3 kg rabbits for 7-28 days, enhances new epicardial small-vessel growth, and that the effect is enhanced by left ventricular hypertrophy. The dosage of basic FGF utilized in Landau, when scaled to the size of a 70 kg man, would correspond to 2.9 µg/day for 7-28 days, or a total dose of basic FGF of 20.3 µg-81.2 µg. Lopez et al., "*Angiogenic potential of perivascularly delivered aFGF in a porcine model of chronic myocardial ischemia,*" Am. J. Physiol. 274 (Heart Circ. Physiol. 43): H930-H936 (1998), discloses improving myocardial flow and regional and global left ventricular function in Yorkshire pigs by perivascular delivery of 14 µg of a recombinant human aFGF mutein (i.e., Ser-117 aFGF, wherein Ser replaces Cys) that is diffusely distributed in a porous ethylene vinyl acetate (EVA) polymer that is secured with sutures over the proximal left circumflex artery. Lopez reports that the perivascularly delivered aFGF improved blood flow in the compromised region of the heart in animals both "at rest" and "during rapid pacing." Lopez at page H934, col. 2. However, Lopez was unable to directly attribute the increased blood flow to angiogenesis, citing other possible sources, such as "vasodilation" or "improvements in vascular circulation."

Finally, U.S. Pat. No. 4,296,100, which issued to Franco on Oct. 20, 1981, discloses a method for treating a myocardial infarction in patients by administering 10 mg to 1 g of 90% pure bovine FGF (pituitary extract) per 100 g of heart tissue as a one-time treatment immediately following infarct. According to Franco, "[a]t least 10 micrograms/100 grams heart is used to achieve the effect desired." Franco at col. 1, lines 62-64. Franco discloses that the FGF is administered to the heart by a variety of modes, including direct injections into the heart, intravenous injection, subcutaneous injection, intramuscular injection and oral ingestion. Franco at col. 2, lines 63-69. Franco also discloses that his method was able to reduce infarct size (area of scarring or of permanent damage) to one quarter of that in the control. Franco at Table III. According to Franco, the function of the FGF was to "increase blood flow for a sustained period of time after myocardial infarction." Franco at col. 1, lines 42-43. However, the acute affect of any FGF administration is vasodilation, which inherently increases coronary blood flow. Franco expressly discloses that a histological study "did not show any significant increase in capillary areas in the hearts" as a result of such treatment with 10 µg to 1 g of FGF per 100 g of heart. Franco at col. 4, lines 13-17. Moreover, Franco did not address the issue of whether administering such large doses of FGF would have angiogenic effects in any undiscovered tumors in the body.

Thus, it is an object of the present invention to provide a dosage of an angiogenic agent and a method of administering one or more dosages of the angiogenic agent to a patient in an amount that is effective to induce angiogenesis to an area of the heart in need of angiogenesis. It is a further object of this application to provide a dosage and a method for delivering an angiogenic agent that would provide for a therapeutic effect, including angiogenesis at the target site, while reducing the risk of inducing angiogenesis at an unwanted site elsewhere in the body.

The above-described references and all other references cited herein are expressly incorporated herein in their entirety.

SUMMARY OF THE INVENTION

The Applicants have unexpectedly discovered that certain dosages of an angiogenic agent, when injected into the myocardium downstream from a coronary occlusion, provided that portion of the myocardium with a therapeutic response as reflected by an increase in resting regional perfusion, an improvement in regional cardiac function, and increased vascularity. In particular, the Applicants discovered that a unit dose (i.e., from about 5 ng/dose to less than 135,000 ng/dose) of an angiogenic agent, when administered directly into the myocardium as a single injection or as a series of injections in the area of need, induced coronary angiogenesis in the myocardium in the area of administration but became sufficiently diluted elsewhere in the body to minimize any risk of inducing angiogenesis. When the unit dose of angiogenic agent of the present invention is administered as a series of injections, the series of injections are administered as a single procedure on the same day or as a series of injections on successive or alternating days as needed. However, the cumulative amount of the dosage of the angiogenic agent that is administered is typically from about 5 ng to less than 135,000 ng (135 µg), more typically from 5 ng to 67,500 ng (67.5 µg). Thus, in one aspect, the present invention is directed to a unit dose pharmaceutical composition ("pharmaceutical composition") comprising from about 5 ng to less than 135,000 ng (preferably from 5 ng to 67,500 ng) of an angiogenic agent in a pharmaceutically acceptable carrier. In another aspect, the present invention is directed to a unit dose pharmaceutical composition ("unit dose composition") comprising from about 5 ng to less than 135,000 ng (preferably from 5 ng to 67,500 ng) of an angiogenic agent in a pharmaceutically acceptable carrier.

In yet another aspect, the present invention is directed to method for inducing angiogenesis, or increasing regional perfusion, or increasing cardiac function, or increasing vascular density in the myocardium of a patient in need of such treatment, comprising injecting a unit dosage of an angiogenic agent, as a single injection or as a series of injections, directly into an area of myocardium in need of such angiogenesis, or increased regional perfusion, or increased cardiac function, or increased vascular density, respectively. It is also within the scope of the above-described method that the step of injecting the unit dosage be performed as a single injection, or preferably as a series of injections on the same day. Regardless of whether the above method is performed using a single injection or a series of injections, the cumulative amount of the angiogenic agent that is injected into the area of myocardium in need of angiogenesis during the one or more injections is from about 5 ng to less than 135,000 ng (135 µg).

It is also appropriate to express the unit dose of the present invention as µg of angiogenic agent per kilogram (kg) of patient weight. When so expressed, a dose of angiogenic agent for intramyocardial (IMc) injection in accordance with the present invention ranges from about 0.06 µg angiogenic agent to about 10.0 µg angiogenic agent per kg of patient weight (hereinafter "µg/kg"). More typically, the dose of angiogenic agent ranges from 0.06 µg/kg to 6.0 µg/kg. However, because the angiogenic agent is being injected directly into the myocardium of the patient in the method of the present invention, the typical dilutional effects on dosage associated with patient body weight are minimal, particularly when compared to systemic or intracoronory administration of the same amount of angiogenic agent.

Two diseases where angiogenesis increased regional perfusion, and increased coronary vascularity are desirable are coronary artery disease (CAD) and myocardial infarction (MI). Thus, in another aspect, the present invention is also directed to a method for treating a patient for coronary artery disease (CAD) comprising injecting a unit dosage of an angiogenic agent, as a single injection or as a series of injections, directly into a portion of the myocardium manifesting symptoms of CAD, the unit dosage containing an amount of the angiogenic agent (about 5 ng to less than 135,000 ng) that is effective to induce angiogenesis, or increase regional perfusion, or increase myocardial function by DSE at peak stress, or increase vascularity in the area of myocardium manifesting said symptoms. In another aspect, the present invention is directed to a method for treating a patient for a myocardial infarction (MI) comprising injecting a unit dosage of an angiogenic agent, as a single injection or as a series of injections, directly into an area of myocardium manifesting symptoms of coronary insufficiency as a result of said MI. In the above-described method, the unit dose of angiogenic agent that is effective in treating said myocardial infarction is about 5 ng to less than 135,000 ng of angiogenic agent/unit dose, more typically 5 ng to 67,500 ng of angiogenic agent/unit dose.

Although the unit dose is typically injected into the myocardium on a single day, it is within the scope of the present invention that the step of injecting the unit dose of angiogenic agent be performed or repeated on successive or alternating days or weekly or monthly as needed. Regardless of whether the above method is repeated, the cumulative amount of the angiogenic agent that is injected into the area of myocardium in need of angiogenesis during any single intervention is from about 5 ng to less than 135,000 ng of said angiogenic agent.

A suitable angiogenic agent for use in the unit dose or pharmaceutical composition of the present invention is selected from the group consisting of a platelet-derived growth factor (PDGF), vascular endothelial growth factor (VEGF-A), VEGF-B, VEGF-D, transforming growth factor-β (TGF-β1), fibroblast growth factor (FGF), or an angiogenically active fragment or mutein thereof. Preferably, the angiogenic agent is VEGF-A, VEGF-D, an FGF, or an angiogenically active fragment or mutein thereof. More preferably, the angiogenic agent is an FGF, such as FGF-1, FGF-2 or FGF-5, or an angiogenically active fragment or mutein thereof. Most preferably, the angiogenic agent is FGF-2, or an angiogenically active fragment or mutein thereof.

The duration of the therapeutic effects provided by the method of the present invention is wholly unexpected. In particular, when a single unit dose of 0.06 µg/kg (1,350 ng total dose) of recombinant bovine FGF-2 (SEQ ID NO: 2) was administered by injection directly to the myocardium of a miniswine having 90% occlusion of the left circumflex coronary artery (i.e., providing a model of a hibernating myocardium), improvements were seen in the resting mean blood flow (MBF), the wall motion score index (WMSI), vascular perfusion, myocardial function, and vascular density in the hibernating myocardial tissue, which continued for as far out as the six (6) month measurement period. By way of example, the resting MBF increased from a baseline of 64±0.04% of non-ischemic septal flow to 71±0.05%, p<0.05 vs baseline at one month post-treatment and to 76±0.06, p<0.05 vs baseline at three months post-treatment. At six months post-treatment, the resting MBF increased from 61.3±4.4% of non-ischemic septal flow at baseline to 82.8±3.1%. In another test that is accepted as a measure of contractile reserve, the wall motion score index (WMSI) measured at rest for the LCx region (after 90% stenosis of the LCx) improved from 2.4±0.2 to 2.2±0.2 (p=0.08 vs baseline) at 6 months post-treatment. Similarly, the wall motion score index (WMSI) measured at peak stress for the LCx region (after 90% stenosis of the LCx) improved significantly, decreasing from 2.2±0.4 to 1.8±0.3 (p=0.05 vs baseline) at 6 months post-treatment. These decreases in the wall motion score index are consistent with a reduction in ischemia. In contrast, the patients (miniswine) that were treated with the vehicle for the angiogenic agent exhibited no significant change in resting MBF, and no significant change in their resting or stress WMSI at any time during the six-month post-treatment period.

In addition, after intramyocardial (IMc) injection of a single unit dose of FGF-2 (0.06 µg/kg, i.e., 1.35 µg) in the above-described pig model of a hibernating myocardium, normalized perfusion, which is reported as % change in perfusion, continued to increase throughout the measurement period from 18% to 38% at 3 and 6 months, respectively, compared to increases of 6% and 13% at 3 and 6 months, respectively for saline. See FIG. 4. When three different embodiments of the unit dose of the present invention, i.e., a unit dose containing 0.06 µg/kg (1.35 µg) of rFGF-2 (SEQ ID NO: 2) "low" dose; a unit dose containing 0.6 µg/kg (13.5 µg) of rFGF-2 (SEQ ID NO: 2) "mid" dose; a unit dose containing 6.0 µg/kg (135 µg) of rFGF-2 (SEQ ID NO: 2) "high" dose, were injected IMc into the pig model of the hibernating myocardium (90% occlusion of the LCx) and compared to intracoronary (IC) injection of the "mid" dose in the ameroid model (100% occlusion of the LCx), all IMc injections produced a normalized perfusion at 3 months that was superior to that produced by IC injection. FIGS. 7 and 8. Surprisingly, the mid dose resulted in 10% greater normalized perfusion than that produced by either the low dose or the high dose at three months post-dosing. FIG. 7.

Myocardial function, as measured by a dolbutamine stress echocardiogram (DSE), showed statistically significant increases in myocardial function (lower number) at 3 and 6 months after injection of each of three different unit doses of the present invention (low, medium and high) into the pig model of the hibernating myocardium, compared to injection of placebo and IC injection of the "mid" dose in the ameroid pig model. See FIGS. 5 and 11. Injection of a single unit dose of FGF-2 (1.35 µg) IMc into the pig model of the hibernating myocardium produced a statistically significant (p<0.05) increase in vascularity of the treated hibernating myocardium at 6 months post dosing, as measured by the number of capillaries (44,000) in a fixed volume of the FGF-2 treated ischemic myocardium versus the number of capillaries (17, 000) in the same fixed volume of saline treated myocardium. See FIG. 6.

Finally, Western blot analysis of myocardial tissue from the ischemic regions of the myocardium treated with FGF-2 IC or IMc, indicated that there was a significant upregulation of VEGF (measured as $VEGF_{165}$) and FGF-2, which was detectable even at the end of the observation period (i.e., 3 months after injection) versus those regions treated with vehicle alone. See FIG. 10. Surprisingly, the FGF-2 treated ischemic cells were producing statistically significant amounts of both VEGF and FGF-2 3 months after treatment. More surprisingly, the highest concentration (greater than 290 pg/ml) of intracellular FGF-2 was observed in the ischemic myocardial tissue that was treated 3 months earlier with the "mid" dose (0.6 µg/kg, i.e., 13.5 µg) of FGF-2 of SEQ ID NO: 2 IMc. See FIG. 10. In contrast, the "high" dose (6.0 µg/kg, i.e., 135 µg) of FGF-2, while providing for comparable intracellular concentrations of VEGF (about 100 pg/ml), only provided for a concentration of intracellular FGF-2 that was about 165 pg/ml. See FIG. 10. Thus, the "mid" dose of FGF-2, when administered IMc not only stimulated the treated ischemic myocardial cells to produce endogenous VEGF and FGF-2 for three months after treatment, but also stimulated those cells to produce almost twice the concentration of FGF-2 produced by the cells treated with the "high" dose. Given this and the other data provided herein, we would expect production of an unexpectedly superior amount of intracellular FGF-2 to be stimulated by IMc injection of a dose of FGF-2, ranging from about 0.3 µg/kg (or 6.75 µg) to about 3.0 µg/kg (or 67.5 µg). (The data at six months is not yet available.) The presence of both VEGF and FGF-2 suggests a mechanism by which occur increases in perfusion, myocardial function and vascular permeability. Thus, in another aspect, the present invention is directed to a method for increasing the intracellular concentration of VEGF and FGF-2 in ischemic myocardial tissue, comprising injecting the ischemic myocardial tissue with a unit dose of an angiogenic agent. Preferably, the angiogenic agent is an FGF; more preferably, FGF-2.

The method of the present invention was found to improve cardiac function for up to 6 months after treatment when compared to various control groups. Specifically, the % change in peak-stress normalized regional function score was found to decrease, indicating improved cardiac function, for the IMc administered groups at 3 and 6 months post treatment, and that it increased, indicating decreasing function, for the IC and placebo groups. FIG. 11. In addition, the greatest decrease in normalized function scores surprisingly occurred with the "low" dose group, and even more surprisingly showed, by the decreasing function score, that regional myocardial function continued to improve up to 6 months after treatment with the low dose. FIG. 11.

Many of the angiogenic agents, such as acidic FGF (aFGF or FGF-1), basic FGF (bFGF or FGF-2), and VEGF are glycosoaminoglycan binding proteins. The presence of a glycosoaminoglycan (also known as a "proteoglycan" or a "mucopolysaccharide") optimizes the angiogenic activity and AUC of these angiogenic agents. As a result, the unit dosages of FGF-1, FGF-2, VEGF-A, VEGF-B, VEGF-D or the angiogenic fragments and muteins thereof, optionally are administered within 20 minutes of the IV administration of a glycosoaminoglycan, such as a heparin. However, in our experience, the presence of an aminoglycan was not needed for efficacy when a unit dose of an angiogenic agent, e.g., FGF-2, was administered IMc in accordance with the method of the present invention.

BRIEF DESCRIPTION OF THE FIGURES

FIG. 11 shows that the % change in peak-stress normalized regional function score decreased, indicating better function, for the IMc administered groups at 3 and 6 months post treatment, and that it increased, indicating decreasing function, for the IC and placebo groups. In addition, the greatest decrease in normalized function scores occurred with the "low" dose group and surprisingly showed, by the decreasing function score, that function continued to improve up to 6 months after treatment.

DETAILED DESCRIPTION OF THE INVENTION

Figure 1:
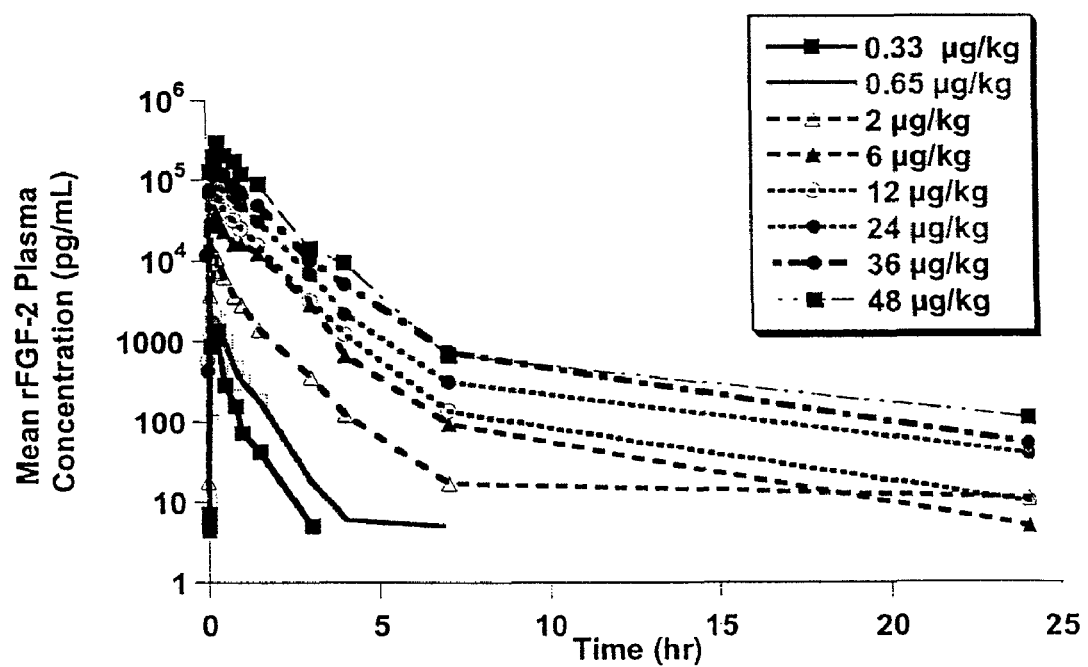
FIG. 1 is a plot of the mean recombinant bovine FGF-2 plasma concentration versus time (hours) for six different doses of rFGF-2 administered by IC infusion in humans over a 20-minute period. The six doses of rFGF-2 in FIG. 1 are 0.33 µg/kg, 0.65 µg/kg, 2 µg/kg, 6 µg/kg, 12 µg/kg, and 24 µg/kg of lean body mass (LBM).

The present invention is based upon human clinical trials of patients manifesting symptoms of coronary artery disease (CAD) and upon comparative testing of the effects produced by various modes of administering a recombinant angiogenic agent in two porcine models of coronary insufficiency. The porcine heart is considered to be a particularly relevant model of the human heart because of its resemblance to the human coronary circulation and its paucity of natural collateral circulation. See Battler et al., "*Intracoronary Injection of Basic Fibroblast Growth Factor Enhances Angiogenesis in Infarcted Swine Myocardium,*" *JACC,* 22(7): 2001-6 (December 1993) at page 2002, col. 1 ("the canine model of myocardial ischemia has been criticized because of the abundance of naturally occurring collateral circulation, as opposed to the porcine model, which 'excels' in its relative paucity of natural collateral circulation and its resemblance to the human coronary circulation."). One of the animal models employed was the porcine model of a hibernating myocardium. This model was created by surgically placing a hydraulic occluder on the proximal end of the left circumflex coronary artery (LCx). Distal to the occluder, there was placed an embedded flow probe which was continuously monitored the occlusion to maintain it at 90%. The hibernating cardiac model is a particularly relevant model of coronary artery disease. Heart muscle may be classified as healthy, hibernating or dead. Dead tissue is not dead but scarred, non-contracting, and no longer capable of contracting even if it were supplied adequately with blood. Hibernating tissue is non-contracting muscle tissue, but is capable of contracting, should it be adequately resupplied with blood. Healthy heart tissue is identified by strong electrical signals in combination with strong displacement. "Dead or diseased heart tissue is identified by weak electrical signals in combination with dysfunctional displacement, i.e., displacement in a direction opposite that of healthy tissue. Ischemic, or hibernating or stunned heart tissue is identified by strong electrical signals in combination with impaired displacement." See U.S. Pat. No. 5,897,529 (Ponzi), which issued Apr. 27, 1999. The diagnosis of hibernating tissue is critical because it is widely believed that once the occlusion is eliminated, there is an immediate return of normal function. See U.S. Pat. No. 5,743,266 (Levene), which issued Apr. 28, 1998. Thus, the hibernating model of the myocardium is similar to what occurs in a human patient having coronary artery disease (CAD) and/or chronic angina wherein one or more coronary vessels are partially occluded.

In the porcine ameroid model, an ameroid constrictor, which is a donut-like band or ring that has a hygroscopic material on its inner face, was placed around the proximal end of the LCx in a pig. The hygroscopic material gradually swells and provides 100% occlusion of the artery in 10 days to 3 weeks. Unlike the hibernating model wherein the percentage of occlusion is hydraulically controllable, consistent and reliable, the ameroid model lacks a consistent control. Also, the complete occlusion in the ameroid model leads to infarction and extensive spontaneous collateral formation, which causes mean blood flow in the resting state to return back to normal, making it more difficult to attribute a particular amount of collateral formation to exogenously administered angiogenic agent. Thus, the ameroid model is not as stringent a model as the hibernating myocardium model. Moreover, the 100% occlusion that is provided by the ameroid model makes the ameroid model more analogous to a myocardial infarction, where there is 100% occlusion of one or more coronary arteries.

Using the above described models, the Applicants discovered that a dose (i.e., from about 5 ng/dose to less than 135,000 ng/dose) of an angiogenic agent (i.e., a unit dose) when administered as a single injection or as a series of injections directly into an ischemic area of the myocardium, induced coronary angiogenesis in the myocardium in the area of administration, but became sufficiently diluted elsewhere in the body to minimize any risk of inducing angiogenesis. More typically, the cumulative amount of angiogenic agent that is administered to the myocardium of a patient is from 5 ng to 67,500 ng of angiogenic agent. Thus, in one aspect, the present invention is directed to a unit dose pharmaceutical composition ("unit dose") comprising from about 5 ng to less than 135,000 ng (preferably from 5 ng to 67,500 ng) of an angiogenic agent in a pharmaceutically acceptable carrier.

By the term "angiogenesis" or "coronary angiogenesis," as used herein, is meant the formation of new blood vessels, ranging in size from capillaries to arterioles which act as collaterals in coronary circulation. In the present invention, angiogenesis was measured using one or more art-accepted indicators that assessed changes in myocardial perfusion, function as measured by a dolbutamine stress echocardiogram, and capillary density.

By the term "angiogenic agent," as used herein, is meant a member selected from the group PDGF, VEGF-A, VEGF-B, VEGF-D, TGF-β1, FGF, or an angiogenically active mutein or fragment thereof. Preferably, the angiogenic agent is VEGF-A, VEGF-D or an FGF or an angiogenically active fragment or mutein thereof. More preferably, the angiogenic agent is an FGF. Most preferably, the angiogenic agent is FGF-2, or an angiogenically active fragment or mutein thereof.

By the phrase "angiogenically active fragment" is meant a protein or polypeptide fragment of an angiogenic agent that exhibits at least 80% of the angiogenic activity of the parent molecule from which it was derived.

By the phrase "angiogenically active mutein," as used herein, is meant an isolated and purified recombinant protein or polypeptide that has 65% sequence identity (homology) to any naturally occurring angiogenic agent selected from the group PDGF, VEGF-A, VEGF-B, VEGF-D, TGF-β1 and FGF, as determined by the Smith-Waterman homology search algorithm (*Meth. Mol. Biol.* 70:173-187 (1997)) as implemented in the MSPRCH program (Oxford Molecular) using an affine gap search with the following search parameters: gap open penalty of 12, and gap extension penalty of 1, and that retains at least 80% of the angiogenic activity of the naturally occurring angiogenic agent with which it has at least 65% sequence identity. Preferably, the angiogenically active mutein has at least 75%, more preferably at least 85%, and most preferably, at least 90% sequence identity to the naturally occurring angiogenic agent. Other well-known and routinely used homology/identity scanning algorithm programs include Pearson and Lipman, *PNAS USA*, 85:2444-2448 (1988); Lipman and Pearson, *Science*, 222:1435 (1985); Devereaux et al., *Nuc. Acids Res.*, 12:387-395 (1984); or the BLASTP, BLASTN or BLASTX algorithms of Altschul, et al., *Mol. Biol.*, 215:403-410 (1990). Computerized programs using these algorithms are also available and include, but are not limited to: GAP, BESTFIT, BLAST, FASTA and TFASTA, which are commercially available from the Genetics Computing Group (GCG) package, Version 8, Madison Wis., USA; and CLUSTAL in the PC/Gene program by Intellegenetics, Mountain View Calif. Preferably, the percentage of sequence identity is determined by using the default parameters determined by the program.

The phrase "sequence identity," as used herein, is intended to refer to the percentage of the same amino acids that are found similarly positioned within the mutein sequence when a specified, contiguous segment of the amino acid sequence of the mutein is aligned and compared to the amino acid sequence of the naturally occurring angiogenic agent.

When considering the percentage of amino acid sequence identity in the mutein, some amino acid residue positions may differ from the reference protein as a result of conservative amino acid substitutions, which do not affect the properties of the protein or protein function. In these instances, the percentage of sequence identity may be adjusted upwards to account for the similarity in conservatively substituted amino acids. Such adjustments are well known in the art. See, e.g., Meyers and Miller, "*Computer Applic. Bio. Sci.*, 4:11-17 (1988).

To prepare an "angiogenically active mutein" of an angiogenic agent of the present invention, one uses standard techniques for site-directed mutagenesis, as known in the art and/or as taught in Gilman, et al., *Gene*, 8:81 (1979) or Roberts, et al., *Nature*, 328:731 (1987). Using one of the site-directed mutagenesis techniques, one or more point mutations would introduce one or more conservative amino acid substitutions or an internal deletion. Conservative amino acid substitutions are those that preserve the general charge, hydrophobicity/hydrophilicity, and/or steric bulk of the amino acid being substituted. By way of example, substitutions between the following groups are conservative: Gly/Ala, Val/Ile/Leu, Lys/Arg, Asn/Gln, Glu/Asp, Ser/Cys/Thr, and Phe/Trp/Tyr. Significant (up to 35%) variation from the sequence of the naturally occurring angiogenic agent is permitted as long as the resulting protein or polypeptide retains angiogenic activity within the limits specified above.

Cysteine-depleted muteins are muteins within the scope of the present invention. These muteins are constructed using site-directed mutagenesis as described above, or according to the method described in U.S. Pat. No. 4,959,314 ("the '314 patent"), entitled "Cysteine-Depleted Muteins of Biologically Active Proteins." The '314 patent discloses how to determine biological activity and the effect of the substitution. Cysteine depletion is particularly useful in proteins having two or more cysteines that are not involved in disulfide formation.

One of the angiogenic agents in the pharmaceutical composition and unit dose of the present invention is PDGF. PDGF is a family of three dimeric angiogenically active proteins, PDGF-AA, PGDF-AB and PGDF-BB, wherein separate genes encode the A-chain and the B-chain, respectively. The PDGF receptor type-alpha (PDGFR-α) binds both the A- or B-chain of the PDF dimers with high affinities, whereas the PDGF receptor type-β (PDGFR-β) only binds the B-chain. All of the PDGFs are angiogenically active in vivo. See Carmeliet, et al., "*Vascular development and disorders: Molecular analysis and pathogenic insights,*" *Kidney Internatl.*, 53:1519-1549 (1998); Risau et al., "*Platelet-derived growth factor is angiogenic in vivo,*" *Growth Factors,* 7:261-266 (1992); Martins, et al., "*The role of PDGF-BB on the development of the collateral circulation after acute arterial occlusion,*" 10:299-306 (1994); and Brown et al., "*Platelet-derived growth factor BB induces functional vascular anastomoses in vivo,*" *PNAS USA,* 92:5920-5924 (1995), which are hereby incorporated herein by reference in their entirety. All other references cited herein, either before or after, are expressly incorporated herein by reference in their entirety. The DNA sequence and the amino acid sequence for the 211 amino acid residue human PDGF A-chain precursor are known in the art. See U.S. Pat. No. 5,219,759, entitled "Recombinant DNA Encoding PDGF A-chain Polypeptide and Expression Vectors," which issued on Jun. 15, 1993 to Hedlin et al. ("the '759 patent") at FIG. 1. The amino acid sequence for the 125 residue mature PDGF A-chain corresponds to residues 87-211 of FIG. 1 of the '759 patent. The '759 patent at FIG. 2 also discloses a cDNA and the deduced amino acid sequence of a variant PDGF A-chain precursor protein, having only 196 amino acid residues, wherein the 110 residue mature PDGF A-chain corresponds to residues 87-196 of the deduced sequence. The first 107 residues of the mature PDGF A-chains (i.e., residues 87-193) are identical. See the '759 patent at FIGS. 1 and 2. Thus, the remaining residues, i.e., residues 108-125 of a mature PDGF A-chain are not critical for activity and may be conservatively substituted without adverse effect. In addition, as the 110 residue variant PDGF A-chain of FIG. 2 of the '759 patent shows, the residues beyond residue 110 of the 125 residue mature PDGF are not necessary for activity, and may be deleted to provide a series of deletion muteins that also would be expected to be functional in the present invention. Another reference discloses that the mature A-chain has 104 amino acids. See U.S. Pat. No. 5,512,545, entitled "PDGF-B Analogues," which issued on Apr. 30, 1996 in the name of Brown et al. ("the '545 patent"), at col. 2, lines 40-44. Thus, the '545 patent suggests that any residues beyond the first 104 of mature PDGF-A are not critical to PDGF-A activity.

Figure 2:
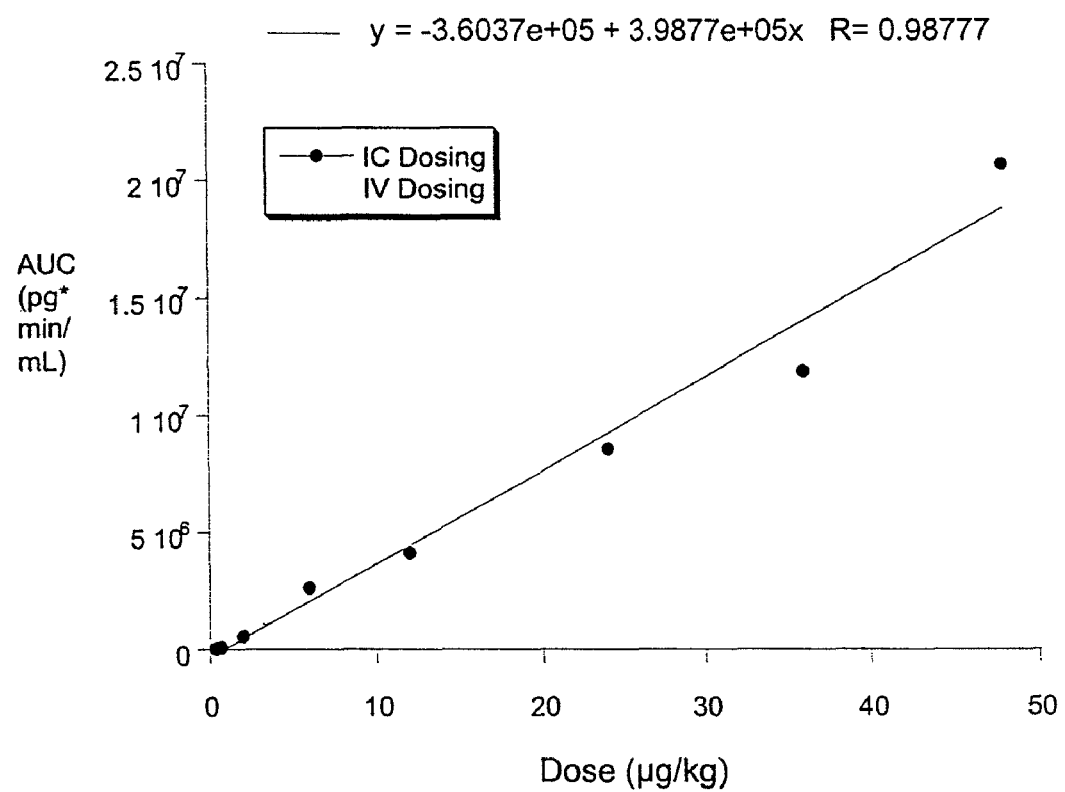
FIG. 2 is a plot of each individual patient's rFGF-2 area under the curve (AUC) in pg·hr/ml for FIG. 1 for the six doses of rFGF-2, and shows the dose linearity of systemic rFGF-2 exposure following IC infusion.
Figure 3:
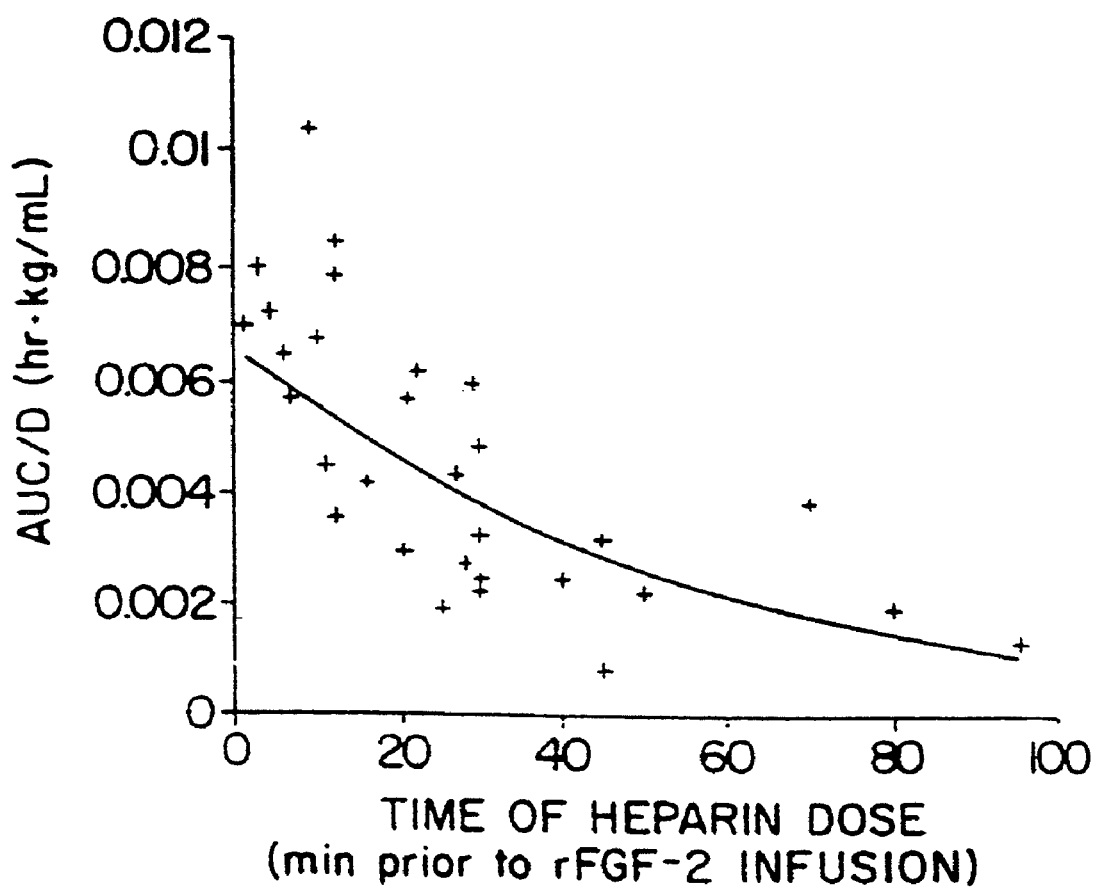
FIG. 3 is a plot of individual human patient rFGF-2 dose normalized AUCs as a function of the time of heparin administration in "minutes prior to rFGF-2 infusion" and shows the influence of timing of heparin administration on rFGF-2 AUC. The rFGF-2 was recombinant bovine FGF-2.

Likewise, the DNA sequence and the deduced amino acid sequence for human PDGF B-chain are known in the art and disclosed in FIGS. 2 and 3, respectively, in the '545 patent. The mature PDGF-A and PDGF-B chains show 60% homology and the 8 cysteine residues in each chain are conserved. Although PDGF B-chain may have the full complement of 160 amino acids shown in FIG. 2 and SEQ ID NO: 1 of the '545 patent, the last 51 residues may be removed without loss of activity. The resulting carboxy-truncated PDGF B-chain has 109 residues (i.e., residues 1-109 of SEQ ID NO: 1 and FIG. 3 of the '545 patent) and contains the binding region, which occurs between residues 25 (Ile) and 37 (Phe). If the PDGF B-chain is expressed in yeast, it is desirable to replace the Arg at residue positions 28 or 32 or both with a non-basic, neutral residue to prevent cleavage by the yeast cells. Methods, vectors, and cells for expressing the PDGF A-chain and B-chain, and for combining these A-chains and B-chains to make the three isoforms of PDGF are well known in the art. See U.S. Pat. Nos. 5,605,816 and 5,512,545 as cited above.

Figure 4:
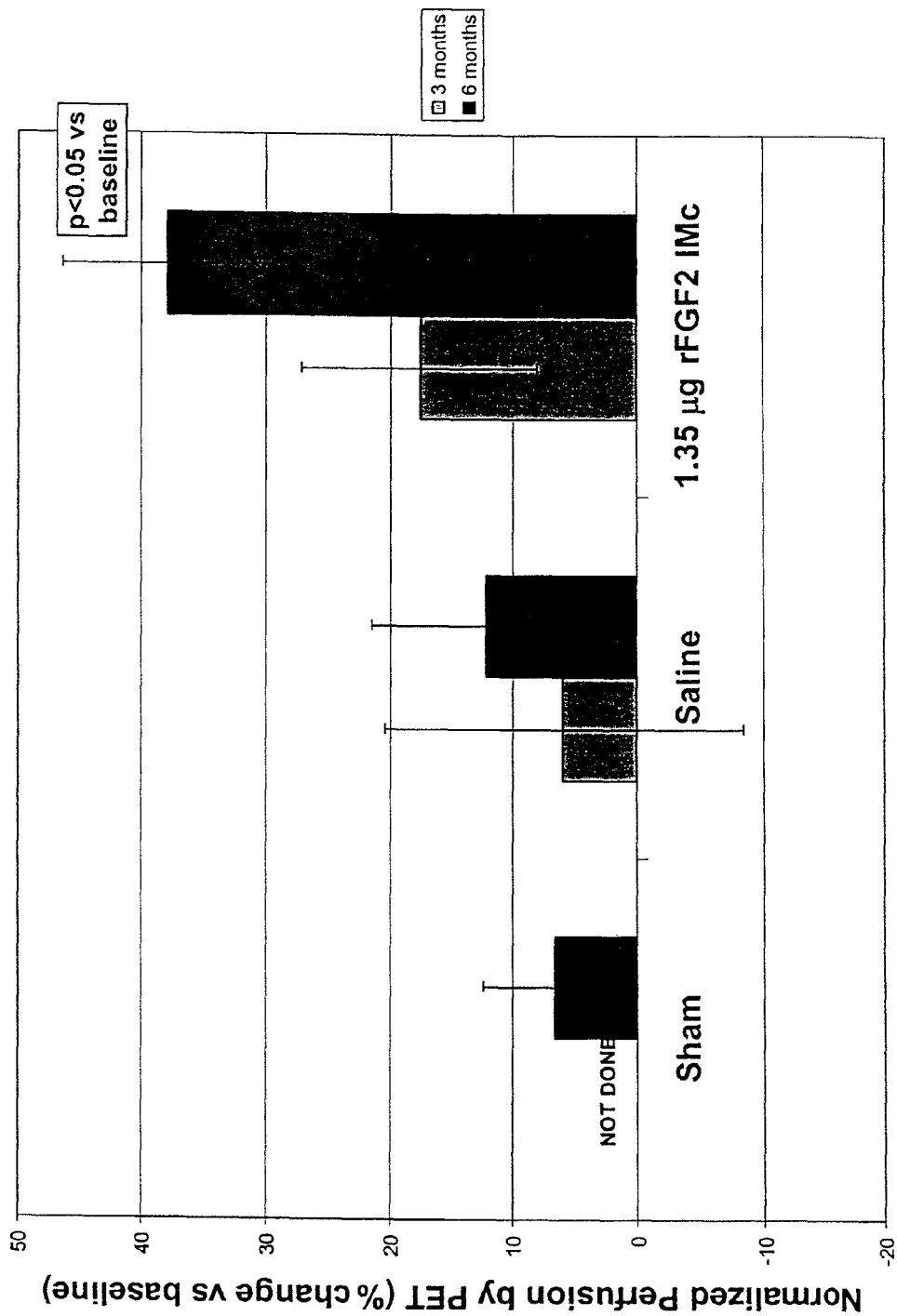
FIG. 4 is a bar graph comparing the normalized myocardial perfusion (reported as % change from baseline) in the pig model of the hibernating myocardium, as measured by positron emission tomography (PET), at 3 and 6 months following: sham administration; saline; and a unit dose containing 1.35 µg of rFGF-2 (SEQ ID NO: 2).

Another angiogenic agent that is an active agent in the pharmaceutical composition and unit dose of the present invention is VEGF. VEGF is a basic, homodimeric protein having a molecular weight of about 45,000 Daltons (45 kD) that has four homologues, designated as VEGF (or VEGF-A), VEGF-B, VEGF-C and VEGF-D. For clarity herein, the first member of the family, VEGF, will be referred to herein as VEGF-A. The VEGF family of proteins is characterized by having a highly conserved central region, characterized by the invariant presence in homologous positions of 15 cysteine residues, 8 of which are involved in intra- and intermolecular disulfide bonding. See Ferrara, et al., "*The Biology of Vascular Endothelial Growth Factor,*" *Endocrine Reviews,* 18(1): 4-25 (1997) at FIG. 4. As a result, the four VEGF homologues have a similar shape (tertiary structure) and are capable of spontaneously forming heterodimers when coexpressed. Accordingly, deletion muteins at the N- and C-terminal ends of the VEGFs that retain the internal cysteines would be expected to retain their shape, form dimers and be biologically active. The homologous positioning of 8 of the 15 conserved cysteine residues of VEGF correspond to the 8 conserved cysteine residues of the PDGF family as comparatively shown in e.g., WO 98/02543 at FIG. 3; and Keck, et al., "*Vascular Permeability Factor, an Endothelial Cell Mitogen Related to PDGF,*" *Science* 246:1309-1312 (1989) at page 1311, col. 2 and FIG. 4.

Human VEGF-A exists in four isoforms, having 121, 165, 189 and 206 amino acids, respectively. These four isoforms are designated as VEGF-$A_{121}$, VEGF-$A_{165}$, VEGF-$A_{189}$, and VEGF-$A_{206}$, respectively. See Ferrara, et al., "*The Biology of Vascular Endothelial Growth Factor,*" *Endocrine Reviews,* 18(1):4-25 (1997) at page 5. The human VEGF-A gene is organized into eight (8) exons separated by seven (7) introns and its coding region spans 14 kb. Id. Alternative exon splicing of the single VEGF-A gene accounts for all of the heterogeneity. VEGF-$A_{165}$ lacks the residues encoded by exon 6, while VEGF-$A_{121}$ lacks the residues encoded by exons 6 and 7. Id. The three shorter isoforms of VEGF-A are based upon VEGF-$A_{206}$ and reflect splice variations that occur in the carboxy half of the molecule. However, the last six amino acids (exon 8) of the carboxy terminus are conserved in all four splice variants.

The cDNA sequence that encodes human VEGF-$A_{121}$ and the corresponding amino acid sequence are well known in the art. See Leung, et al., "*Vascular endothelial growth factor is a secreted angiogenic mitogen,*" *Science* 246:1306-1309 (1989) at FIG. 2B as described at page 1307, col. 3. The cDNA and deduced amino acid sequence for human VEGF-$A_{165}$ are also well known in the art. See Leung, et al., "*Vascular endothelial growth factor is a secreted angiogenic mitogen,*" *Science* 246:1306-1309 (1989) at page 1307 and FIG. 2B. Likewise, the cDNA and deduced amino acid sequence for human VEGF-A$_{189}$ have been well known in the art since 1991. See Keck, et al., "*Vascular Permeability Factor, an Endothelial Cell Mitigen Related to PDGF,*" *Science,* 246: 1309-1312 (1989); see also Tischer et al., "*The human gene for vascular endothelial growth factor,*" *J. Biol. Sci.,* 266: 11947-11954 (1991). Finally, the cDNA and deduced amino acid sequence for human VEGF-A$_{206}$ are also well known in the art. See Houck, et al., "*The vascular endothelial growth factor family: identification of a fourth molecular species and characterization of alternative splicing of RNA,*" *Mol. Endocrinol.* 5:1806-1814 (1991) at FIG. 2A.

An overlapping comparison of the amino acid sequences of the four splice variants (isoforms) of VEGF-A is shown in Ferrara, et al., "*Molecular and Biological Properties of the Vascular Endothelial Growth Factor Family of Proteins,*" *Endocrine Reviews* 13(1):18-32 (1992) at page 21, FIG. 1. The shortest isoform, VEGF-A$_{121}$, which is freely soluble in the extracellular milieu, is slightly acidic due to the absence of most of the carboxy terminus (i.e., exons 6 and 7) which are rich in basic amino acid residues. The longer isoforms, VEGF-A$_{165}$, VEGF-A$_{189}$, and VEGF-A$_{206}$, are less soluble, and thus, less diffusible, than VEGF-A$_{121}$, but exhibit both a mitogenic activity and a binding affinity for a heparin-rich matrix that increases with increasing length at the carboxy terminus. By way of example, VEGF-A$_{165}$ is more than 100-fold more mitogenic than VEGF-A$_{121}$. See Carmeliet et al., "*Vascular development and disorders: Molecular analysis and pathogenic insights,*" *Kidney International,* 53:1519-1549 (1998) at pages 1521-1522. Thus, while all VEGF-A isoforms are active and within the scope of angiogenic agents of the present invention, the highly basic and heparin binding carboxy terminus of VEGF-A is important to maximizing activity. Although the mechanism by which VEGF-A stimulates angiogenesis is not known, Banai suggests that VEGF-A promotes angiogenesis in part via stimulation of endothelial release of PDGF. Banai, et al., "*Angiogenic-Induced Enhancement of Collateral Blood Flow to Ischemic Myocardium by Vascular Endothelial Growth Factor in Dogs,*" *Circulation,* 89(5):2183-2189 (May 1994). VEGF-A binds to the VEGF receptor-1 (VEGFR-1 or FLT1) and to the VEGF receptor-2 (VEGFR-2 or FLK1).

Human VEGF-B, which is found in abundance in heart and skeletal muscle, is a known nonglycosylated highly basic heparin binding protein that has the amino acid sequence shown in FIG. 1 of Olofsson, et al., "*Vascular endothelial growth factor B, a novel growth factor for endothelial cells,*" *PNAS USA* 93:2576-2581 (1996). Like the VEGF-As, VEGF-B is expressed as a prohormone and has 188 amino acid residues of which residues 1-21 are a putative leader sequence and thus are not necessary for angiogenic activity. Id. Hence, mature human VEGF-B comprises the 167 residues that follow the putative leader sequence. Olofsson at FIG. 1. The human prohormone VEGF-B also has 88% sequence identity to murine prohormone VEGF-B, varying at residue positions 12, 19, 20, 26, 28, 30, 33, 37, 43, 57, 58, 63, 65, 105, 130, 140, 144, 148, 149, 165, 168, 186 and 188 in a conserved manner. Olofsson at page 2577, col. 2, and FIGS. 1 and 2 therein. The differences in residues in going from mature human VEGF-B to mature murine VEGF-B are as follows: 5 Pro→Phe, 7 Ala→Gly, 9 Gly→Ser, 12 Arg→Lys, 16 Ser→Pro, 22 Thr→Ala, 36 Thr→Ser, 37 Val→Met, 42 Thr→Asn, 44 Ala→Val, 86 Arg→Gln, 119 Asp→Glu, 129 Pro→Ile, 133 Arg→Pro, 137 His→Arg, 138 His→Arg, 165 Ser→Arg, 168 Arg→His, 165 Leu→Pro, and 167 Arg→Lys. Accordingly, an angiogenic agent of the present invention includes a human VEGF-B mutein having a conservative substitution at one or more of the above-referenced residue positions. Preferably, the conservative substitution is one or more of the above referenced differences in the second preceding sentence above.

VEGF-C, which is expressed most prominantly in the heart, lymph nodes, placenta, ovary, small intestine and thyroid, is induced by a variety of growth factors, inflammatory cytokines and hypoxia. VEGF-C is recombinantly expressed as disclosed in Joukov et al. and has the amino acid sequence disclosed at page 291 and FIG. 3 therein. See Joukov et al., "*A novel vascular endothelial growth factor, VEGF-C, is a ligand for the Flt4 (VEGFR-3) and KDR (VEGFR-2) receptor tyrosine kinases,*" The EMBO Journal, 15(2):290-298 (1996); also Ferrara, et al., "*The Biology of Vascular Endothelial Growth Factor,*" Endocrine Reviews, 18(1):4-25 (1997) at FIG. 3. VEGF-C is the largest member of the VEGF family, having 399 amino acid residues and 32% homology to VEGF-A. See Ferrara (1997) at page 11, col. 1. The carboxy end of VEGF-C contains 180 residues of insert (at residue positions 213-295) that are not found in the other VEGFs. See Joukov et al. (1996) at FIG. 3: or Ferrara, et al., "*The Biology of Vascular Endothelial Growth Factor,*" Endocrine Reviews, 18(1):4-25 (1997) at FIG. 4. Given its large size, VEGF-C would be the least desirable member of the VEGF family. However, deletion muteins of VEGF-C, lacking residues 213-295, or fragments thereof, lacking one or more residues at the N-terminus, up to residues 1-28 are also within the scope of the term angiogenic factor as used in the present invention. VEGF-C binds to VEGFR-2 (previously known as flt-1 and KDR/Flk-1) and to VEGFR-3 (also known as Flt4). See Joukov et al. (1996).

VEGF-D, which is the most recent member of the VEGF family to be discovered, is encoded by the cDNA and has the amino acid sequence shown in FIG. 2 of commonly assigned U.S. Ser. No. 09/043,476, filed Mar. 18, 1998; and corresponding WO 97/12972 which was published on Apr. 10, 1997. VEGF-D is a dimerizing protein having 304 amino acid residues. The core of VEGF-D is highly conserved relative to the other VEGF proteins. More importantly, it contains the 15 cysteine residues at residue positions 111, 136, 142, 145, 146, 153, 189, 191, 258, 269, 271, 273, 300, 312 and 314 that are highly conserved throughout the VEGFs and PDGFs. Overlapping comparisons of the amino acid sequences of the VEGFs and some of the PDFs, showing the conserved areas, are found in Ferrara, et al., "*The Biology of Vascular Endothelial Growth Factor,*" Endocrine Reviews, 18(1):4-25 (1997) at FIG. 4; in WO 97/12972 and its U.S. equivalent U.S. Ser. No. 09/043,476 at FIG. 3; and WO 98/02543 at FIG. 3. Biologically active alleles and fragments of the VEGF-D are known in the art. In one example, WO 98/07832 discloses a biologically active human VEGF-D that was isolated from lung that differs from the VEGF-D of WO 97/12972 by having the following variations at the designated residue positions: 56 Thr→Ile, 151 Phe→Leu, 152 Met→Ile, 261 Asp→His, 264 Glu→Phe, and 297 Glu→Leu. Accordingly, it is within the scope of the present invention that the angiogenic agent include muteins of VEGF-D that include one or more of the above-referenced amino acid substitutions or a conservative substitution at one or more of the above-referenced residue sites. Such muteins are made by site directed mutagenesis, which is a standard technique in the art. In addition, a biologically active VEGF-D that was isolated from human breast tissue lacked the first 30 amino acids. See WO 98/24811. Accordingly, it is within the scope of this invention that angiogenic agent include fragments of VEGF-D that lack amino acid residues 1-30 of the mature VEGF-D. Moreover, insofar as residues 109-315 of mature VEGF-D contain the highly conserved region that is responsible for dimerization and binding to receptor, it is also within the scope of the present invention that the angiogenic agent include an N-truncated and/or C-truncated VEGF-D comprising residues 109-315 of the mature hormone of FIG. 2 of WO 97/12972 or corresponding U.S. Ser. No. 09/043,476.

TGF-β1 is a member of the TGF-β superfamily, having two dozen members. The various members of the TGF-β superfamily are homo- or hetero-dimers of a mature protein having 110-140 amino acid residues and at least seven cysteines. Six of the cysteines form internal disulfides and the seventh forms a disulfide bond that links the two monomers together. See Kingsley, D. M., "*The TGF-β superfamily: new members, new receptors, and new genetic tests of function in different organisms,*" Genes and Develop., 8:133-146 (1994). The TGF-β1 monomer, like the other monomers of the TGF-β superfamily, has a structural similarity with PDGF, albeit less than 10%. The monomer for human TGF-β1 is a known 112 residue protein encoded by the cDNA and having the deduced amino acid sequence shown in FIG. 1B(III) of U.S. Pat. No. 4,886,747, entitled "Nucleic Acid Encoding TGF-β and Its Uses," which issued on Dec. 12, 1989 to Derynck et al. and discloses methods for expressing recombinant TGF-β1. Although TGF-β1 has 112 amino acid residues, only the sequence of residues corresponding to residue positions 16-31 (i.e., CVRQLYIDFRKDLGWK) of the mature TGF-β1 (see e.g., FIG. 1B(III) of the '747 patent) is necessary for activity. See U.S. Pat. No. 5,658,883, entitled "Biologically Active TGF-β1 Peptides," which issued on Aug. 17, 1997 to Ogawa et al. A larger dimerized fragment of mature human TGF-131, corresponding to residues 16-47 (i.e., CVRQLYIDFRKDLGWKWIHEPKGYHANFCLGP), exhibited similar activity to dimers of the 16-31 fragment and to dimers of mature TGF-β1. The 16-31 residue fragment is dimerized by forming disulfide bonds between the amino terminal cysteines of two monomeric subunits. The 16-47 residue fragment is dimerized by forming disulfide bonds between the amino terminal cysteines, the carboxy terminal cysteines or both of two monomer subunits. Thus, it is within the scope of the present invention that a fragment of TGF-β1 need only comprise residues 16-31 of the mature human TGF-β1 to be an active fragment. In addition to directly inducing angiogenesis, there is speculation that TGF-β1 may induce angiogenesis indirectly in vivo by affecting inflammatory or connective tissue cells, which in turn can produce angiogenic molecules, such as VEGF-A, PDGF, FGF-2, etc. See Carmeliet (1998).

Another angiogenic agent suitable for use in the compositions and method of the present invention is FGF. By the term "FGF," as used herein, is meant a fibroblast growth factor protein that also has angiogenic activity (such as FGF-1, FGF-2, FGF-4, FGF-6, FGF-8, FGF-9 or FGF-98) or an angiogenically active fragment or mutein thereof. Typically, the FGF is human (h) FGF-1, bovine (b) FGF-1, hFGF-2, bFGF-2, hFGF-4 or hFGF-5. In an alternative embodiment, the active agent in the unit dose is hFGF-6, mFGF-8, hFGF-9 or hFGF-98.

The amino acid sequences and methods for making many of the FGFs that are employed in the unit dose pharmaceutical composition and method of the present invention are well known in the art. In particular, references disclosing the amino acid sequence and recombinant expression of FGF 1-9 and FGF-98 are discussed sequentially below.

FGF-1: The amino acid sequence of hFGF-1 and a method for its recombinant expression are disclosed in U.S. Pat. No. 5,604,293 (Fiddes), entitled "Recombinant Human Basic Fibroblast Growth Factor," which issued on Feb. 18, 1997. See FIG. 2d of the '293 patent. This reference and all other references herein, whether cited before or after this sentence, are expressly incorporated herein by reference in their entirety. The amino acid sequence of bFGF-1 is disclosed in U.S. Pat. No. 5,604,293 (Fiddes) at FIG. 1b, as is a method for its expression. The mature forms of both hFGF-1 and bFGF-1 have 140 amino acid residues. bFGF-1 differs from hFGF-1 at 19 residue positions: 5 Pro→Leu, 21 His→Tyr, 31 Tyr→Val, 35 Arg→Lys, 40 Gln→Gly, 45 Gln→Phe, 47 Ser→Cys, 51 Tyr→Ile, 54 Tyr→Val, 64 Tyr→Phe, 80 Asn→Asp, 106 Asn→His, 109 Tyr→Val, 116 Ser→Arg, 117 Cys→Ser, 119 Arg→Leu, 120 Gly→Glu, 125 Tyr→Phe and 137 Tyr→Val. In most instances, the differences are conserved. Further, the differences at residue positions 116 and 119 merely interchange the position of the Arg.

FGF-2: The cDNA sequence (SEQ ID NO: 4) encoding the full length 155 residue human FGF-2 (SEQ ID NO: 5) and methods for recombinant expression of human FGF-2 (hFGF-2) are disclosed in U.S. Pat. No. 5,439,818 (Fiddes) entitled "DNA Encoding Human Recombinant Basic Fibroblast Growth Factor," which issued on Aug. 8, 1995 (see FIG. 4 therein), and in U.S. Pat. No. 5,514,566 (Fiddes), entitled "Methods of Producing Recombinant Fibroblast Growth Factors," which issued on May 7, 1996 (see FIG. 4 therein). Human FGF-2 also has an active N-truncated 146 residue form of SEQ ID NO: 6, that lacks the first nine residues from the N-terminus of SEQ ID NO: 5. This truncated form is readily produced by making appropriate deletions to the 5' end of the cDNA of SEQ ID NO: 4, using art-known techniques. The cDNA sequence (SEQ ID NO: 1) encoding bovine FGF-2 (SEQ ID NO: 2) and various methods for its recombinant expression are disclosed in U.S. Pat. No. 5,155,214, entitled "Basic Fibroblast Growth Factor," which issued on Oct. 13, 1992. When the 146 residue forms of hFGF-2 and bFGF-2 are compared, their amino acid sequences are nearly identical with only two residues that differ. In particular, in going from hFGF-2 to bFGF-2, the sole differences occur at residue positions 112 (Thr→Ser) and 128 (Ser→Pro).

FGF-3: FGF-3 was first identified as an expression product of a mouse int-2 mammary tumor and its amino acid sequence is disclosed in Dickson et al., "*Potential Oncogene Product Related to Growth Factors,*" Nature 326:833 (Apr. 30, 1987). FGF-3, which has 243 residues when the N-terminal Met is excluded, is substantially longer than both FGF-1 (human and bovine) and FGF-2 (human and bovine). A comparison of amino acid residues for mFGF-3 relative to bFGF-1 and bFGF-2 is presented in overlap fashion in Dickson, et al. (1987). When the amino acid sequence of mFGF-3 is compared to bFGF-1 and bFGF-2, FGF-3 has 5 locations containing residue inserts relative to both FGF-1 and FGF-2. The most significant of these inserts is a 12 and a 14 residue insert relative to FGF-2 and FGF-1, respectively, beginning at residue position 135 of FGF-3. Allowing for the inserts, Dickson discloses that mFGF-3 has 53 residue identities relative to FGF-1 and 69 residue identities relative to FGF-2. In addition, FGF-3 contains a hydrophobic N-terminal extension of 10 residues relative to the N-terminus of the signal sequence in both FGF-1 and FGF-2. Relative to the C-terminus of bFGF-1 and bFGF-2, mFGF-3 contains an approximately 60 residue extension. It is unlikely that the C-terminal extension of mFGF-3 is necessary for activity. More likely, it is a moderator of activity by conferring receptor specificity on the FGF.

FGF-4: The amino acid sequence for the hst protein, now known as hFGF-4, was first disclosed by Yoshida, et al., "*Genomic Sequence of hst, a Transforming Gene Encoding a Protein Homologous to Fibroblast Growth Factors and the int-2-Encoded Protein,*" PNAS USA, 84:7305-7309 (October 1987) at FIG. 3. Including its leader sequence, hFGF-4 has 206 amino acid residues. When the amino acid sequences of hFGF-4, hFGF-1, hFGF-2 and mFGF-3 are compared, residues 72-204 of hFGF-4 have 43% homology to hFGF-2; residues 79-204 have 38% homology to hFGF-1; and residues 72-174 have 40% homology to mFGF-3. A comparison of these four sequences in overlap form is shown in Yoshida (1987) at FIG. 3. Further, the Cys at residue positions 88 and 155 of hFGF-4 are highly conserved among hFGF-1, hFGF-2, mFGF-3 and hFGF-4 and are found in a homologous region.

The two putative cell-binding sites of hFGF-2 occur at residue positions 36-39 and 77-81 thereof. See Yoshida (1987) at FIG. 3. The two putative heparin-binding sites of hFGF-2 occur at residue positions 18-22 and 107-111 thereof. See Yoshida (1987) at FIG. 3. Given the substantial similarity between the amino acid sequences for human and bovine FGF-2, we would expect the cell-binding sites for bFGF-2 to also be at residue positions 36-39 and 77-81 thereof, and the heparin-binding sites to be at residue positions 18-22 and 107-111 thereof. In relation to hFGF-1, the putative cell-binding sites occur at residues 27-30 and 69-72, and the putative heparin-binding sites occur at residues 9-13 and 98-102. Insofar as mature bFGF-1 has the identical amino acids at residue positions 9-13, 27-30, 69-72 and 98-102 as does mature hFGF-2, bFGF-1 would be expected to have the same cell- and heparin-binding sites as does hFGF-1.

FGF-5: The cDNA and deduced amino acid sequence for hFGF-5 are disclosed in Zhan, et al., "*The Human FGF-5 Oncogene Encodes a Novel Protein Related to Fibroblast Growth Factors*," Molec. and Cell. Biol., 8(8):3487-3495 (August 1988) at FIG. 1. Zhan also discloses a method for cloning hFGF-5. The Applicants also sequenced hFGF-5 and obtained an amino acid sequence which differed from Zhan's sequence at residue position 236 (having a Lys instead of the Zhan's Asn) and at residue position 243 (having a Pro instead of Zhan's Ser). Both amino acid sequences for hFGF-5 have 266 amino acid residues that include a leader sequence of 67 residues upstream of the first residue of mature FGF-2 and a tail sequence that extends about 47 residues beyond the C-terminus of hFGF-2. A comparison between the amino acid sequences of hFGF-1, hFGF-2, mFGF-3, hFGF-4 and FGF-5 is presented in FIG. 2 of Zhan (1988). In FIG. 2 of Zhan, hFGF-1, hFGF-2, mFGF-3 and hFGF-4 are identified as aFGF (i.e., acidic FGF), bFGF (i.e., basic FGF), int-2, and hstKS3, respectively, i.e., by their original names. In the above referenced comparison, two blocks of FGF-5 amino acid residues (90 to 180 and 187-207) showed substantial homology to FGF 1-4, i.e., 50.4% with FGF-4, 47.5% with FGF-3, 43.4% with FGF-2 and 40.2% with hFGF-1. See Zhan (1988) at FIG. 2. U.S. Pat. Nos. 5,155,217 (Goldfarb) and 5,238,916 (Goldfarb), which correspond to the Zhan publication, refer to the FGF-5 of Zhan as FGF-3. However, the art (as evidenced by Coulier below) has come to recognize that the hFGF of Zhan (and of the Goldfarb patents) as FGF-5 and not as FGF-3. The two Goldfarb patents contain the same amino acid sequence for hFGF-5 as reported above by Zhan.

FGF-6: The cDNA and deduced amino acid sequence for hFGF-6 are disclosed in Coulier et al., "*Putative Structure of the FGF-6 Gene Product and Role of the Signal Peptide*," Oncogene 6:1437-1444 (1991) at FIG. 2. Coulier also discloses a method for cloning FGF-6. hFGF-6 is one of the largest of the FGFs, having 208 amino acid residues. When the amino acid sequences of human FGF-1, FGF-2, FGF-3, FGF-4, FGF-5, FGF-6 and FGF-7 are compared, there are strong similarities in the C-terminal two-thirds of the molecules (corresponding e.g., to residues 78-208 of hFGF-6. In particular, 23 residues of FGF-6, including the two cysteines at residue positions 90-157 of hFGF-6 were identical between the seven members of the family. This number increases to 33 residues when conserved amino acid residues are considered. The overall similarities between these seven human FGFs ranged from 32% to 70% identical residues and 48% to 79% conserved residues for the C-terminal two-thirds of the molecules. The sequence comparisons of hFGF-1 to hFGF-5 and hFGF-7, relative to hFGF-6, are shown in Table 1 herein.

TABLE 1

Amino Acid Sequence Comparison of hFGF-6 With Other hFGFs

| | Identical Residues* | Conserved Residues** | Identical Residues* (%) | Conserved Residues** (%) |
|---|---|---|---|---|
| hFGF-4 | 91 | 103 | 70 | 79 |
| hFGF-5 | 64 | 82 | 49 | 63 |
| hFGF-3 | 55 | 78 | 42 | 60 |
| hFGF-2 | 54 | 69 | 42 | 53 |
| hFGF-7 | 47 | 68 | 36 | 52 |
| hFGF-1 | 42 | 62 | 32 | 48 |

*Number and percentages of identical or conserved residues were calculated for the C-terminal two-thirds of the hFGF6 molecule (residues 78-208).
**Conserved residues are defined according to the structure-genetic matrix of Feng et al., J. Mol. Evol., 21: 112-125 (1985).

Referring to Table 1, FGF-6 has the highest correspondence (91 identical residues/103 conserved residues) with FGF-4. This amounts to 70% identical and 79% conserved residues. hFGF-6 differed most from hFGF-3, hFGF-2, hFGF-7 and hFGF-1, with 42, 42, 36 and 32; identical residues, respectively.

An overlaid comparison of the amino acid sequences of FGFs 1-7 is shown in FIG. 3 of incorporated Coulier (1991). FIG. 3 of Coulier shows that when in the C-terminal two thirds of the FGF molecules are aligned, there are 23 residue positions wherein the residues from all seven FGF members are identical. There are also ten residue positions wherein residues from all seven FGF members are conserved. Coulier (1991) at FIG. 3. In combination, these identical and conserved residues form about 6 locations of three to five residues on the terminal two thirds of each of the FGFs 1-7, wherein three to five residues are grouped together in all seven species of human FGF (i.e., hFGF 1-7).

FGF-7: The amino acid sequence of hFGF-7 is well-known in the art and disclosed in Miyamoto, et al., "*Molecular Cloning of a Novel Cytokine cDNA Encoding the Ninth Member of the Fibroblast Growth Factor Family, Which Has a Unique Secretion Property*," Mol. and Cell. Biol. 13(7):4251-4259 (1993) at FIG. 2. In Miyamoto, the hFGF-7 was referred to by its older name "KGF". FGF-7 has 191 amino acid residues. A comparison of the amino acid sequence of hFGF-7 to the amino acid sequences of hFGF 1-6 and hFGF-9 shows that the carboxy terminal two thirds of the FGF-7 has comparable homology with the distal two thirds of the other members of the group. See Miyamoto (1993) at page 4254 (FIG. 2).

FGF-8: The cDNA and deduced amino acid sequence of mFGF-8 is well-known in the art and disclosed in Tanaka et al., "*Cloning and Characterization of an Androgen-induced Growth Factor Essential for the Growth of Mouse Mammary Carcinoma Cells*," PNAS USA, 89:8928-8932 (1992) at FIG. 2. Tanaka also discloses a method for making recombinant FGF-8. The mFGF-8 of Tanaka has 215 amino acid residues. MacArthur, et al., "*FGF-8 isoforms activate receptor splice forms that are expressed in mesenchymal regions of mouse development*," Development, 121:3603-3613 (1995) discloses that FGF-8 has 8 different isoforms that differ at the mature N-terminus but that are identical over the C-terminal region. The 8 isoforms arise because FGF-8 has 6 exons of which the first four (which correspond to the first exon of most other FGF genes) result in alternative splicing.

FGF-9: The cDNA and deduced amino acid sequences of human and murine FGF-9 are known in the art and methods for their recombinant expression are disclosed in Santos-Ocampo, et al., "*Expression and Biological Activity of Mouse Fibroblast Growth Factor*," J. Biol. Chem., 271(3):1726-1731 (1996). Both the human and murine FGF-9 molecules have 208 amino acid residues and sequences that differ by only two residues. In particular, hFGF-9 has Asn and Ser at residues 9 and 34, respectively, whereas mFGF-9 has Ser and Asn, respectively. FGF-9 has complete preservation of the conserved amino acids that define the FGF family. Santos-Ocampo (1996) at page 1726. Half-maximal activation of FGF-9 is seen at 185 ng/ml heparin, whereas half-maximal activation of FGF-1 is seen at 670 ng/ml heparin. Santos-Ocampo (1996) at page 1730. When compared to FGF-1, both FGF-2 and FGF-9 require lower heparin concentrations for optimal activity.

FGF-98: The cDNA and amino acid sequence of hFGF-98 and a method for its recombinant expression are disclosed in provisional patent application Ser. No. 60/083,553 which is hereby incorporated herein by reference in its entirety. hFGF-98, which is also known as hFGF-18, has 207 amino acid residues. Thus, hFGF-6 (207 residues), hFGF-9 (208 residues) and hFGF-98 (207 residues) are similar in size.

FGFs differentially bind to and activate one or more of four related transmembrane receptors which in turn mediate a biological response. The FGF receptors ("FGFR") are members of the tyrosine kinase receptor superfamily. The extracellular domain of the FGFR comprises 2-3 immunoglobulin-like ("Ig-like") domains that are differentially expressed as a result of alternative splicing. Another alternative splicing event can also alter the sequence of the carboxy-terminal half of the Ig-like domain III without altering the reading frame. Santos-Ocampo (1996). The two splice forms, which are referred to as "b" and "c", occur for FGFRs 1, 2, 3 but not 4. A more detailed description of the FGFR is found in Mathieu, et al, "*Receptor Binding and Mitogenic Properties of Mouse Fibroblast Growth Factor* 3," J. Biol. Chem., 270(41):24197-24203 (1995). The ability of FGF 1-9 to differentially stimulate FGFRs was receptor dependent as reported by Ornitz et al., J. Biol. Chem., 271(25):15292-15297 (1996). In Ornitz, the cell line BaF3 was divided into fractions and each fraction was transfected to express one of the following FGF receptors: FGFR1b, FGFR1c, FGFR2b, FGFR2c, FGFR3b, FGFR3c and FGF4 (minus one Ig-like domain). Thereafter, the transformed cell lines were exposed to one of FGF 1-9 (5 nM) and heparin (2 μg/ml) as a cofactor. The mitogenic response was then measured by incorporation of [$^3$H] thymidine. The results in cpm are as follows:

1. FGFR1b: similar mitogenic responses were produced by hFGF-1 (32,000 cpm) and hFGF-2 (28,000 cpm) with the next highest responses by mFGF-3 (about 16,000 cpm) and hFGF-4 (15,000 cpm);

2. FGFR1c: similar mitogenic responses were produced by hFGF-1, hFGF-2, hFGF-4, hFGF-5, and hFGF-6 (about 36,000 cpm), with mFGF-9 producing the only other significant response (about 19,000 cpm);

3. FGFR2b: best mitogenic responses were by hFGF-7 (14,000 cpm), hFGF-1 (12,500 cpm) and mFGF-3 (9,500 cpm);

4. FGFR2c: best mitogenic responses were by hFGF-4 (21,000 cpm), mFGF-9 (20,000 cpm), hFGF-6 (16,500 cpm), hFGF-1 (16,000 cpm), hFGF-2 (14,500 cpm), hFGF-5 (9,500 cpm), and mFGF-8 (9,000 cpm);

5. FGFR3b: mitogenic responses only by hFGF-1 (37,000 cpm) and mFGF-9 (26,000 cpm);

6. FGFR3c: best mitogenic responses by hFGF-1 (39,000 cpm), hFGF-2 (34,000 cpm), hFGF-4 (33,000 cpm), mFGF-8 (32,500 cpm), mFGF-9 (31,000 cpm), hFGF-5 (16,000 cpm) and hFGF-6 (13,000 cpm);

7. FGFR4): best mitogenic responses by hFGF-2 (29,000 cpm), hFGF-4 and hFGF-6 (27,000 cpm), mFGF-8 (25,000 cpm), mFGF-1 (24,000 cpm), and hFGF-9 (20,000 cpm) with all others being 6,000 cpm or less.

As reflected above, only FGF-1 induces a significant mitogenic response in all of the receptors tested. Thus, FGF-1 can be thought of as a universal ligand with N- and C-terminal additions to the molecule giving rise to receptor specificity associated with the other FGF. Given the potential for diverse responses in vivo by systemically administered FGF, the present invention minimizes the potential for systemic responses by localized administration, and by discovering the appropriate dosage for the localized administration, i.e., by administering a therapeutically effective amount of a FGF into at least one coronary artery of a patient in need of treatment for CAD. In the Examples that follow, bFGF-2 was administered in vivo to rats, pigs and humans, and tested for angiogenic activity. The bFGF-2 of the Examples was made as described in U.S. Pat. No. 5,155,214 ("the '214 patent"). In the method of the '214 patent, a cDNA encoding bFGF (hereinafter "FGF-2") is inserted into a cloning vector, such as pBR322, pMB9, Col E1, pCRI, RP4 or λ-phage, and the cloning vector is used to transform either a eukaryotic or prokaryotic cell, wherein the transformed cell expresses the FGF-2. In one embodiment, the host cell is a yeast cell, such as *Saccharomyces cerevisiae*. The resulting full length FGF-2 that is expressed has 146 amino acids in accordance with sequence shown at col. 6 of the '214 patent. Although the resulting FGF-2 has four cysteines, i.e., at residue positions 25, 69, 87 and 92, there are no internal disulfide linkages. [The '214 patent at col. 6, lines 59-61.] However, in the event that cross-linking occurred under oxidative conditions, it would likely occur between the two Cys residues at positions 25 and 69, respectively.

Bovine FGF-2 (bFGF-2), like the corresponding human FGF-2 (hFGF-2), is initially synthesized in vivo as a polypeptide having 155 amino acid residues. Abraham et al. "*Human Basic Fibroblast Growth Factor: Nucleotide Sequence and Genomic Organization*," EMBO J., 5(10):2523-2528 (1986). When the 146 residue bFGF-2 (SEQ ID NO: 2) of the examples is compared to the full length 155 residue bFGF-2 of Abraham, Applicants' bFGF-2 (SEQ ID NO: 2) lacks the first nine amino acid residues, i.e., Met-Ala-Ala-Gly-Ser-Ile-Thr-Thr-Leu (SEQ ID NO: 3) found at the N-terminus of Abraham's full length molecule. As discussed above, mature bFGF-2 differs from mature hFGF-2 in only two residue positions. In particular, the amino acids at residue positions 112 and 128 of the mature bFGF-2 (SEQ ID NO: 2), are Ser and Pro, respectively, whereas in corresponding mature hFGF-2 (SEQ ID NO: 6), they are Thr and Ser, respectively. In view of this substantial structural identity (i.e., greater than 97% identity) between bFGF and hFGF-2, the in vivo clinical results that are provided in the Examples, and discussed elsewhere herein on the angiogenic activity, dosage and mode of administering recombinant bFGF-2 should be directly applicable to recombinant hFGF-2 (collectively "FGF-2").

The recombinant bFGF-2 (SEQ ID NO: 2) of the Examples was purified to pharmaceutical quality (98% or greater purity) using the techniques described in detail in U.S. Pat.

No. 4,956,455 (the '455 patent), entitled "Bovine Fibroblast Growth Factor" which issued on Sep. 11, 1990 and which was incorporated herein by reference in its entirety. In particular, the first two steps employed in the purification of the recombinant bFGF-2 of Applicants' unit dose are "conventional ion-exchange and reverse phase HPLC purification steps as described previously." [The '455 patent, citing to Bolen et al., PNAS USA 81:5364-5368 (1984).] The third step, which the '455 patent refers to as the "key purification step" [see the '455 patent at col. 7, lines 5-6], is heparin-SEPHAROSE® affinity chromatography, wherein the strong heparin binding affinity of the FGF-2 is utilized to achieve several thousand-fold purification when eluting at approximately 1.4M and 1.95M NaCl [the '455 patent at col. 9, lines 20-25]. Polypeptide homogeneity was confirmed by reverse-phase high pressure liquid chromatography (RP-HPLC). Buffer exchange was achieved by SEPHADEX® G-25(M) gel filtration chromatography.

In addition to the above-described FGFs, the angiogenic agent of the compositions and the method of the present invention also comprises an "angiogenically active fragment" of any one of the above-described FGFs. In its simplest form, the angiogenic fragment is made by the removal of the N-terminal methionine, using well-known techniques for N-terminal Met removal, such as treatment with a methionine aminopeptidase. A second desirable truncation comprises an FGF without its leader sequence. Those skilled in the art recognize the leader sequence as the series of hydrophobic residues at the N-terminus of a protein that facilitate its passage through a cell membrane but that are not necessary for activity and that are not found on the mature protein.

Preferred truncations on the FGFs are determined relative to mature hFGF-2 (SEQ ID NO: 6) or the analogous bFGF-2 (SEQ ID NO: 2) having 146 residues. As a general rule, the amino acid sequence of an FGF is aligned with FGF-2 to obtain maximum homology. Portions of the FGF that extend beyond the corresponding N-terminus of the aligned FGF-2 are generally suitable for deletion without adverse effect. Likewise, portions of the FGF that extend beyond the C-terminus of the aligned FGF-2 are also capable of being deleted without adverse effect.

Fragments of FGF that are smaller than those described above are also within the scope of the present invention so long as they retain the cell-binding portions of FGF and at least one heparin-binding segment. In the case of mature FGF-2 having residues 1-146, the two putative cell-binding sites occur at residue positions 36-39 and 77-81 thereof. See Yoshida, et al., "*Genomic Sequence of hst, a Transforming Gene Encoding a Protein Homologous to Fibroblast Growth Factors and the int-2-Encoded Protein*," PNAS USA, 84:7305-7309 (October 1987) at FIG. 3. The two putative heparin-binding sites of hFGF-2 occur at residue positions 18-22 and 107-111 thereof. See Yoshida (1987) at FIG. 3. Given the substantial sequence identity between the amino acid sequences for hFGF-2 and bFGF-2, we expect that the cell-binding sites for bFGF-2 are also at residue positions 36-39 and 77-81 thereof, and that the heparin-binding sites are at residue positions 18-22 and 107-111 thereof. Consistent with the above, it is well known in the art that N-terminal truncations of bFGF-2 do not eliminate its angiogenic activity in cows. In particular, the art discloses several naturally occurring and biologically active fragments of bFGF-2 that have N-terminal truncations relative to the 146-residue mature FGF-2. An active and N-truncated FGF-2 fragment having residues 12-146 of mature FGF-2 was found in bovine liver and another active and N-truncated FGF-2 fragment, having residues 16-146 of mature FGF-2 was found in the bovine kidney, adrenal glands and testes. [See U.S. Pat. No. 5,155,214 at col. 6, lines 41-46, citing to Ueno, et al., *Biochem and Biophys Res. Comm.*, 138:580-588 (1986).] Likewise, other fragments of FGF-2 that are known to have FGF activity are FGF-2 (24-120)-OH and FGF-2 (30-110)-$NH_2$. [U.S. Pat. No. 5,155,214 at col. 6, lines 48-52.] These latter fragments retain both of the cell binding portions of FGF-2 (residues 36-39 and 77-81) and one of the heparin binding segments (residues 107-111). Accordingly, the angiogenically active fragments of an FGF typically encompass those terminally truncated fragments of an FGF that when aligned to mature FGF-2 (having residues 1-146) to maximize homology, have at least residues that correspond to residue positions 30-110 of FGF-2; more typically, at least residues that correspond to residues 18-146 of FGF-2.

In addition to the above described FGFs, the angiogenic agent of the unit dose, compositions and method of the present invention also comprises an "angiogenically active . . . mutein" thereof. By the term "angiogenically active . . . mutein," as used in conjunction with an FGF, is meant a mutated form of the naturally occurring FGF that retains at least 65% sequence identity (preferably 75%, more preferably 85%, most preferably 90% sequence identity) and at least 80% of the angiogenic activity of the respective FGF, wherein sequence identity is determined by the Smith-Waterman homology search algorithm (*Meth. Mol. Biol.* 70:173-187 (1997)) as implemented in MSPRCH program (Oxford Molecular) using an affine gap search with the following search parameters: gap open penalty of 12, and gap extension penalty of 1. Preferably, the mutations are "conservative amino acid substitutions" using L-amino acids, wherein one amino acid is replaced by another biologically similar amino acid. As previously noted, conservative amino acid substitutions are those that preserve the general charge, hydrophobicity/hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. In the case of FGF-2, an example of such a conservative amino acid substitution includes the substitution of serine for one or both of the cysteines at residue positions which are not involved in disulfide formation, such as residues 87 and 92 in mature FGF-2 (having residues 1-146). Preferably, substitutions are introduced at the N-terminus, which is not associated with angiogenic activity. However, as discussed above, conservative substitutions are suitable for introduction throughout the molecule.

One skilled in the art, using art known techniques, is able to make one or more point mutations in the DNA encoding any of the FGFs to obtain expression of an FGF polypeptide mutein (or fragment mutein) having angiogenic activity for use within the unit dose, compositions and method of the present invention. To prepare an angiogenically active mutein of an FGF, one uses standard techniques for site directed mutagenesis, as known in the art and/or as taught in Gilman, et al., *Gene*, 8:81 (1979) or Roberts, et al., *Nature*, 328:731 (1987), to introduce one or more point mutations into the cDNA that encodes the FGF.

Thus, the pharmaceutical composition of the present invention comprises an angiogenically effective amount of an angiogenic agent, in a pharmaceutically acceptable carrier, the angiogenically effective amount being in the range from about 5 ng to less than about 135,000 ng, the angiogenic agent being platelet derived growth factor (PDGF), vascular endothelial growth factor-A (VEGF-A), VEGF-D, fibroblast growth factor (FGF), or an angiogenically active fragment or mutein thereof. In a preferred embodiment, the angiogenic agent of the pharmaceutical composition is human VEGF-A, human VEGF-D, FGF or an angiogenically active fragment or mutein thereof. More preferably, the angiogenic agent of the pharmaceutical composition is an FGF, such as FGF-1, FGF-2 or FGF-5, or an angiogenically active fragment or mutein thereof. Most preferably, the angiogenic agent of the pharmaceutical composition is an FGF-2, or an angiogenically active fragment or mutein thereof.

The unit dose pharmaceutical composition of the present invention contains as its second recited component a "pharmaceutically acceptable carrier." By the term "pharmaceutically acceptable carrier" as used herein is meant any of the carriers or diluents that are well known in the art for the stabilization and/or administration of a proteinaceous medicament that does not itself induce the production of antibodies harmful to the patient receiving the composition, and which may be administered without undue toxicity. The choice of the pharmaceutically acceptable carrier and its subsequent processing enables the unit dose composition of the present invention to be provided to the treating physician in either liquid or solid form. However, the unit dose composition of the present invention is converted to liquid form before it is administered to the patient by injection into the myocardium.

When the unit dose pharmaceutical composition is in liquid form, the pharmaceutically acceptable carrier comprises a stable carrier or diluent suitable for intravenous ("IV") or intracoronary ("IC") injection or infusion. Suitable carriers or diluents for injectable or infusible solutions are nontoxic to a human recipient at the dosages and concentrations employed, and include sterile water, sugar solutions, saline solutions, protein solutions or combinations thereof.

Typically, the pharmaceutically acceptable carrier includes a buffer and one or more stabilizers, reducing agents, anti-oxidants and/or anti-oxidant chelating agents. The use of buffers, stabilizers, reducing agents, anti-oxidants and chelating agents in the preparation of protein based compositions, particularly pharmaceutical compositions, is well-known in the art. See, Wang et al., "Review of Excipients and pHs for Parenteral Products Used in the United States," J. Parent. Drug Assn., 34(6):452-462 (1980); Wang et al., "Parenteral Formulations of Proteins and Peptides: Stability and Stabilizers," J. Parent. Sci. and Tech., 42:S4-S26 (Supplement 1988); Lachman, et al., "Antioxidants and Chelating Agents as Stabilizers in Liquid Dosage Forms-Part 1," Drug and Cosmetic Industry, 102(1): 36-38, 40 and 146-148 (1968); Akers, M. J., "Antioxidants in Pharmaceutical Products," J. Parent. Sci. and Tech., 36(5):222-228 (1988); and Methods in Enzymology, Vol. XXV, Colowick and Kaplan Eds., "Reduction of Disulfide Bonds in Proteins with Dithiothreitol," by Konigsberg, pages 185-188. Suitable buffers include acetate, adipate, benzoate, citrate, lactate, maleate, phosphate, tartarate and the salts of various amino acids. See Wang (1980) at page 455. Suitable stabilizers include carbohydrates such as threlose or glycerol. Suitable reducing agents, which maintain the reduction of reduced cysteines, include dithiothreitol (DTT also known as Cleland's reagent) or dithioerythritol at 0.01% to 0.1% wt/wt; acetylcysteine or cysteine at 0.1% to 0.5% (pH 2-3); and thioglycerol at 0.1% to 0.5% (pH 3.5 to 7.0) and glutathione. See Akers (1988) at pages 225 to 226. Suitable antioxidants include sodium bisulfite, sodium sulfite, sodium metabisulfite, sodium thiosulfate, sodium formaldehyde sulfoxylate, and ascorbic acid. See Akers (1988) at pages 225. Suitable chelating agents, which chelate trace metals to prevent the trace metal catalyzed oxidation of reduced cysteines, include citrate, tartarate, ethylenediaminetetraacetic acid (EDTA) in its disodium, tetrasodium, and calcium disodium salts, and diethylenetriamine pentaacetic acid (DTPA). See e.g., Wang (1980) at pages 457-458 and 460-461, and Akers (1988) at pages 224-227. Suitable sugars include glycerol, threose, glucose, galactose and mannitol, sorbitol. A suitable protein is human serum albumin.

In liquid form, a typical unit dose pharmaceutical composition of the present invention comprises from about 5 ng to less than 135,000 ng of an angiogenic agent dissolved in from 0.1 ml to 10 ml of a pharmaceutically acceptable carrier. Because the pharmaceutical compositions of the present invention is administered via a cardiac catheter or other injection device, which has dead space, it is convenient to formulate the vial containing the pharmaceutical composition so that it contains more of the pharmaceutical composition than is to be administered to the patient. For example, when the dose of the angiogenic agent to be administered is 45 ng, the vial is formulated to contain 60-75 ng of angiogenic agent with the excess solution suitable for filling the dead space in the delivery equipment. In an alternative embodiment that does not allow for dead space, the pharmaceutical composition is loaded in the cardiac catheter in front of a pharmaceutically acceptable buffer, diluent or carrier, which is then used to deliver the appropriate amount of the one or more dosages to the one or more sites in the myocardium that are in need of angiogenesis. As discussed above, the pharmaceutically acceptable carrier for the above-described pharmaceutical compositions comprises a buffer and one or more stabilizers, reducing agents, anti-oxidants and/or anti-oxidant chelating agents.

When the angiogenic agent is an FGF and the pharmaceutically acceptable carrier is a liquid carrier, a typical pharmaceutical composition comprises about 5 to about 135,000 ng/ml, more typically 5 to 67,500 ng/ml, of an FGF or an angiogenically fragment or mutein thereof, 10 mM thioglycerol, 135 mM NaCl, 10 mM sodium citrate, and 1 mM EDTA, pH 5. A suitable diluent or flushing agent for the above-described composition is any of the above-described carriers. Typically, the diluent is the carrier solution itself, which in this example comprises 10 mM thioglycerol, 135 mM NaCl, 10 mM sodium citrate and 1 mM EDTA, pH 5.

When provided in liquid form, the unit dose pharmaceutical compositions of the present invention become unstable when stored for extended periods of time. To maximize stability and shelf life, the unit dose pharmaceutical compositions of the present invention should be stored frozen at −60° C. When thawed, the solution is stable for 6 months at refrigerated conditions. A typical vial of the unit dose pharmaceutical composition of the present invention would comprise about 1.0 to 100 ml (more typically, about 1.0 to 25 ml; most typically, about 1.0 to 10 ml) of the above described pharmaceutically acceptable carrier containing therein from about 5 ng to less than 135,000 ng of an angiogenic agent or an angiogenically fragment or mutein thereof.

In another embodiment, the unit dose pharmaceutical composition of the present invention is provided in lyophilized (freeze-dried) form. In lyophilized form, the unit dose pharmaceutical composition would be capable of being stored at refrigerated temperatures for substantially longer than 6 months without loss of therapeutic effectiveness. Lyophilization is accomplished by the rapid freeze drying under reduced pressure of a solution comprising an effective amount of the angiogenic agent dissolved in a pharmaceutically acceptable carrier. Lyophilizers, which perform the above-described lyophilization, are commercially available and readily operable by those skilled in the art. Typically, a plurality of vials, each containing therein a pharmaceutical composition (containing one or more doses) or a unit dose composition of the present invention are placed in a lyophilizer in batch and subjected to cooling and reduced pressure until all liquid carrier is removed. Prior to administration to a patient, the lyophilized product is reconstituted to a known concentration, preferably in its own vial, with an appropriate sterile aqueous diluent, typically 0.9% (or less) sterile saline solution, or some other pharmaceutically acceptable carrier. Depending upon the need for angiogenesis as assessed by the treating physician, a unit dose comprising from 5 ng to less than 135,000 ng, typically from about 5 ng to about 67,500 ng, of an angiogenic agent are administered as a single injection or as a series of injections, typically from 2 to 40 injections, into the ischemic myocardium in need of angiogenesis.

Figure 5:
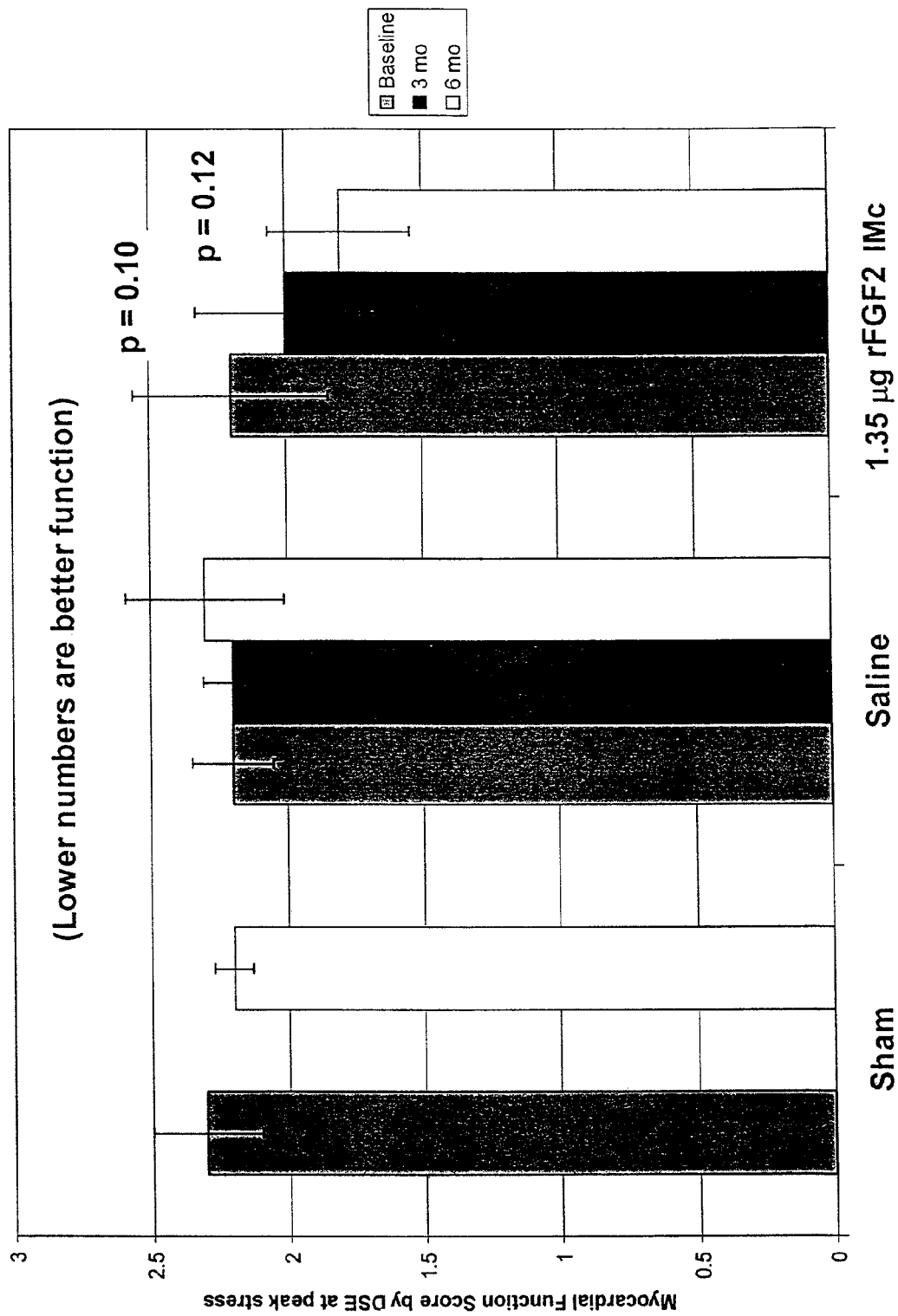
FIG. 5 is a bar graph comparing myocardial function by dolbutamine stress echocardiogram in the pig model of the hibernating myocardium at baseline, 3 months and 6 months following sham administration; saline; and a unit dose containing 1.35 µg of rFGF-2 (SEQ ID NO: 2).
Figure 6:
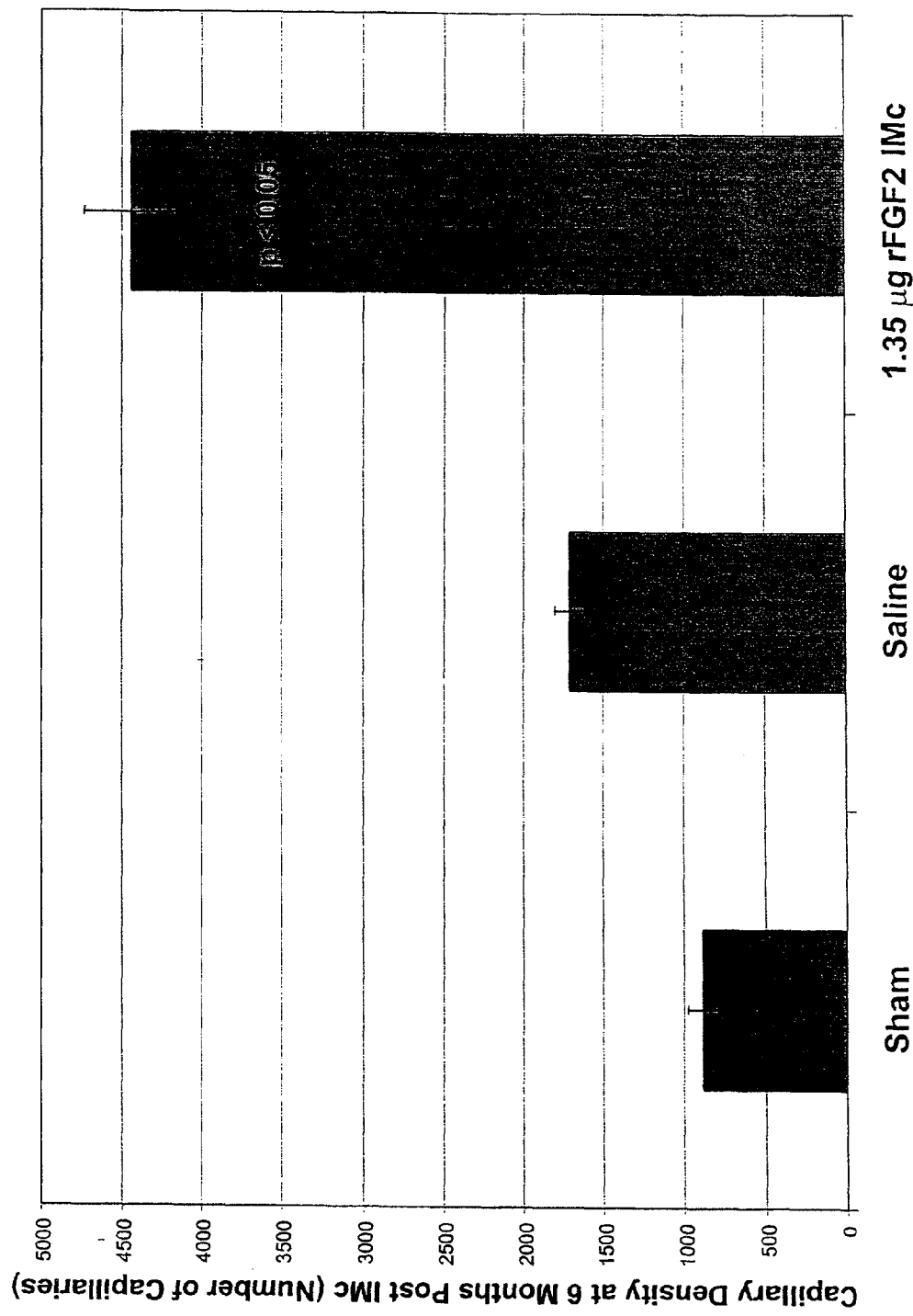
FIG. 6 is a bar graph comparing capillary density (# of vessels) in the ischemic myocardial tissue (downstream from the 90% occlusion in the LCx) in the pig model of the hibernating myocardium at 6 months following sham administration; saline; and a unit dose containing 1.35 µg of rFGF-2 (SEQ ID NO: 2).
Figure 11:
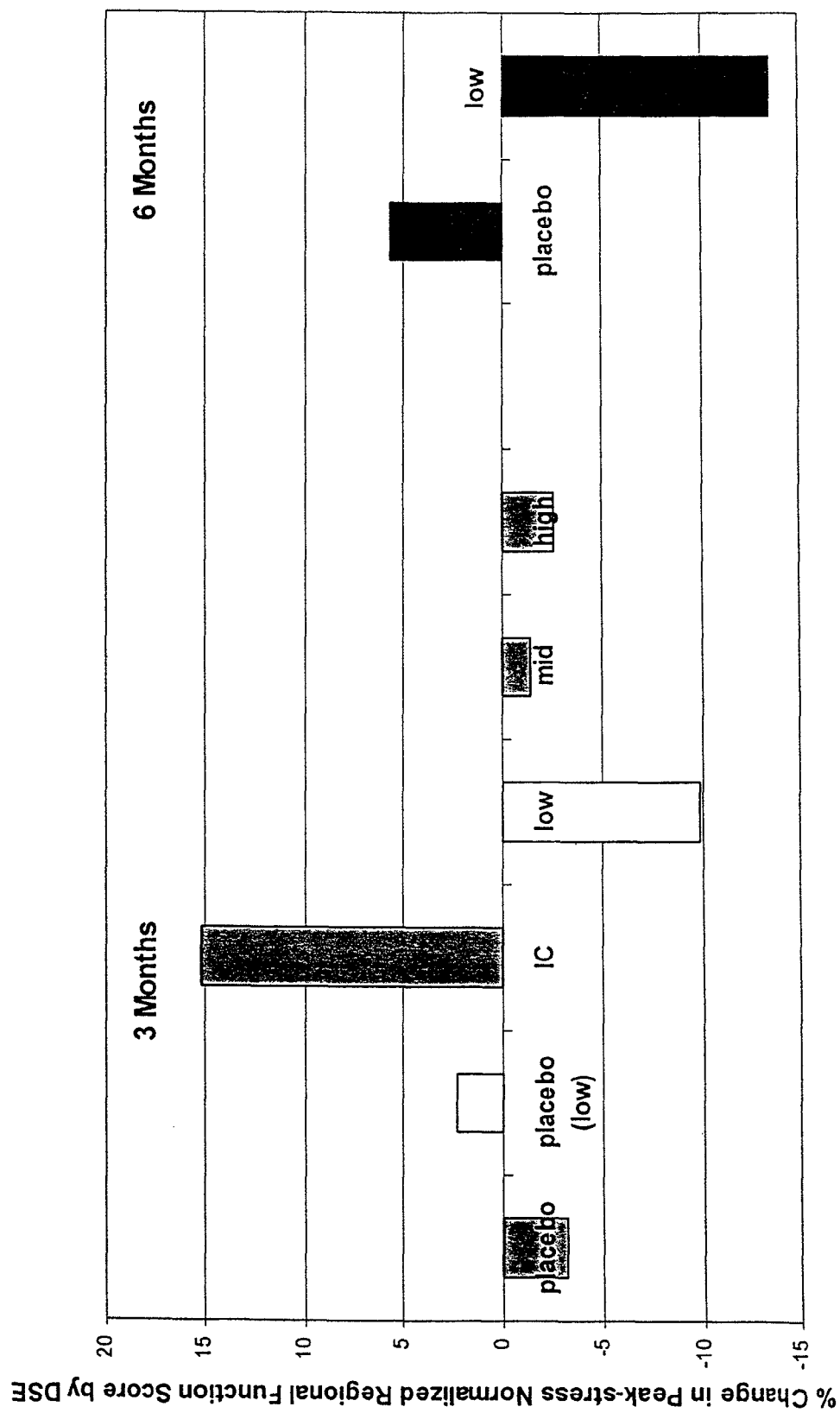
FIG. 11 is a bar graph comparing the % change in peak-stress normalized regional function score by DSE at 3 months and 6 months after treatment with placebo, or with the "mid" dose (0.6 µg/kg (13.5 µg)) of FGF-2 (SEQ ID NO: 2) IC in the ameroid pig model, or with the "low" dose (0.06 µg/kg (1.35 µg)) of FGF-2 (SEQ ID NO: 2) IMc, or with the "mid" dose (0.6 µg/kg (13.5 µg)) of FGF-2 (SEQ ID NO: 2) IMc, or with the "high" dose (6.0 µg/kg (135 µg)) of FGF-2 (SEQ ID NO: 2) IMc in the pig model of the hibernating myocardium.

In its third aspect, the present invention is directed to a method for inducing angiogenesis (or increasing vascular perfusion, or increasing vascular density or increasing regional myocardial function as measured by DSE) in a heart of a patient, comprising administering an effective amount of an angiogenic agent directly into the myocardium of said patient in one or more areas in need of angiogenesis, the effective amount of angiogenic agent being from about 5 ng to less than 135,000 ng of said angiogenic agent. Typically, the effective amount of angiogenic agent is from 5 ng to 67,500 ng of said angiogenic agent. Preferably, the patient is a human patient. More preferably, the human patient has symptoms of a coronary artery disease (CAD) or a myocardial infarction (MI). The terms "vascular perfusion" and "vascular density," as referenced above, are objective measures of angiogenesis. Increases in "vascular perfusion" and "vascular density" in response to administering an angiogenic agent according to the method of the present invention are shown in FIGS. 4 and 6-8 herein. Increases in regional cardiac function produced by administering unit doses of an angiogenic agent in accordance with the method of the present invention are shown in FIGS. 5 and 11.

In the above-described method, the angiogenic agent is a member selected from the group PDGF, VEGF-A, VEGF-D, TGF-β1, FGF, or an angiogenically active mutein or fragment thereof. Preferably, the angiogenic agent is VEGF-A, VEGF-D or an FGF or an angiogenically active fragment or mutein thereof. More preferably, the angiogenic agent is an FGF, such as FGF-1, FGF-2 or FGF-5, or an angiogenically active fragment or mutein thereof. Most preferably, the angiogenic agent is FGF-2, or an angiogenically active fragment or mutein thereof.

In the above-described method, the angiogenic agent is delivered to the myocardium of a patient in need of angiogenesis using any one of the art known techniques for myocardium drug delivery. The need of a patient for angiogenesis is evaluated by the treating physician using conventional evaluation techniques such as coronary angiography, MRI and the like. In its simplest embodiment, a needle attached to a drug delivery device, such as a syringe, is stereotactically directed from outside the body through the chest cavity and the pericardium to an area of the myocardium in need of angiogenesis for delivery therein of an effective amount of an angiogenic agent. Once a dosage has been delivered to the myocardium, the needle is withdrawn or repositioned to one or more sites on the myocardium for delivery of the angiogenic agent. Regardless of the number of injection sites in the myocardium (typically, 2-40), the total amount of angiogenic agent that is delivered is within the range of about 5 ng to less than 135,000 ng, more typically, from 5 ng to 67,500 ng. Because the myocardium contracts after delivery of the angiogenic agent, it is believed that some small amount of the dose of angiogenic agent would be forced back out of the myocardium, via the needle hole, and into the pericardial space, where momentarily, it would provide a localized concentration at the area of need, and subsequently upon mixing in the pericardial fluid, it would continue to bathe the myocardium in angiogenic agent for a prolonged period of time. These effects would only serve to enhance the effect of the IMc dose of the angiogenic agent of the present invention. Thus, in another aspect, the present invention is directed to a method for inducing angiogenesis in the heart of a patient, comprising administering a unit dose of angiogenic agent directly into the myocardium of a patient in need of angiogenesis and allowing a residual amount of said angiogenic agent to enter into the pericardial space surrounding said myocardium.

In another embodiment of the method for inducing angiogenesis (or increasing vascular perfusion, or increasing vascular density or increasing regional myocardial function as measured by DSE), the unit dose of angiogenic agent is delivered directly into the myocardium from a device having its proximal end outside the body and its distal end positioned within a coronary vein, a coronary artery or a chamber of the heart. A plurality of devices for delivering medicaments by injection into the myocardium from a coronary vein, coronary artery or from a chamber of the heart are well known in the art. Examples of such devices include cardiac catheters having a retractable needle at the distal end, which upon being positioned adjacent an area of the myocardium in need of angiogenesis, can project the needle into the myocardium for delivery of a predetermined amount of medicament. In the present method, such a device delivers an ultra-low dose of angiogenic agent of the present invention to an area of the myocardium in need of angiogenesis. After delivery of the angiogenic agent, the needle is retracted into the distal end, and the distal end of the device is repositioned adjacent a second area of the myocardium in need of angiogenesis, whereupon the needle is again projected into the myocardium and an ultra-low dose of the angiogenic agent is delivered. This procedure is then repeated as often as needed. The needle of the above-described embodiment is also replaceable by a laser, such as used in laser angioplasty, wherein the laser is used to bore a channel into the area of the myocardium in need of angiogenesis, and an orifice adjacent the laser delivers the ultra-low dose of the angiogenic agent directly into the channel. This latter device is described in WO 98/05307, entitled "Transmural Drug Delivery Method and Apparatus," and in corresponding U.S. Ser. No. 08/906,991, filed Aug. 6, 1997, and assigned to LocalMed, Palo Alto Calif. Similar cardiac catheters suitable for drug delivery are commercially available from manufacturers such as ACS, Guidant, Angion, and LocalMed.

Other devices that are suitable for delivery of a medicament to the myocardium include delivery devices having a series of drug delivery pores positioned on the outer surface of the balloon portion of a conventional balloon cardiac catheter, which upon inflating the balloon, bring the drug delivery pores in direct contact with the vascular epithelium. The medicament is then delivered through the drug delivery pores under pressure which forces the medicament past the epithelium and into the underlying myocardium. Devices of this type are disclosed in U.S. Pat. No. 5,810,767, entitled "Method and Apparatus for Pressurized Intraluminal Drug Delivery" which issued on Sep. 22, 1998; and in U.S. Pat. No. 5,713,860, entitled "Intravascular Catheter with Infusion Array" which issued on Feb. 3, 1998; and in pending application WO 97/23256, entitled "Localized Intravascular Delivery of Growth Factors for Promotion of Angiogenesis" and corresponding U.S. Ser. No. 08/753,224, now pending.

The above-described cardiac catheters are utilized using standard techniques for cardiac catheter use. Typically, the treating physician inserts the distal end of the catheter into the femoral or subclavian artery of the patient in need of coronary angiogenesis, and while visualizing the catheter, guides the distal end into a coronary artery, vein or chamber of the heart that is proximate to the area of the heart in need of angiogenesis. The distal end of the catheter is positioned adjacent an area of the myocardium in need of angiogenesis and used as described above to deliver an ultra-low dose, i.e., an angiogenically effective amount, of an angiogenic agent. In accordance with the present invention, an angiogenically effective amount of an angiogenic agent comprises from about 5 ng to less than 135,000 ng, typically from 5 ng to 67,500 ng, of the angiogenic agent. Although an angiogenically effective amount of the angiogenic agent is injected into the myocardium with each repositioning of the delivery device, the total amount of angiogenic agent that is injected is less than 135,000 ng (i.e., less than 135 µg).

In other embodiments of the above-described method, one or more doses of the angiogenic agent are administered to the appropriate areas of myocardium for several days, over a series of alternating days, for weeks or over a series of alternating weeks. However, the total amount of angiogenic agent that is injected in one treatment regime is less than 135,000 ng (i.e., less than 135 µg).

The diseases most often associated with a need for coronary angiogenesis are coronary artery disease (CAD), i.e., a disease in which one or more coronary arteries in the patient have become partially occluded, and myocardial infarction (MI), i.e., a disease in which a coronary artery has become sufficiently occluded to cause the necrosis of the downstream myocardial tissue that relied on the artery for oxygenated blood. Thus in another aspect, the present invention is also directed to a method for treating a patient for CAD or MI, comprising administering an effective amount of an angiogenic agent directly into the myocardium of said patient in one or more areas in need of angiogenesis, the effective amount of angiogenic agent being from about 5 ng to less than about 135,000 ng of said angiogenic agent. Typically, the effective amount of angiogenic agent is from about 5 ng to about 67,500 ng of said angiogenic agent. Preferably, the patient is a human patient.

The active agent in the Applicants' above described pharmaceutical composition, unit dose, or methods is preferably a recombinant FGF or an angiogenically active fragment or mutein thereof. More preferably, the angiogenic agent is FGF-2 or an angiogenically active fragment or mutein thereof.

Clinical efficacy of the ultra-low dose of angiogenic agent of the present invention was established in a series of steps wherein angiogenic agent was administered to animals and humans in decreasingly smaller amounts. The angiogenic agent of these clinical studies was recombinant mature bFGF-2 having 146 residues, as disclosed in U.S. Pat. No. 4,956,455 (Baird), and referred to hereinafter as rbFGF-2. As preliminary evidence of the clinical efficacy of the ultra-low dosages of angiogenic agents used herein, human patients exhibiting symptoms of severe CAD, who remained symptomatic despite optimal medical management, were administered decreasing dosages of rbFGF-2 by intracoronary infusion via a cardiac catheter.

TABLE 2

COMPARISON OF QUALITY OF LIFE BEFORE AND 57 DAYS AFTER IC FGF-2

| SEATTLE ANGINA QUESTIONNAIRE (SAQ) SUBSCALES | BASELINE (PRE FGF-2) MEAN SCORE ± SD | 57 DAYS POST FGF-2 MEAN SCORE ± SD | MEAN CHANGE[1] | p VALUE | n |
|---|---|---|---|---|---|
| Exertional Capacity | 55 ± 23 | 68 ± 25 | 13* | 0.02 | 28 |
| Angina Frequency | 42 ± 32 | 66 ± 28 | 24* | <0.001 | 28 |
| Angina Stability | 46 ± 26 | 82 ± 20 | 36* | <0.001 | 27 |
| Disease Perception | 40 ± 21 | 61 ± 26 | 19* | <0.001 | 28 |
| Treatment Satisfaction | 74 ± 24 | 88 ± 16 | 14* | 0.002 | 28 |

*Significantly different from baseline to fifty-seven days.
[1] A mean change of 8 points or more is considered clinically significant.

TABLE 3

IMPROVEMENTS IN THE QUALITY OF LIFE AT DAY 57 (POST IC rFGF-2) AT LOWER AND HIGHER DOSES

| SEATTLE ANGINA QUESTIONNAIRE (SAQ) SUBSCALES Subscales | DOSE <2 µg/kg IC rFGF-2 (n = 7) Mean Change In Score (Day 57 Score-Screen Score) | DOSE >2 µg/kg IC rFGF-2 (n = 8) Mean Change In Score (Day 57 Score-Screen Score) | INDEPENDENT SAMPLES | T-TEST |
|---|---|---|---|---|
| Exertional Capacity | 12.30 (23.3) | 15.98 (28.7) | t = −.27 | p = .79 |
| Disease Perception | 26.19 (26.9) | 24.47 (21.2) | t = .14 | p = .89 |
| Treatment Satisfaction | 22.32 (27.7) | 10.93 (17.3) | t = .97 | p = .35 |
| Angina Frequency | 28.57 (27.3) | 13.75 (22.6) | t = 1.15 | p = .27 |
| Angina Stability | 58.13 (12.9) | 32.14 (34.5) | t = 1.75 | p = .108 |

1. Possible range for each subscale is 0 to 100 with higher scores indicating better quality of life.
2. Standard deviation noted in parentheses.

TABLE 4

MEAN DATA AND RESULTS AS A FUNCTION OF TIME AND DOSE

|  | BASELINE | 30 DAY | 60 DAY |
|---|---|---|---|
| Angina Class | 2.6 ± 0.7 | 1.4 ± 0.9 *** | 1.2 ± 0.8 *** |
| Exercise Time (min.) | 8.5 ± 2.6 | 9.4 ± 1.9 *** | 10.0 ± 2.5 ** |
| LV EF (%) | 47.4 ± 12.3 | 47.4 ± 10.6 | 48.6 ± 11.0 |
| Target Wall Motion (%) | 15.4 ± 10.1 | 23.5 ± 12.0 * | 24.1 ± 10.1 ** |
| Target Wall Thickening (%) | 28.7 ± 14.0 | 34.7 ± 14.1 | 45.9 ± 11.7 ** |
| Delayed Arrival Zone (% LV) | 18.9 ± 8.3 | 7.1 ± 3.6 *** | 1.82 ± 2.4 *** |

\* = $p < 0.05$
\*\* = $p < 0.01$
\*\*\* = $p < 0.001$ (2-tailed, paired)

(See Example 3) The doses of FGF-2 administered (and number of patients) were 0.33 µg/kg (n=4), 0.65 µg/kg (n=4), 2.0 µg/kg (n=8), 6.0 µg/kg (n=4), 12.0 µg/kg (n=4), 24 µg/kg (n=8), 36 µg/kg (n=10) and 48 µg/kg (n=10). Angina frequency and quality of life was assessed by the Seattle Angina Questionnaire (SAQ) at a baseline (before FGF-2 administration) and at about 60 days after FGF-2 administration. Exercise tolerance time (ETT) was assessed by the threadmill test. Rest/exercise nuclear perfusion and gated sestamibi-determined rest ejection fraction (EF), and magnetic resonance imaging (MRI) were assessed at baseline, and at 30 days and 60 days post FGF-2 administration. Other end points that were evaluated included MRI (to objectively measure ejection fraction (EF), normal wall motion (NWM), targeted wall motion (TWM), normal wall thickness (NWT), targeted wall thickness (TWT), ischemic area zone and collateral extent). See Tables 2-4, respectively. The patients exhibited significant clinical improvements to all dosages of the FGF-2 that were administered IC. In particular, Table 3 discloses that the patients receiving the lowest dosages of FGF-2 (less than 2 µg/kg) exhibited better results in four of the five criteria assessed than did the patients receiving the higher dosages of FGF-2 (greater than 2 µg/kg). The above described method for treating CAD, when assessed by the standard objective criterion employed in the art (i.e., ETT), provided an unexpectedly superior increase of one and a half to two minutes in the treated patient's ETT. This compares exceptionally well when compared to the increase of 30 seconds that is deemed clinically significant for the current mode of treatment, i.e., angioplasty.

A major side effect reported in the art for the angiogenic agents of the present invention is acute hypotension. This is due to the known effect of many of the angiogenic agents as a vasodilator. However, no adverse hypotensive effects were observed following administration, alone or in series, of any of the ultra-low dosages of angiogenic agent within the scope of the present invention.

In testing the angiogenic agents for angiogenic activity in vivo, fifty-two (52) human patients diagnosed with CAD, who satisfied the criteria of Example 2 herein, were administered a unit dose of 0.33 µg/kg to 48 µg/kg of the FGF-2 by intracoronary (IC) infusion over about a 20 minute period. In particular, in the 52 patients, a coronary (cardiac) catheter was inserted into an artery (e.g., femoral or subclavian) of the patient in need of treatment and the catheter was pushed forward with visualization, until it was positioned in the appropriate coronary artery of the patient to be treated. Using standard precautions for maintaining a clear line, the angiogenic agent was administered by infusing the unit dose substantially continuously over a period of 10 to 30 minutes. The 52 treated patients were then assessed by the Seattle Angina Questionnaire, which provides an assessment based upon a mixed combination of objective and subjective criteria. See Table 2. The Seattle Angina Questionnaire is a validated, disease-specific instrument with the following five subscales that are assessed both before and after treatment: 1) "exertional capacity"=limitation of physical activity; 2) "disease perception"=worry about MI; 3) "treatment satisfaction"; 4) "angina frequency"=number of episodes and sublingual nitroglycerin usage; and 5) "angina stability"=number of episodes with most strenuous physical activity. The possible range for each of the five subscales is 0 to 100 with the higher scores indicating a better quality of life. Moreover, a mean change of 8 points or more between the mean baseline scores (before treatment) and the post-treatment scores is recognized as being "clinically significant." Table 2 reports that the 28 patients, who were pretested and then administered a single unit dose of 0.33 µg/kg to 24 µg/kg of rbFGF-2 by IC infusion, exhibited a mean score increase of 13 to 36 points for the five "quality of life" criteria assessed by the "Seattle Angina Questionnaire." See Table 2 herein. These 13 to 36 point increases were about 1.6 to 4.5 times greater than the 8 point change which is recognized in the art as being "clinically significant" in alternative modes of treatment. See Table 2 herein. Moreover, when the combined results for the first 15 patients of Table 2 were broken down between low dose (less than or equal to 2 µg/kg) and high (more than 2 µg/kg) doses of rbFGF-2, and assessed by the "Seattle Angina Questionnaire," both doses were found to provide increased scores that ranged from about 12.3 to 58.1 and about 10.9 to 32.1, respectively. See Table 3 herein. The increased scores were about 1.4 to 7.2 times greater than the 8 point change which is considered to be "clinically significant" in alternative modes of treatment.

In the same Phase I trial, fifty-two human patients who were diagnosed with CAD and who satisfied the criteria of Example 2 herein, were administered IC a single unit dose of 0.33 µg/kg to 48 µg/kg of rbFGF-2. The maximum tolerated dose was defined as 36 µg/kg by severe but transient hypotension that was observed in 2 out of 10 patients at the next higher dose of 48 µg/kg. At one of the sites, the hearts of 23 patients were assessed both before ("baseline") and 30 and 60 days after treatment by magnetic resonance imaging (MRI) for objective signs of improved coronary sufficiency. Among the objective criteria assessed by MRI are the following: 1) left ventricular (LV) ejection fraction (EF); 2) normal wall thickness (NWT); 3) normal wall motion (NWM); 4) collateral extent; 5) ischemic area zone; 6) targeted wall thickness (TWT); 7) targeted wall motion (TWM); and 8) perfusion or delayed arrival zone (% LV). The patients were also assessed for angina, treadmill exercise duration, rest/exercise nuclear perfusion. The results are summarized in Table 4. Table 4 reflects that the baseline angina class decreased from 2.6 to 1.4 and 1.2 at 30 and 60 days, respectively post IC FGF-2. The mean treadmill exercise time increased from a baseline of 8.5 minutes to 9.4 and 10.0 minutes at 30 and 60 days, respectively, post treatment. No significant difference was observed in the left ventricular ejection fraction (LV EF). However, the target wall motion increased significantly, moving from a baseline of 15.4% to 23.5% (day 30) and 24.1% (day 60) post FGF-2 treatment. Likewise the target wall thickening increased significantly from a baseline of 28.7% to 34.7% (day 30) and 45.9% (day 60) post FGF-2 treatment. There was also a significant increase in perfusion, as measured by a decrease in the delayed arrival zone (% LV), with the delayed arrival zone decreasing from a baseline of 18.9% to 7.1% (day 30) and 1.82% (day 60) post FGF-2 treatment. Thus, providing CAD patients with a single IC infusion of an angiogenic agent, such as FGF-2, provided the patients with a significant physical improvement as objectively measured by MRI and other conventional criteria.

Pharmacokinetics and Metabolism

The kidneys and liver are the major organs for the elimination of the angiogenic agents. In particular, the kidneys have a protein cutoff of about 60 kD and thus retain serum albumin (MW 60 kD). However, all the angiogenic agents of the present invention have a molecular weight less than 40 kD. FGF-2, the angiogenic agent of the present Examples, has a molecular weight of about 16 kD. Accordingly, renal excretion is to be expected. In a radiolabelled biodistribution study of commercially available bFGF-2, both the liver and the kidney were shown to contain high counts of the radiolabelled bFGF-2 at 1 hour after IV or IC injection. In a published study, wherein another recombinant iodinated form of bFGF-2 was given to rats, the liver was identified as the major organ of elimination. Whalen et al., "*The Fate of Intravenously Administered bFGF and the Effect of Heparin*," Growth Factors, 1:157-164 (1989). More particularly, it is known that FGF-2 binds in the general circulation to $\alpha_2$-macroglobulin and that this complex is internalized by receptors on the Kupffer cells. Whalen et al. (1989) and LaMarre et al., "*Cytokine Binding and Clearance Properties of Proteinase-Activated Alpha-2-Macroglobulins*," Lab. Invest., 65:3-14 (1991). Labelled FGF-2 fragments were not found in the plasma, but they were found in the urine and corresponded in size to intracellular breakdown products. When FGF-2 was administered in combination with heparin, the renal excretion of FGF-2 was increased. Whalen et al. (1989). The FGF-2 molecule, which is cationic when not complexed with heparin, is likely repelled by the cationic heparin sulfate of the glomerular basement membrane. The FGF-2/heparin complex is more neutrally charged, and therefore is more easily filtered and excreted by the kidney.

The pharmacokinetics of FGF-2 were determined after intravenous (IV) and intracoronary (IC) administration in domestic Yorkshire pigs, after IV dosing in Sprague Dawley ("SD") rats, and after IC administration in CAD human patients. In all species, the rFGF-2 plasma concentrations after IV and/or IC injection followed a biexponential curve with an initial steep slope and considerable decrease over several log scales (the distribution phase) during the first hour, followed by a more moderate decline (the elimination phase). FIG. 1 provides a plasma concentration versus time curve showing these phases in humans after IC administration of recombinant mature bFGF-2 (146 residues) as a function of the following doses: 0.33 µg/kg, 0.65 µg/kg, 2 µg/kg, 6 µg/kg, 12 µg/kg and 24 µg/kg of lean body mass (LBM). The plasma concentrations of bFGF-2 were determined by a commercially available ELISA (R&D Systems, Minneapolis Minn.) that was marketed for analysis of human FGF-2. The ELISA assay for hFGF-2 showed 100% cross-reactivity with the recombinant mature bFGF-2. Other members of the FGF family, as well as many other cytokines, were not detected by this assay. Also, heparin does not interfere with the assay.

The design of these pharmokinetic studies, pharmacokinetic parameters, and conclusions are listed in Tables 5 and 6 for studies in pigs and rats, respectively. The reader is referred to these tables for the specific details. However, among the points to be noted are that the half-life ($T_{1/2}$) was 2.8±0.8 to 3.5 hours following a single IC infusion for the single component model for animals having a clearance (CL) of 702±311 to 609±350 ml/hr/kg. The results of this study

TABLE 5

PHARMACOKINETICS (PK) AND PHARMACODYNAMICS OF rFGF-2 IN PIGS

| ANIMALS | DOSING REGIMEN | PK PARAMETERS | RESULTS |
|---|---|---|---|
| Domestic Yorkshire Pigs under general anesthesia (n = 13; 30 ± 5 kg) | 2-20 µg/kg IV bolus 2-20 µg/kg IC bolus 20 µg/kg by 10 min IC infusion 70 U/kg heparin~15 min before rFGF-2 | CL = 702 ± 311 mL/hr/kg T ½ = 2.8 ± 0.8 hr. | Systemic PK identical between IV and IC route Fast distribution phase Dose-linearity Transient decreases of MAP |
| Domestic Yorkshire Pigs under general anesthesia (n = 17; 26 ± 4 kg) | 0.65-6.5 µg/kg by 5-mm IC infusion 70 U/kg heparin~15 min before rFGF-2 | CL = 609 ± 350 ml/hr/kg T ½ = ~3.5 hr 3-Comp. Model: T ½α = 1.5 min T ½β = 17 min T ½γ = 6.6 hr CL = 580 ml/hr/kg $V_t$ = 55 ml/kg $V_{56}$ = 523 ml/kg | No gender difference in PK Biphasic decline of plasma rFGF-2 Dose-linearity $V_t$ equal to - plasma volume $V_{56}$ equal to - 10-fold plasma volume Magnitude and duration of MAP decrease correlated with rFGF-2 dose and peak plasma level |
| Domestic Yorkshire Pigs under general anesthesia (n = 6; 25 ± 5 kg) | 6.5 µg/kg weekly by 5 min IV infusion for 6 weeks 70 U/kg heparin 10 min before rFGF-2 (n = 3), or rFGF-2 alone (n = 3) | Without Heparin (Doses 1-6): T½ = 2-6 hr CL = 777-2749 ml/hr/kg $V_{56}$ = 871-12,500 ml/kg With Heparin (Doses 1-6): T½ - 2-3 hr CL = 235-347 ml/hr/kg $V_{56}$ = 71-153 ml/kg | The rFGF-2 distribution phase was less steep, the volume of distribution smaller, and clearance was slower with heparin-pretreatment Binding of rFGF-2 to circulating heparin appears to decrease biodistribution and elimination Both volume and clearance of rFGF-2 increased at later doses (potential receptor upregulation), but more so in the absence of heparin Magnitude and duration of MAP decreases were similar with or without heparin |

TABLE 6

PHARMACOKINETICS (PK) OF rFGF-2 IN RATS

| ANIMALS | DOSING REGIMEN | PK PARAMETERS | RESULTS |
|---|---|---|---|
| Conscious SD rats (n = 18; 322 ± 93 g) | 3-100 µg/kg bolus IV injection | $T^{1/2}$ = 1.1 ± 0.51 hr<br>CL = 4480 ± 2700 ml/hr/kg<br>$V_{ss}$ = 1924 ± 1254 ml/kg | Fast distribution phase<br>Apparent dose-linearity |
| Conscious SD rats (n - 54; 149 ± 12 g) | 30-300 µg/kg weekly by bolus IV injection for 6 weeks<br>No heparin pretreatment | $T^{1/2}$ = 1.4 ± 0.13 hr<br>CL = 1691 ± 169 ml/hr/kg<br>$V_{ss}$ = 1942 ± 358 ml/kg | Time-invariant PK; plasma profiles, PK parameters and AUCs were similar over time<br>Dose linearity |
| Conscious SD rats (27 males; 381 ± 48 g; 20 females; 268 ± 22 g) | | Time-Averaged PK Parameters:<br>$T^{1/2}$ hr. / CL ml/hr/kg / $V_{ss}$ ml/kg | In all cases, heparin increased the rFGF-2 plasma levels<br>Both volume of distribution and clearance of rFGF-2 were smaller with heparin<br>Greatest changes on CL and $V_{ss}$ were observed when heparin was administered immediately prior to rFGF-2 |
| | 30 µg/kg bolus IV injection<br>No heparin | 0.75 / 4332 / 2389<br>0.91 / 1728 / 844 | |
| | 40 U/kg IV Heparin:<br>at ~15 min<br>just prior to rFGF-2<br>at +15 min<br>at +3 hr. | 1.3 / 516 / 147<br>1.2 / 1158 / 626<br>0.93 / 1338 / 1351 | | show that the pharmacokinetics of the rFGF-2 were substantially identical regardless of whether the animals were dosed via the IC or IV routes. See Table 5. Among the other pharmacokinetic results to be taken from Tables 5 and 6 of these studies is that there is a fast distribution phase followed by a more moderate elimination phase, and dose linearity as reported in FIG. 1 for humans. Also, there were no gender differences. Further, the three compartment model was analyzed for pigs receiving 70 U/kg of heparin approximately ("~") 15 minutes before receiving 0.65-6.5 µg/kg by 5-10 minute IC infusion. The half lives ($T_{1/2\alpha}$, $T_{1/2\beta}$ and $T_{1/2\gamma}$) for the three compartments were 1.5 minutes, 17 minutes, and 6.6 hours, respectively. In these animals, the initial volume ("$V_1$") was approximately the plasma volume, and the steady state volume ("$V_{ss}$") was approximately 10-fold the plasma volume. See Table 5. In pigs, the binding of rFGF-2 to circulating heparin appears to decrease biodistribution and elimination. Likewise, in rats, both the volume of distribution and the clearance of rFGF-2 were smaller when heparin was administered. See Table 6. Further, the greatest and most favorable changes on clearance of FGF-2 were found when heparin was administered within ±15 minutes, preferably immediately prior to rFGF-2 IC infusion. See Table 6.

The pharmacokinetics of the FGF-2 was studied in humans, diagnosed with CAD despite optimal medical management, in a Phase I clinical study supporting this filing. The doses of rbFGF-2 employed in that Phase I study were 0.33 µg/kg, 0.65 µg/kg, 2 µg/kg, 6 µg/kg, 12 µg/kg, and 24 µg/kg of lean body mass (LBM), and all doses were administered by a 20 minute IC infusion (10 minutes into each of two patent coronary vessels) after pretreating the patient with 40 U/kg heparin which was administered IV or IC 1-95 minutes before rbFGF-2 infusion. FIGS. 1-3 herein summarize the data underlying those results. In particular, FIG. 1 is a plot of the mean FGF-2 plasma concentration versus time (hours) for the six different doses of rbFGF-2 administered by IC infusion as described above over a 20 minute period. FIG. 1 shows dose linearity and a biphasic plasma level decline, i.e., a fast distribution phase during the first hour, followed by an elimination phase with $T_{1/2}$ of 1.9±2.2 hours. The dose linearity is more readily seen in FIG. 2, which is a plot of the individual patient FGF-2 area under the curve (AUC) in pg·hr/ml for FIG. 1 for each of the six doses of rbFGF-2 administered. FIG. 3 is a plot individual human patient FGF-2 dose normalized AUCs versus time of heparin dose in "minutes prior to rFGF-2 infusion" and shows the influence of timing of heparin administration on FGF-2 AUC. FIG. 3 shows that the greatest AUC/dose was achieved when an effective amount of a glycosoaminoglycan, such as heparin, was preadministered within 30 minutes or less of IC rFGF-2 infusion, more preferably within 20 minutes or less of IC rFGF-2 infusion. Typically, an effective amount of a glycosoaminoglycan is 40-70 U/kg heparin. These pharmacokinetic results are summarized in Table 7 herein.

The rFGF-2 distribution phase was less steep with heparin, the volume of distribution smaller, and the clearance slower, as compared to rFGF-2 without heparin. It appears that the complex of rFGF-2 with circulating heparin decreases the biodistribution and elimination of rFGF-2. Although the binding of FGF-2 to heparin-like structures is strong (dissociation constant $\sim 2\times 10^{-9}$ M), the binding of FGF-2 to the FGF-2 receptor is approximately two orders of magnitude higher (dissociation constant $\sim 2\times 10^{-11}$ M). Moscatelli et al., (1991). In addition, the complexation of the rFGF-2 with a glycosoaminoglycan, such as a heparin, might increase signal transduction and mitogenesis, and/or protect the rFGF-2 from enzymatic degradation. Using a validated and art-accepted model of hibernating myocardium, ten (10) miniswine underwent 90% left circumflex (LCx) coronary stenosis. For validation, see e.g., Yanagisawa-Miwa, et al., "*Salvage of Infarcted Myocardium by Angiogenesic Action of Basic Fibroblast Growth Factor,*" Science, 257:1401-1403 (1992); Banai et al., "*Angiogenic-Induced Enhancement of Collateral Blood Flow to Ischemic Myocardium by Vascular Endothelial Growth Factor in Dogs,*" Circulation, 89(5):2183-2189 (May 1994); and Unger, et al., "*Basic fibroblast growth factor enhances myocardial collateral flow in a canine model,*" Am. J. Physiol., 266 (Heart Circ. Physiol. 35): H1588-H1595 (1994). One month later, a baseline positron emission tomography (PET) and dobutamine stress echocardiography were performed on the animals. The animals were then randomized and treated with 30 injections in the LCx region of either 100 µl carrier (n=5) or rbFGF-2 (45 ng/injection; total dose 1,350 ng) (n=5) in carrier. In the above injections, the carrier was a sterile aqueous solution comprising 10 mM thioglycerol, 135 mM NaCl, 10 mM sodium citrate and 1 mM EDTA, pH 5. In the five animals that received the injections of FGF-2 in their myocardium, the LCx region myocardial blood flow (MBF) at rest, as measured by PET, increased from 61.3±4.4% of non-ischemic septal values at baseline (day 0) to 82.8±3.1% at 6 months postoperatively (p<0.001). The wall motion score index (WMSI) at rest for the LCx region was 2.4±0.2 at baseline and improved to 2.2±0.2 (p=0.08 vs baseline) at six months. Likewise, WMSI for the LCx region at peak stress was 2.2±0.4 at baseline (day 0) and decreased to 1.8±0.3 (p=0.05) at six months. There was no significant change in MBF or in the resting or stress WMSI in the vehicle treated animals at any time point. Western blot analysis of tissue samples taken from the treated chronically ischemic regions revealed significantly greater upregulation of VEGF in the chronically ischemic regions treated with rFGF-2 versus that observed in the chronically ischemic regions treated with vehicle (p<0.05).

Thus, in this validated model of a patient in need of angiogenesis, the direct intramyocardial injection of ultra-low dose of angiogenic agent, such as FGF-2, improved MBF and contractile reserve in the treated regions of the myocardium. Accordingly, an ultra-low dose of angiogenic agent represents a viable method for inducing angiogenesis and a viable alternative therapy for the treatment of CAD and/or MI.

Examples 1-6, which follow, provide more details on the selection criterion and on the Phase I clinical trial for IC FGF-2 that gave rise to the preliminary data discussed above. Example 7 discloses data on the ultra-low dose pharmaceutical composition and method of the present invention and its use to induce coronary angiogenesis in patients (miniswine) in a model system for coronary artery disease and myocardial infarction.

Example 1

Medium Concentration Unit Dose of rFGF-2 Employed in the Phase I Clinical Trial

The recombinant mature FGF-2 of U.S. Pat. No. 5,155,214 (Baird) was formulated as a medium concentration (0.2 μg/kg to about 36 μg/kg) unit dose and pharmaceutical composition and administered to rats, pigs and ultimately to humans in the Phase I clinical trial referenced herein. The various formulations are described below.

The Medium Concentration rFGF-2 Unit Dose was provided as a liquid in 3 cc type I glass vials with a laminated gray butyl rubber stopper and red flip-off overseal. The rFGF-2 unit dose contained 1.2 ml of 0.3 mg/ml rFGF-2 in 10 mM sodium citrate, 10 mM monothioglycerol, 1 mM disodium dihydrate EDTA (molecular weight 372.2), 135 mM sodium chloride, pH 5.0. Thus, in absolute terms, each vial (and unit dose) contained 0.36 mg rFGF-2. The vials containing the unit dose in liquid form were stored at 2° to 8° C.

The rFGF diluent was supplied in 5 cc type I glass vials with a laminated gray butyl rubber stopper and red flip-off overseal. The rFGF-2 diluent contains 10 mM sodium citrate, 10 mM monothioglycerol, 135 mM sodium chloride, pH 5.0. Each vial contained 5.2 ml of rFGF-2 diluent solution that was stored at 2° to 8° C.

The Medium Concentration rFGF-2 Pharmaceutical Composition that was infused was prepared by diluting the rFGF-2 unit dose with the rFGF diluent such that the infusion volume is 10 ml. In order to keep the EDTA concentration below the limit of 100 μg/ml, the total infusion volume was increased to 20 ml when proportionately higher absolute amounts of FGF-2 were administered to patients with high body weights.

Example 2

Selection Criteria for Patients with Coronary Artery Disease for Treatment with rFGF-2

The following selection criteria were applied to Phase I patients with coronary artery disease, whose activities were limited by coronary ischemia despite optimal medical management, and who were not candidates for approved revascularization therapies:

Inclusion Criteria: Subject is Eligible if:
Male or female, greater than or equal to 18 years of age
Diagnosis of coronary artery disease (CAD)
Suboptimal candidates for approved revascularization procedures, e.g., angioplasty, stents, coronary artery bypass graft (CABG) (or refuses those interventions)
Able to exercise at least three minutes using a modified Bruce protocol and limited by coronary ischemia
Inducible and reversible defect of at least 20% myocardium on pharmacologically stressed thallium sestamibi scan
CBC, platelets, serum chemistry within clinically acceptable range for required cardiac catheterization
Normal INR, or if anticoagulated with Coumadin, INR<2.0
Willing and able to give written informed consent to participate in this study, including all required study procedures and follow-up visits
Exclusion Criteria: Subject is not Eligible if:
Malignancy: any history of malignancy within past ten years, with the exception of curatively treated basal cell carcinoma.
Ocular conditions: proliferative retinopathy, severe non-proliferative retinopathy, retinal vein occlusion, Eales' disease, or macular edema or funduscopy by ophthalmologist: history of intraocular surgery within six months
Renal function: creatinine clearance below normal range adjusted for age; protein>250 mg or microalbumin>30 mg/24 h urine
Class IV heart failure (New York Heart Association)
Ejection fraction<20% by echocardiogram, thallium scan, MRI or gated pooled blood scan (MUGA)
Hemodynamically relevant arrhythmias (e.g., ventricular fibrillation, sustained ventricular tachycardia)
Severe valvular stenosis (aortic area<1.0 $cm^2$, mitral area<1.2 $cm^2$), or severe valvular insufficiency
Marked increase in angina or unstable angina within three weeks
History of myocardial infarction (MI) within three months
History of transient ischemic attack (TIA) or stroke within six months
History of CABG, angioplasty or stent within six months
History of treatment with transmyocardial laser revascularization, rFGF-2, or vascular enodothelial growth factor (VEGF) within six months
Females of child-bearing potential or nursing mothers
Any pathological fibrosis, e.g., pulmonary fibrosis, scleroderma
Known vascular malformation, e.g., AV malformation, hemangiomas
Coexistence of any disease which might interfere with assessment of symptoms of CAD, e.g., pericarditis, costochondritis, esophagitis, systemic vasculitis, sickle cell disease
Coexistence of any disease which limits performance of modified Bruce protocol exercise stress test, e.g., paralysis or amputation of a lower extremity, severe arthritis or lower extremities, severe chronic obstructive pulmonary disease (COPD)
Participation in clinical trials of investigational agents, devices or procedures within thirty days (or scheduled within sixty days of study drug)

Known hypersensitivity to rFGF-2 or related compounds

Any condition which makes the subject unsuitable for participation in this study in the opinion of the investigator, e.g., psychosis, severe mental retardation, inability to communicate with study personnel, drug or alcohol abuse

Example 3

Phase I Clinical Study on Recombinant FGF-2 Administered IC to Humans

Recombinant FGF-2 of U.S. Pat. No. 5,155,214 was administered to 52 human patients with severe CAD, who remained symptomatic despite optimal medical management and who refused or were suboptimal candidates for surgical or percutaneous revascularization, in a Phase I open label, single administration, dose escalation, two-site trial. The drug was administered as a single 20 minute infusion divided between two major sources of coronary blood supply (IC), using standard techniques for positioning a catheter into the patient's coronary artery (such as already employed in angioplasty). The doses (μg/kg) of rFGF-2 administered were 0.33 (n=4), 0.65 (n=4), 2.0 (n=8), 6.0 (n=4), 12.0 (n=4), 24 (n=8), 36 (n=10) and 48 (n=10). Angina frequency and quality of life was assessed by the Seattle Angina Questionnaire (SAQ) at a baseline (before rFGF-2 administration) and at about 60 days after rFGF-2 administration. Exercise tolerance time (ETT) was assessed by the threadmill test. Rest/exercise nuclear perfusion and gated sestamibi-determined rest ejection fraction (EF), and magnetic resonance imaging (MRI) were assessed at baseline, and at 30 days and 60 days post FGF-2 administration. Other end points that were evaluated included MRI (to objectively measure ejection fraction (EF), normal wall motion (NWM), targeted wall motion (TWM), normal wall thickness (NWT), targeted wall thickness (TWT), ischemic area zone and collateral extent). See Tables 2-4, respectively.

The preliminary safety results indicate that serious events were not dose related. Thus far, of the eight dosage groups, there were three deaths in the lowest dosage groups, i.e., at 0.65 μg/kg (Day 23), at 2.0 μg/kg (Day 57) and at 6.0 μg/kg (Day 63). There were six hospitalizations for acute myocardial infarction (MI) in three patients, i.e., one patient from each of groups 1 (0.33 μg/kg), 3 (2.0 μg/kg) and 4 (6.0 μg/kg). One of the three patients accounted for four of the six hospitalizations for acute MI. There was also one large B cell lymphoma that was diagnosed three weeks after dosing in a patient in group 4. The patient died at two months post dosing. Acute hypotension, seen at higher doses during or just subsequent to infusion, was managed by administration of fluids without need for a vasopressor. The maximum tolerated dose (MTD) in humans was defined as 36 μg/kg. (In contrast, in pigs, the MTD was 6.5 μg/ml.) Doses of rFGF-2 up to 48 μg/kg IC were managed in patients with aggressive fluid management, but were not tolerated due to acute and/or orthostatic hypotension in two out of ten patients. The half-life of the IC infused rFGF-2 was about one hour.

The human patients in this study that were treated with a single IC infusion of rFGF-2 exhibited a mean increase in ETT of 1.5 to 2 minutes. This is especially significant because an increase in ETT of >30 seconds is considered significant and a benchmark for evaluating alternative therapies, such as angioplasty. The angina frequency and quality of life, as measured by SAQ, showed a significant improvement at 57 days in all five subscales for the 28 patients (n=28) tested. See Tables 2 and 3. In particular, the mean changes in scores for the five criteria evaluated by the SAQ ranged from 13 to 36 with a mean change of 8 or more considered "clinically significant." See Table 2.

Magnetic resonance imaging (MRI) showed objective improvements following administration of a single unit dose of the FGF-2, including increased targeted wall motion at 30 and 60 days (p<0.05), and increased targeted wall thickening at 60 days (p<0.01). MRI further showed improved regional wall motion, and increased myocardial perfusion and collateral development in the targeted area for both the lower dose (0.33 μg/kg and 0.65 μg/kg) and higher dose (2.0 μg/kg and 12.0 μg/kg) groups in an 11 patient test group (n=11).

Abnormal perfusion zone, which was assessed at one of the sites on 28 patients, decreased significantly at 30 and 60 days (p<0.001).

In addition to the above criterion (i.e., ETT SAQ, MRI), a treatment is considered very successful if the angiogenic effects last at least six months. In the present Phase I study, the unexpectedly superior angiogenic effects were observed to last for 57-60 days in all dosage groups. [See Tables 2-4.] Based upon the results already obtained, it is expected that the angiogenic effects would last twelve months or more but at least six months, at which time the procedure could be repeated, if necessary.

Example 4

Proposed Phase II Clinical Study on Recombinant FGF-2 Administered to Humans to Treat Coronary Artery Disease The Phase II clinical trial of rFGF-2 of U.S. Pat. No. 5,155,214 for treating human patients for coronary artery disease is performed as a double blind/placebo controlled study having four arms: placebo, 0.3 μg/kg, 3 μg/kg and 30 μg/kg administered IC.

Example 5

Unit Dose and Pharmaceutical Composition of rFGF-2 for the Phase II Human Clinical Trial The rFGF-2 of U.S. Pat. No. 5,155,214 was formulated as a stock pharmaceutical composition for administration to humans in the Phase II clinical trial referenced herein. The various formulations are described below.

The Medium Concentration rFGF-2 stock pharmaceutical composition for Examples 2-4 was prepared as a liquid in 5 cc type I glass vials with a laminated gray butyl rubber stopper and red flip-off overseal. The rFGF-2 composition contained 0.3 mg/ml rFGF-2 of U.S. Pat. No. 5,155,214 in 10 mM sodium citrate, 10 mM monothioglycerol, 0.3 mM disodium dihydrate EDTA (molecular weight 372.2), 135 mM sodium chloride, pH 5.0. Each vial contained 3.7 ml of rFGF-2 drug product solution (1.11 mg rFGF-2 per vial). The resulting FGF-2 stock pharmaceutical composition in liquid form was stored at 2° to 8° C. Prior to use, the above-described FGF-2 composition was diluted with the "rFGF-2 placebo."

The rFGF placebo is supplied as a clear colorless liquid in 5 cc type I glass vials with a laminated gray butyl rubber stopper and red flip-off overseal. The rFGF-2 placebo is indistinguishable in appearance from the drug product and has the following formulation: 10 mM sodium citrate, 10 mM monothioglycerol, 0.3 mM disodium dihydrate EDTA (molecular weight 372.2), 135 mM sodium chloride, pH 5.0. Each vial contains 5.2 ml of rFGF-2 placebo solution. Like the unit dose, the rFGF-2 placebo is stored at 2° to 8° C.

The Medium Concentration rFGF-2 pharmaceutical composition that was ultimately infused IC, as described in Examples 2-4 herein, was prepared by diluting the rFGF-2 unit dose with the rFGF diluent such that the infusion volume is 10 ml. In order to keep the EDTA concentration below the limit of 100 µg/ml, the total infusion volume was increased to 40 ml when proportionately higher absolute amounts of FGF-2 were administered to subjects with high body weights.

Example 6

Selection Criteria for CAD Patients for the Phase II Human Clinical Trial of IC rFGF-2

Accordingly, the above-described evidence of an unexpectedly superior improvement in quality of life and of increased angiogenic efficacy in humans who were administered a single unit dosage of rFGF-2 in accordance with this invention, supports the patentability of the Applicants' unit dose, pharmaceutical composition and method of using the same.

Example 7

Inducing Angiogenesis In Vivo by the Administration of Ultra-Low Doses of rFGF-2 to the Myocardium of Miniswine Using a validated model of hibernating myocardium, miniswine underwent 90% left circumflex (LCx) coronary stenosis. Briefly, a hydraulically controlled occluder was placed around the proximal end of the LCx of miniswine. A flow probe was inserted into the LCx distal to the hydraulic occluder and the occluder was inflated to consistently provide 90% occlusion. The animals were tested in groups of 6. One month later, baseline positron emission tomography (PET) and dobutamine stress echocardiography (DSE) were performed and the animals randomized to 30 injections of either 100 µl carrier (n=5) or rFGF-2 in carrier (45 ng/injection; total dose 1.35 µg) (n=5) in the LCx region. In the above injections, the FGF-2 was the recombinant mature FGF-2 (SEQ ID NO: 2) of U.S. Pat. No. 5,155,214. The carrier was a sterile aqueous solution comprising 10 mM thioglycerol, 135 mM NaCl, 10 mM sodium citrate and 1 mM EDTA, pH 5. The total dose (1.35 µg) of FGF-2 provided in this example is 1/100 the intracoronary (IC) delivered dose (135 µg) that was found to be effective in the ameroid porcine model, wherein the LCx was occluded 100%.

Figure 10:
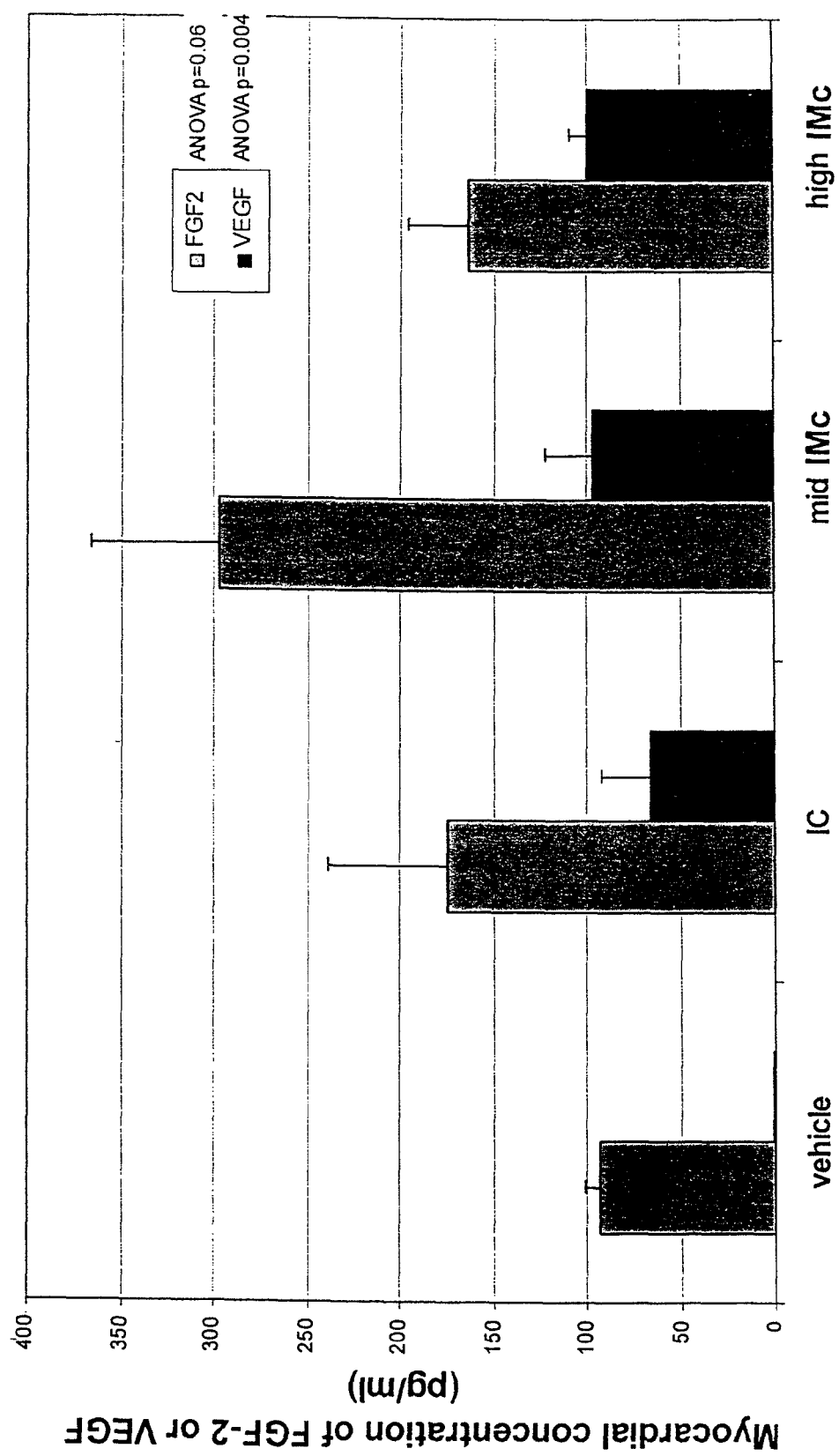
FIG. 10 is a bar graph comparing the intracellular concentrations (pg/ml) of VEGF (measured as $VEGF_{165}$) and FGF-2 in ischemic myocardial cells 3 months after treatment with 0.6 µg/kg (13.5 µg) FGF-2 of SEQ ID NO: 2 IC in the ameroid pig model (100% occlusion of the LCx), or with vehicle or 0.6 µg/kg (13.5 µg) FGF-2 of SEQ ID NO: 2 ("mid" dose) or 6.0 µg/kg (135 µg) FGF-2 of SEQ ID NO: 2 ("high" dose) in the pig model of the hibernating myocardium (90% occlusion of the LCx). Surprisingly, the FGF-2 treated ischemic cells were producing statistically significant amounts of both VEGF and FGF-2 up to 3 months after treatment. More surprisingly, the highest concentrations of intracellular FGF-2 were induced by those cells treated with the "mid" dose IMc.

In the animals that received the injections of rFGF-2 in their myocardium, the LCx region myocardial blood flow (MBF) at rest, as measured by PET, increased from 61.3±4.4% of non-ischemic septal values at baseline (day 0) to 82.8±3.1% at 6 months postoperatively (p<0.001). The wall motion score index (WMSI) at rest for the LCx region was 2.4±0.2 at baseline and improved to 2.2±0.2 (p=0.08 vs baseline) at six months. Likewise, WMSI for the LCx region at peak stress was 2.2±0.4 at baseline (day 0) and improved to 1.8±0.3 (p=0.05) at six months. (FIG. 5) There was no significant change in MBF or rest or stress WMSI in the vehicle treated animals at any time point. Six months after treatment, the miniswine were sacrificed and the capillary density of the treated ischemic myocardium was determined. The FGF-2 treated miniswine exhibited a capillary density of about 4400/unit volume, versus about 1700 for the saline treated group. (FIG. 6) Western blot analysis revealed significantly greater upregulation of VEGF (measured as VEGF 165) and FGF-2 in the chronically ischemic FGF-2 treated regions versus that observed with vehicle (p<0.05). FIG. 10. Surprisingly, the upregulation of VEGF and FGF-2 continued for at least 3 months after treatment. (FIG. 10). Thus, the direct intramyocardial injection of an ultra-low dose of angiogenic agent, such as rFGF-2, improves MBF, contractile reserve, perfusion (FIG. 4), myocardial function as measured by DSE (FIG. 5), and capillary density (FIG. 6) in the treated regions of the myocardium. Accordingly, injecting an ultra-low dose of angiogenic agent IMc represents a viable method for inducing angiogenesis and a viable alternative therapy for the treatment of CAD and/or MI.

Example 8

Inducing Angiogenesis In Vivo by Administration of Various Doses of rFGF-2 to the Myocardium of Miniswine Using the same validated model of hibernating myocardium described in Example 7, miniswine underwent 90% left circumflex (LCx) coronary stenosis. Briefly, a hydraulically controlled occluder was placed around the proximal end of the LCx of miniswine. A flow probe was inserted into the LCx distal to the hydraulic occluder and the occluder was inflated to consistently provide 90% occlusion. Four groups of animals were tested in groups of 6. The groups were as follows:

IMc mid dose: 6 animals (0.6 µg/kg total dose IMc
 30 injections in LCx territory, no heparin IMc
IMc high dose: 6 animals (6.0 µg/kg total dose IMc
 30 injections in LCx territory, no heparin IMc
Positive control: 6 animals (6.0 µg/kg I.C. in the ameroid model (100% occlusion of the LCx) total dose 135 µg, delivered as
 heparin 70 U/kg 5 min before start of infusion
 ½ dose RCA if possible, ½ dose LCx or LAD (3 µg/kg/artery), each delivered by infusion over 10 minutes per artery (20 minutes total infusion time)
Negative control: 6 animals–vehicle/saline×30 injections IMc.

The miniswine were randomly assigned to treatment groups at time of surgery.

Phase 1: Establishment of Baseline and Initiation of Treatment
 Established a baseline for a hibernating myocardium as described, with perfusion determined by PET and cardiac function by DSE immediately.
 PRE-TREATMENT (under anesthesia):
  Recorded baseline heart rate (HR)/blood pressure (BP)
  Collected blood for:
   serum chemistries, CBC, cardiac enzymes, such as CPK MB, cardiac troponin I ("TNI") or cardiac troponin T ("TNT"), associated with damaged cardiac myocytes
   spun plasma for rFGF-2 assay pre-treatment (freeze at −70° C.)
  EKG (3 leads, with rhythm strip)
 DURING TREATMENT:
  Recorded HR and BP data; treat hypotension with fluids
  Recorded rhythm changes per monitor
  Treated the four groups with FGF-2 (mid and high dose), a negative control, and a positive control as described above.
 POST-TREATMENT:
  Recorded HR/BP until back to baseline
  Collected second set of serum chemistries, CBC, cardiac enzymes and spun plasma for rFGF-2 assay at latest possible point post-treatment (2 hrs minimum) USE SAME TIME post-treatment for blood collection in all animals. See above for handling.
EKG (3 leads, with rhythm strip)
Phase 2: Follow-Up @ 3 Months Post-Treatment
Under anesthesia:
Recorded HR and BP
Collected blood for serum chemistries, CBC, cardiac enzymes and spun plasma for rFGF-2 assay. See above for handling
Performed EKG (3 leads, with rhythm strip)
Determined perfusion by PET and myocardial function at stress by DSE. Treatment group blinded to 2 readers
Phase 3: Histology and Final Report
Post-sacrifice: The minipigs were sacrificed 3 months after treatment with FGF-2 or control.
Gross pathology of hearts: Recorded evidence of injection site or other cardiac pathology (infarcts, scar, injection site changes, pericardial changes)
Tissues: Septum, Anterior wall, LCx territory
Stained with hematoxylin and eosin (H&E) for architecture
Stained with trichrome for fibrosis
Stained for alkaline phosphatase to identify endothelial tissue
Performed a blinded assessment of overall vascular density in mid-myocardium cross-section
Searched for local pathology at injection sites (fibrosis, vascularity, myocyte loss, infarction, etc.)

Figure 7:
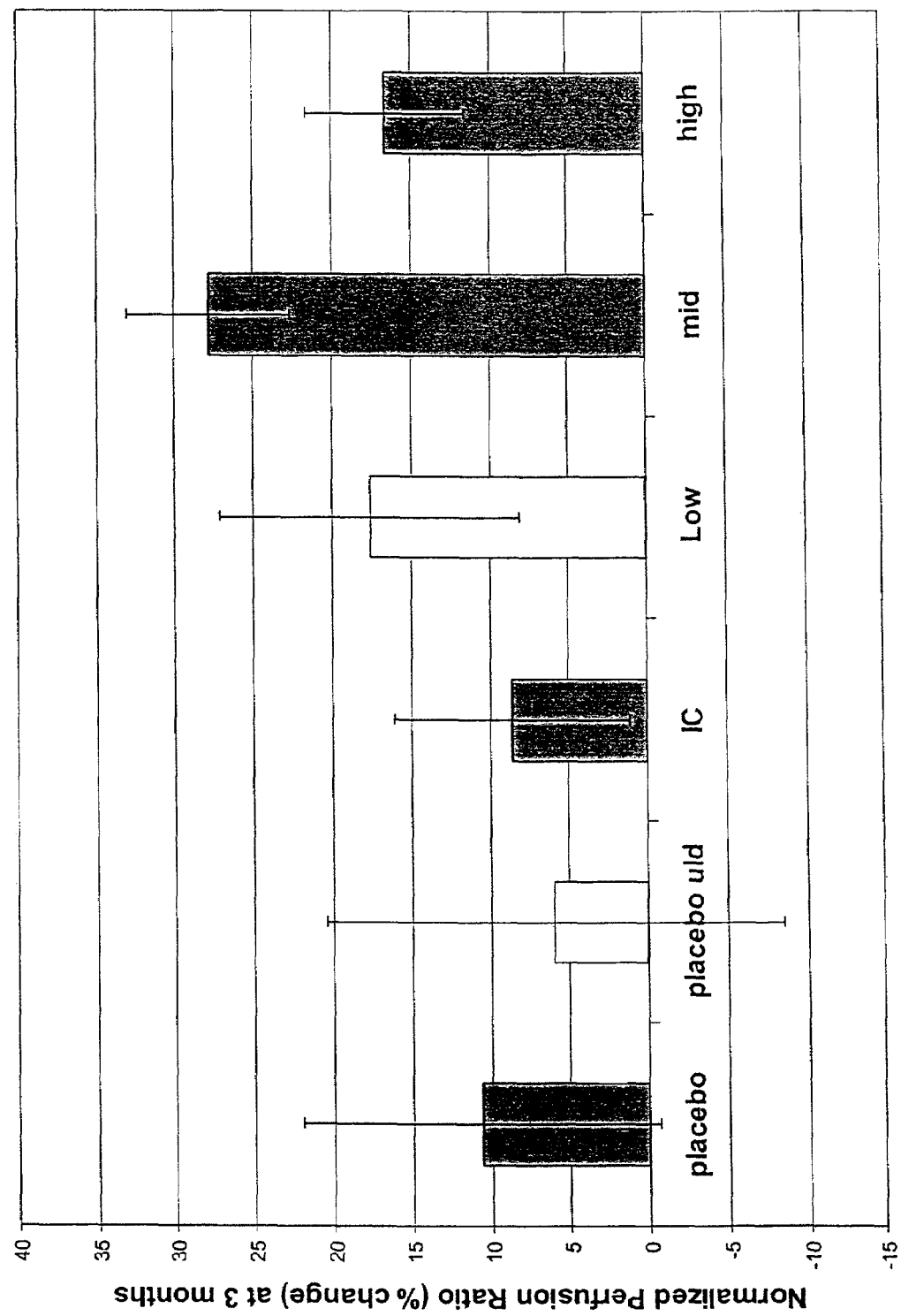
FIG. 7 is a bar graph, comparing the normalized myocardial perfusion (reported as % change from baseline) in the pig model of the hibernating myocardium, as measured by positron emission tomography (PET), at 3 months following: administering saline (placebo); a unit dose containing 0.06 µg/kg (1.35 µg) of rFGF-2 (SEQ ID NO: 2) "low"; a unit dose containing 0.6 µg/kg (13.5 µg) of rFGF-2 (SEQ ID NO: 2) "mid"; a unit dose containing 6.0 µg/kg (135 µg) of rFGF-2 (SEQ ID NO: 2) "high". The bar graph shows that the greatest % change in normalized perfusion (i.e., a 27.5% increase) occurred for the "mid" dose, with the "low" and "high" doses showing comparable changes, 17.5% and 17%, respectively. The data in FIG. 7 is the result of two separate experiments (light bars and dark bars) with the placebo designated as "uld" (ultra-low dose) being the placebo for the "low" dose, shown as the light colored bars.

The normalized perfusion ratio of the treated ischemic myocardium was determined by PET three months after treatment with positive or negative controls (as described above) and after treatment IMc with the "mid" (0.6 µg/kg (13.5 µg)) or "high" 6.0 µg/kg (135 µg)) doses of rFGF-2 (SEQ ID NO: 2). This data is shown as the bar graph of FIG. 7, which also combines the normalized perfusion data from the "low" (0.06 µg/kg (1.35 µg)) dose of FGF-2 as determined in Example 7. FIG. 7 shows that the greatest % change in normalized perfusion (i.e., a 27.5% increase) surprisingly occurred for the "mid" dose, with the "low" and "high" doses showing lower changes of 17.5% and 17%, respectively. The data in FIG. 7 is the result of two separate experiments (light bars and dark bars) with the light colored placebo designated as "uld" (ultra-low dose) being the placebo for the "low" dose, also shown as a light colored bar.

Figure 8:
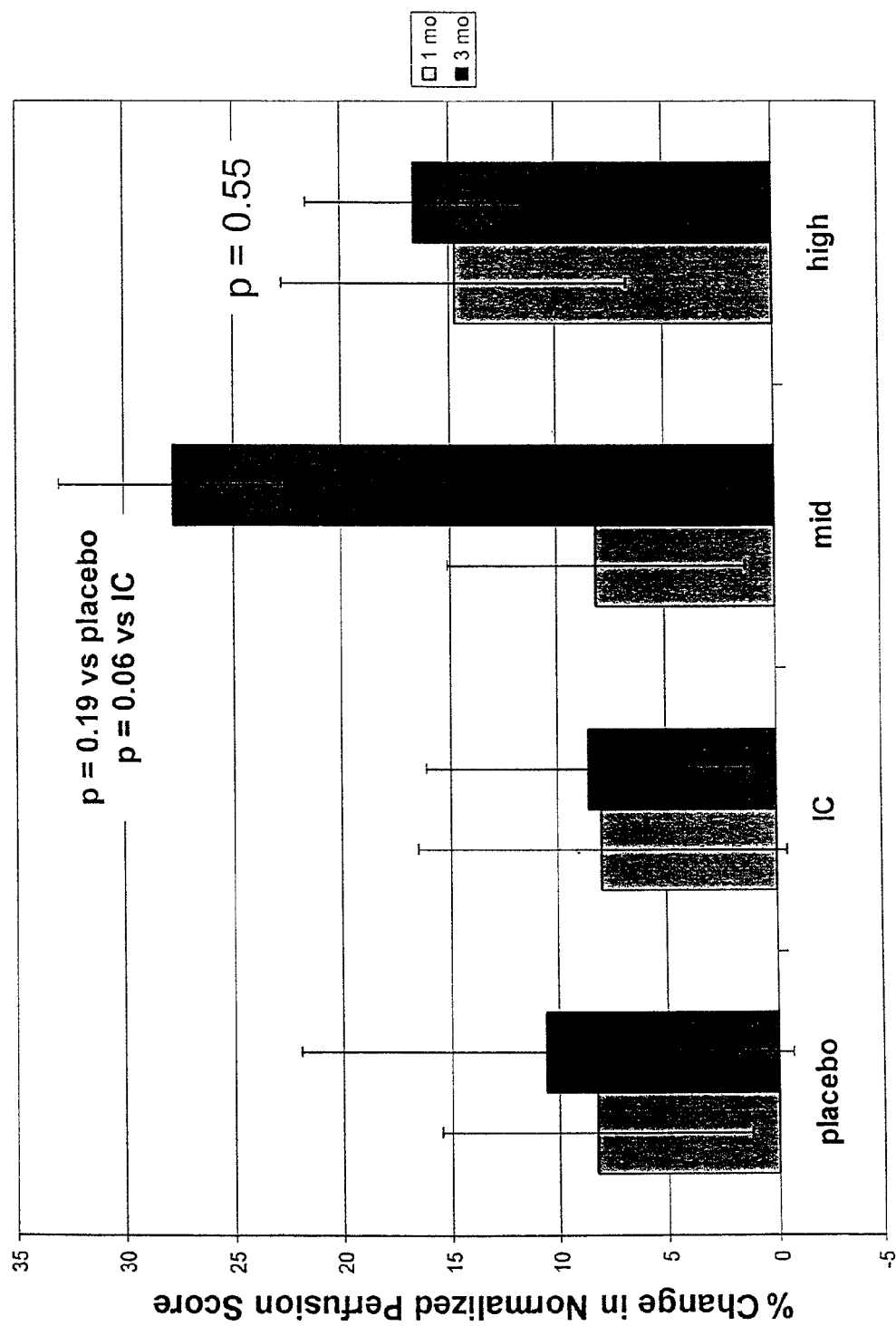
FIG. 8 is a bar graph, comparing the % change in normalized myocardial perfusion (as measured by PET) in the pig model of the ameroid (100% occlusion of the LCx) myocardium at 1 month and 3 months after intracoronary (IC) infusion of 0.6 µg/kg rFGF-2, versus the % change in normalized myocardial perfusion in the pig model of the hibernating myocardium (90% occlusion of the LCx) at 1 month and 3 months after intramyocardial (IMc) injection of the following: saline (placebo); a unit dose containing 0.6 µg/kg (13.5 µg) of rFGF-2 (SEQ ID NO: 2) "mid"; a unit dose containing 6.0 µg/kg (135 µg) of rFGF-2 (SEQ ID NO: 2) "high". The bar graph shows that the greatest % increase in normalized perfusion occurred for the "mid" dose of rFGF-2 IMc at 3 months post treatment. The "high" dose unexpectedly showed a lower increase in normalized perfusion than was achieved for the "mid" dose.
Figure 9:
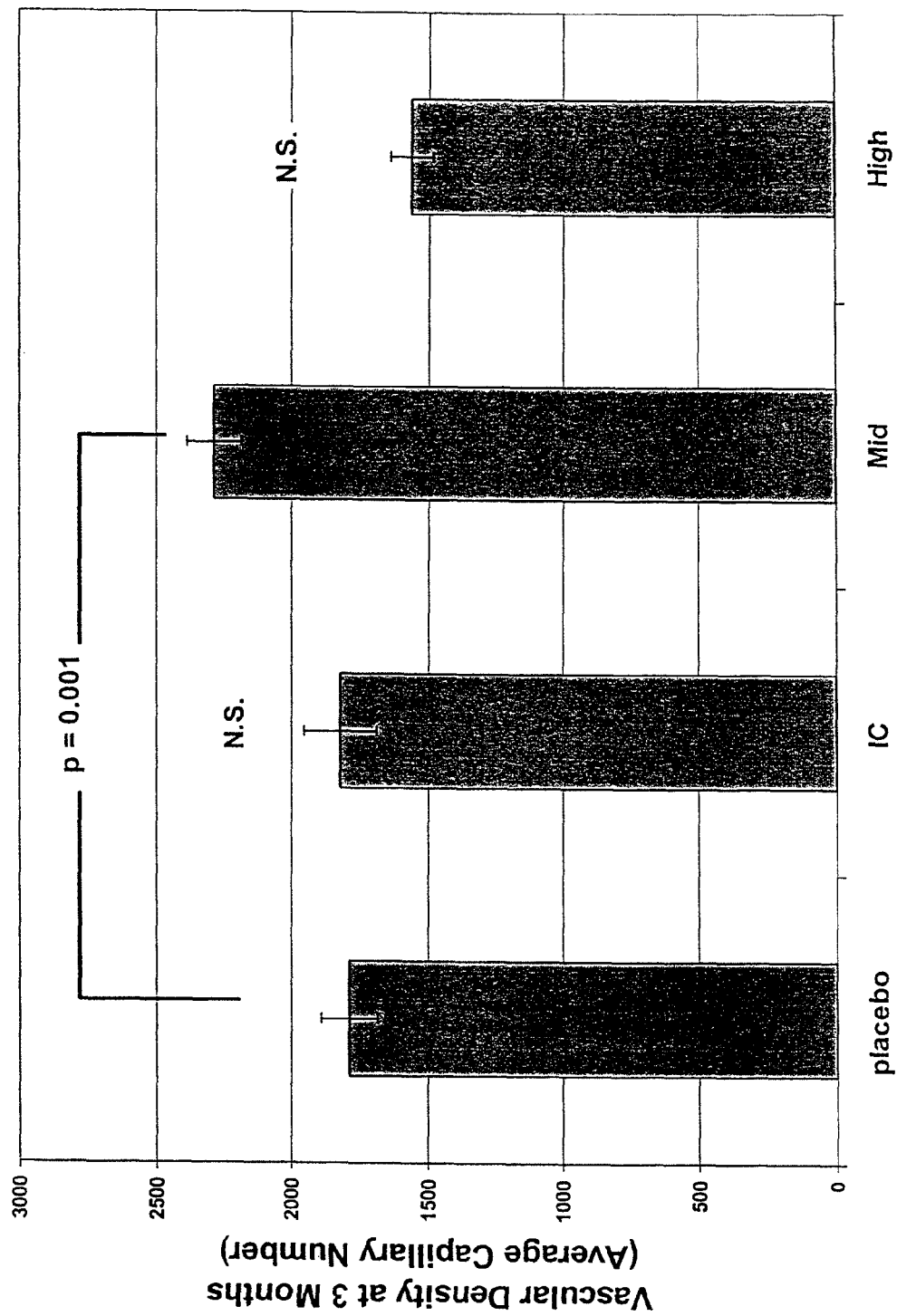
FIG. 9 is a bar graph comparing vascular density (average vessel number in a designated volume of treated myocardium) for the pig model of the hibernating myocardium treated with 0.6 µg/kg ("mid" dose) or 6.0 µg/kg ("high" dose) rFGF-2 (SEQ ID NO: 2) IMc versus the ameroid pig model (100% occlusion of the LCx) treated with 6.0 µg/kg rFGF-2 (SEQ ID NO: 2) IC, versus treatment with saline IMc (placebo). The results show that the greatest increase in vascular density was produced by the "mid" dose (0.6 µg/kg or 13.5 µg rFGF-2) that was administered IMc.

The % change in normalized perfusion for ischemic myocardium treated with the mid and high dose groups at 1 and 3 months after treatment is compared to positive (IC) and negative (placebo) controls in the bar graph of FIG. 8. The "high" dose showed a higher increase in normalized perfusion than was achieved for the "mid" dose at 1 month post-treatment. However, the % increase in normalized perfusion unexpectedly occurred for the "mid" dose of rFGF-2 IMc at 3 months post treatment. This unexpectedly superior result is corroborated by the unexpectedly greater vascular density that was observed for the "mid" dose treated group than for the "high" dose treated group. (FIG. 9) Moreover, both showings of unexpectedly superior results for the mid dose treated group are consistent with the unexpectedly superior upregulation of intracellular FGF-2 in the treated ischemic myocardium that is observed three months after treatment in the "mid" dose (about 290 pg/ml) relative to that observed in the "high" dose group (about 170 pg/ml) or in the positive IC control (about 175 pg/ml).

Thus, while all dosages of FGF-2 that are administered IMc in accordance with the method of the present invention increase perfusion and cardiac function, there appears to be an unexpectedly superior (mid) dosage of FGF-2 that occurs from about 0.3 µg/kg (or 6.75 µg or 6,750 ng) to about 3.0 µg/kg (or 67.5 µg or 67,500 ng).

What is claimed is:

1. A method for inducing angiogenesis in a heart of a patient, comprising injecting an effective amount of an angiogenic agent directly into the myocardium of said patient in one or more areas in need of angiogenesis, said effective amount of angiogenic agent being from about 5 ng to about 1,350 ng of said angiogenic agent, wherein said angiogenic agent is a fibroblast growth factor (FGF) having angiogenic activity, or an angiogenically active fragment or mutein thereof, wherein said fragment comprises at least that portion of the amino acid sequence for said FGF that corresponds to residues 30-110 of the FGF-2 sequence set forth in SEQ ID NO:2 or SEQ ID NO:6 when the amino acid sequence for said FGF is aligned with the FGF-2 sequence set forth in SEQ ID NO:2 or SEQ ID NO:6 to obtain maximum homology, and wherein said angiogenically active mutein has at least 90% amino acid sequence identity to said FGF.

2. The method of claim 1, wherein said patient has symptoms of coronary artery disease (CAD) or a myocardial infarction (MI).

3. A method for treating a human patient for coronary artery disease, comprising injecting an effective amount of an angiogenic agent directly into the myocardium in one or more areas in need of treatment for said disease, said effective amount of angiogenic agent being from about 5 ng to about 1,350 ng of said angiogenic agent, wherein said angiogenic agent is a fibroblast growth factor (FGF) having angiogenic activity, or an angiogenically active fragment or mutein thereof, wherein said fragment comprises at least that portion of the amino acid sequence for said FGF that corresponds to residues 30-110 of the FGF-2 sequence set forth in SEQ ID NO:2 or SEQ ID NO:6 when the amino acid sequence for said FGF is aligned with the FGF-2 sequence set forth in SEQ ID NO:2 or SEQ ID NO:6 to obtain maximum homology, and wherein said angiogenically active mutein has at least 90% sequence identity to said angiogenic agent.

4. A method for increasing vascular perfusion or vascular density in the myocardium comprising injecting an effective amount of an angiogenic agent directly into an area of the myocardium in need of an increase in perfusion or vascular density, said effective amount being within the range of about 5 ng to about 1,350 ng of said angiogenic agent, wherein said angiogenic agent is a fibroblast growth factor (FGF) having angiogenic activity, or an angiogenically active fragment or mutein thereof, wherein said fragment comprises at least that portion of the amino acid sequence for said FGF that corresponds to residues 30-110 of the FGF-2 sequence set forth in SEQ ID NO:2 or SEQ ID NO:6 when the amino acid sequence for said FGF is aligned with the FGF-2 sequence set forth in SEQ ID NO:2 or SEQ ID NO:6 to obtain maximum homology, and wherein said angiogenically active mutein has at least 90% sequence identity to said angiogenic agent.

* * * * *

UNITED STATES PATENT AND TRADEMARK OFFICE
CERTIFICATE OF CORRECTION

PATENT NO.        : 8,178,493 B2  
APPLICATION NO.   : 12/419038  
DATED             : May 15, 2012  
INVENTOR(S)       : David T. Hung et al.

Page 1 of 1

It is certified that error appears in the above-identified patent and that said Letters Patent is hereby corrected as shown below:

Title page,

Item (73),
"Assignee: Novartis Vaccines and Diagnostics, Inc., Emeryville, CA (US)" should read
--Assignees: Novartis Vaccines and Diagnostics, Inc., Emeryville, CA (US);
Duke University, Durham, NC (US)--.

Signed and Sealed this
Twentieth Day of October, 2015

Michelle K. Lee
*Director of the United States Patent and Trademark Office*